(12) United States Patent
Lightner et al.

(10) Patent No.: US 6,372,965 B1
(45) Date of Patent: *Apr. 16, 2002

(54) GENES FOR MICROSOMAL DELTA-12 FATTY ACID DESATURASES AND HYDROXYLASES FROM PLANTS

(75) Inventors: Jonathan Edward Lightner, Marietta, PA (US); John Joseph Okuley, Columbus, OH (US); William Hitz; Anthony John Kinney, both of Wilmington, DE (US); Luis Perez-Grau, Davis, CA (US); Narendra S. Yadav, Chadds Ford, PA (US)

(73) Assignee: E.I. du Pont de Nemours and Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,962

(22) Filed: Aug. 14, 1998

Related U.S. Application Data

(63) Continuation of application No. 08/262,401, filed on Jun. 20, 1994, now abandoned, which is a continuation-in-part of application No. PCT/US93/09987, filed on Oct. 15, 1993, which is a continuation-in-part of application No. 07/977,339, filed on Nov. 17, 1992, now abandoned.

(51) Int. Cl.$^7$ .............................. A01H 5/00; C12N 5/04; C12N 15/82
(52) U.S. Cl. .................... 800/298; 800/281; 435/320.1; 435/419; 435/468; 536/23.6
(58) Field of Search ................................. 800/281, 298; 435/69.1, 468, 419, 320.1; 536/23.6

(56) References Cited

U.S. PATENT DOCUMENTS

| | | | |
|---|---|---|---|
| 5,668,292 A | 9/1997 | Somerville et al. | ......... 800/205 |
| 5,801,026 A | 9/1998 | Somerville et al. | ....... 435/172.3 |

FOREIGN PATENT DOCUMENTS

| | | | |
|---|---|---|---|
| WO | WO 90/10380 | 9/1990 | ............ A01H/1/04 |
| WO | WO 91/13972 | 3/1991 | ............ C12N/1/21 |
| WO | WO 93/06712 | 4/1993 | ............ A01H/1/00 |
| WO | WO 93/11245 | 6/1993 | ........... C12N/15/53 |

OTHER PUBLICATIONS

Bafor, M. et al., Ricinoleic acid biosynthesis and triacylglycerol assembly in microsomal preparations from developing castor–bean (*Ricinus communis*) endosperm, *Biochem. J.*, 280, 507–514, 1991.
Van de Loo, F. J. et al., An oleate 12–hydroxylase from *Ricinus communis* L. is a fatty acyl desaturase homolog, *Proc. Natl. Acad. Sci. USA*, 92, 6743–6747, Jul. 1995.
Broun, P. et al., Accumulation of Ricinoleic, Lesquerolic, and Densipolic Acids in Seeds of Transgenic Arabidopsis Plants That Express a Fatty Acyl Hydroxylase cDNA from Castor Bean, *Plant Physiol.*, 113, 933–942, 1997.
Broun, P. et al., Expression of Castor and *Lesquerlla Fendleri* Oleate—12 Hydroxylases in Transgenic Plants: Effects on Lipid Metabolism and Inferences on Structure–Function Relationships in Fatty Acid Hydoxylases, *12$^{th}$ International Symposium on Plant Lipids*, Jul. 7–12, 1996.
Gunstone, F. D. et al., Hydroxy acids and Castor oil, *The Lipid Handbook*, Second Edition, pp. 15–16; 55–56.
Broun, P. et al., Expression of Castor and *L. Fendleri* Oleate 12—Hydroxylases in Transgenic Plants, *Physiology, Biochemistry and Molecular Biology of Plant Lipids*, 342–344, 1997.
Mattson et al., Journal of Lipid Research (1985)26:194–202.
Gailliard, 1980, vol. 4, pp. 85–116 In: Stumpf, P.K. Ed., The Biochemistry of Plants, Academic Press, New York.
Mesink et al., New England J. Medicine (1990)N323: 439–445.
Knowles (1980) pp 35–38, In: Applewhite, T.H., Ed., World Conference on Biotechnology for the Fats and Oils Industry Proceedings, American Oil Chemists Society.
Browse et al., Ann. Rev. Plant Physiol. Mol. Biol. (1991) 42:467–506.
Ohlrogge, et al., Biochim Biophys. Acta(1991) 1082:1–26.
Wang et al., Plant Physiol. Biochem. (1988) 26:777–792.
Thompson, et al., Proc. Natl. Acad. Sci USA (1991) 88:2578–2582.
Shanklin et al., Proc. Natl. Acad. Sci USA(1991) 88:2510–2514.
Stukey et al., J. Biol. Chem. (1990) 265:20144–20149.
Thiede et al., J. Biol. Chem. (1986) 261:13230–13235.
Kaestner et al., J. Biol. Chem. (1989) 264:14755–1476.
Wada, et al., Nature (1990) 347: 200–203.
U.S. application No.:07/804,259 Filed Dec. 4, 1991.
Galliard & Stumpf (1966) J. Biol. Chem 241:5806–5812.
Cronan et al. (1988) J. Biol. Chem 263: 4641–4646.
Buist et al, (1987) Tetrahedron Letters 28:857–860.
Buist & Marecak (1991) Tetrahedron Letters 32:891–894.
Bafor et al. (1991) Plant Physiol. 280:507–514.
Moreau & Stumpf (Plant Physiol. (1981) 67:672–676).
Bafor et al., Biochem J (1991) 280:507–514.
Wiberg et al. 10$^{th}$ International Symposium on Metabolism Structure & Function of Plant Lipid (1992) Jerbay Tunisia.
Feldmann, et al., Mol. Gen. Genetics (1987) 208:1–9.
Elledge et al. (1991) Proc. Natl. Acad Sci USA 88:1731–1735.
Wada et al., Nature (1990) 347:200–203.

(List continued on next page.)

*Primary Examiner*—Elizabeth F. McElwain

(57) ABSTRACT

The preparation and use of nucleic acid fragments encoding fatty acid desaturase enzymes are described. The invention permits alteration of plant lipid composition. Chimeric genes incorporating such nucleic acid fragments with suitable regulatory sequences may be used to create transgenic plants with altered levels of unsaturated fatty acids.

13 Claims, No Drawings

OTHER PUBLICATIONS

Genbank ID: OSDESA, GenBank Accession No.:X53508.
Mensink et al, *New England Journal of Medicine*, 323, 439–445 (1990).
Kaestner et al, *J. Biol. Chem.*, 264, 1475–1476 (1989).
Cahoon et al, *Proc. Natl. Acad. Sci. USA*, 89, 11184–11188 (1992).
Arondel, V. et al, *Science*, 258, 1353–1355 (1992).
Gunstone et al, Eds., *The Lipids Handbook*, Chapman and Hall Ltd., Cambridge (1986) (entire reference).
Somerville, C., *MSU–DOE Plant Research Laboratory Annual Report* (1992) (entire reference).
Greenwood & Bewley, *Can. J. Bot.*, 601751–1760 (1982).
James et al, *Biochem J.*, 95, 448–452 (1965).
Canvin, *Can. J. Biochem. Physiol.*, 41, 1879–1885 (1963).
Sargent, *Meth. Enzymol.*, 152, 423–432 (1987).

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 1372 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Arabidopsis thaliana (vii) IMMEDIATE SOURCE:
      (B) CLONE: p92103

(ix) FEATURE:
      (A) NAME/KEY: CDS
      (B) LOCATION: 93..1244

(xi) SEQUENCE DESCRIPTION: SEQ ID NO: 1:

```
AGAGAGAGAG ATTCTGCGGA GGAGCTTCTT CTTCGTAGGG TGTTCATCGT TATTAACGTT        60

ATCGCCCCTA CGTCAGCTCC ATCTCCAGAA AC ATG GGT GCA GGT GGA AGA ATG         113
                                 Met Gly Ala Gly Gly Arg Met
                                   1               5

CCG GTT CCT ACT TCT TCC AAG AAA TCG GAA ACC GAC ACC ACA AAG CGT         161
Pro Val Pro Thr Ser Ser Lys Lys Ser Glu Thr Asp Thr Thr Lys Arg
```

```
                10                    15                    20
GTG CCG TGC GAG AAA CCG CCT TTC TCG GTG GGA GAT CTG AAG AAA GCA              209
Val Pro Cys Glu Lys Pro Pro Phe Ser Val Gly Asp Leu Lys Lys Ala
     25                  30                  35

ATC CCG CCG CAT TGT TTC AAA CGC TCA ATC CCT CGC TCT TTC TCC TAC              257
Ile Pro Pro His Cys Phe Lys Arg Ser Ile Pro Arg Ser Phe Ser Tyr
 40                  45                  50                  55

CTT ATC AGT GAC ATC ATT ATA GCC TCA TGC TTC TAC TAC GTC GCC ACC              305
Leu Ile Ser Asp Ile Ile Ile Ala Ser Cys Phe Tyr Tyr Val Ala Thr
                     60                  65                  70

AAT TAC TTC TCT CTC CTC CCT CAG CCT CTC TCT TAC TTG GCT TGG CCA              353
Asn Tyr Phe Ser Leu Leu Pro Gln Pro Leu Ser Tyr Leu Ala Trp Pro
             75                  80                  85

CTC TAT TGG GCC TGT CAA GGC TGT GTC CTA ACT GGT ATC TGG GTC ATA              401
Leu Tyr Trp Ala Cys Gln Gly Cys Val Leu Thr Gly Ile Trp Val Ile
         90                  95                 100

GCC CAC GAA TGC GGT CAC CAC GCA TTC AGC GAC TAC CAA TGG CTG GAT              449
Ala His Glu Cys Gly His His Ala Phe Ser Asp Tyr Gln Trp Leu Asp
     105                 110                 115

GAC ACA GTT GGT CTT ATC TTC CAT TCC TTC CTC CTC GTC CCT TAC TTC              497
Asp Thr Val Gly Leu Ile Phe His Ser Phe Leu Leu Val Pro Tyr Phe
120                 125                 130                 135

TCC TGG AAG TAT AGT CAT CGC CGT CAC CAT TCC AAC ACT GGA TCC CTC              545
Ser Trp Lys Tyr Ser His Arg Arg His His Ser Asn Thr Gly Ser Leu
                140                 145                 150

GAA AGA GAT GAA GTA TTT GTC CCA AAG CAG AAA TCA GCA ATC AAG TGG              593
Glu Arg Asp Glu Val Phe Val Pro Lys Gln Lys Ser Ala Ile Lys Trp
            155                 160                 165

TAC GGG AAA TAC CTC AAC AAC CCT CTT GGA CGC ATC ATG ATG TTA ACC              641
Tyr Gly Lys Tyr Leu Asn Asn Pro Leu Gly Arg Ile Met Met Leu Thr
        170                 175                 180

GTC CAG TTT GTC CTC GGG TGG CCC TTG TAC TTA GCC TTT AAC GTC TCT              689
Val Gln Phe Val Leu Gly Trp Pro Leu Tyr Leu Ala Phe Asn Val Ser
    185                 190                 195

GGC AGA CCG TAT GAC GGG TTC GCT TGC CAT TTC TTC CCC AAC GCT CCC              737
Gly Arg Pro Tyr Asp Gly Phe Ala Cys His Phe Phe Pro Asn Ala Pro
200                 205                 210                 215

ATC TAC AAT GAC CGA GAA CGC CTC CAG ATA TAC CTC TCT GAT GCG GGT              785
Ile Tyr Asn Asp Arg Glu Arg Leu Gln Ile Tyr Leu Ser Asp Ala Gly
                220                 225                 230

ATT CTA GCC GTC TGT TTT GGT CTT TAC CGT TAC GCT GCT GCA CAA GGG              833
Ile Leu Ala Val Cys Phe Gly Leu Tyr Arg Tyr Ala Ala Ala Gln Gly
            235                 240                 245

ATG GCC TCG ATG ATC TGC CTC TAC GGA GTA CCG CTT CTG ATA GTG AAT              881
Met Ala Ser Met Ile Cys Leu Tyr Gly Val Pro Leu Leu Ile Val Asn
        250                 255                 260

GCG TTC CTC GTC TTG ATC ACT TAC TTG CAG CAC ACT CAT CCC TCG TTG              929
Ala Phe Leu Val Leu Ile Thr Tyr Leu Gln His Thr His Pro Ser Leu
    265                 270                 275

CCT CAC TAC GAT TCA TCA GAG TGG GAC TGG CTC AGG GGA GCT TTG GCT              977
Pro His Tyr Asp Ser Ser Glu Trp Asp Trp Leu Arg Gly Ala Leu Ala
280                 285                 290                 295

ACC GTA GAC AGA GAC TAC GGA ATC TTG AAC AAG GTG TTC CAC AAC ATT             1025
Thr Val Asp Arg Asp Tyr Gly Ile Leu Asn Lys Val Phe His Asn Ile
                300                 305                 310

ACA GAC ACA CAC GTG GCT CAT CAC CTG TTC TCG ACA ATG CCG CAT TAT             1073
Thr Asp Thr His Val Ala His His Leu Phe Ser Thr Met Pro His Tyr
            315                 320                 325

AAC GCA ATG GAA GCT ACA AAG GCG ATA AAG CCA ATT CTG GGA GAC TAT             1121
```

```
Asn Ala Met Glu Ala Thr Lys Ala Ile Lys Pro Ile Leu Gly Asp Tyr
        330                 335                 340

TAC CAG TTC GAT GGA ACA CCG TGG TAT GTA GCG ATG TAT AGG GAG GCA     1169
Tyr Gln Phe Asp Gly Thr Pro Trp Tyr Val Ala Met Tyr Arg Glu Ala
        345                 350                 355

AAG GAG TGT ATC TAT GTA GAA CCG GAC AGG GAA GGT GAC AAG AAA GGT     1217
Lys Glu Cys Ile Tyr Val Glu Pro Asp Arg Glu Gly Asp Lys Lys Gly
360                 365                 370                 375

GTG TAC TGG TAC AAC AAT AAG TTA TGAGCATGAT GGTGAAGAAA TTGTCGACC     1271
Val Tyr Trp Tyr Asn Asn Lys Leu
                380

TTCTCTTGTC TGTTTGTCTT TTGTTAAAGA AGCTATGCTT CGTTTTAATA ATCTTATT     1331

CCATTTTGTT GTGTTATGAC ATTTTGGCTG CTCATTATGT T                       1372

(2) INFORMATION FOR SEQ ID NO: 2:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Ala Gly Gly Arg Met Pro Val Pro Thr Ser Ser Lys Lys Ser
 1               5                  10                  15

Glu Thr Asp Thr Thr Lys Arg Val Pro Cys Glu Lys Pro Pro Phe Ser
             20                  25                  30

Val Gly Asp Leu Lys Lys Ala Ile Pro Pro His Cys Phe Lys Arg Ser
         35                  40                  45

Ile Pro Arg Ser Phe Ser Tyr Leu Ile Ser Asp Ile Ile Ala Ser
     50                  55                  60

Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255
```

```
Val Pro Leu Leu Ile Val Asn Ala Phe Leu Val Leu Ile Thr Tyr Leu
        260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
        290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
                340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
        370                 375                 380

(2) INFORMATION FOR SEQ ID NO: 3:

(i) SEQUENCE CHARACTERISTICS:
        (A) LENGTH: 1426 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Brassica napus (ix) FEATURE:
        (A) NAME/KEY: CDS
        (B) LOCATION: 130..1284

(xi) SEQUENCE DESCRIPTION: SEQ ID NO: 3:

GGCACGAGCT CGTGCCGAAT TCGGCACGAG AGGAGACAGA GAGAGAGTTT GAGGAGGAGC       60

TTCTTCGTAG GGTTCATCGT TATTAACGTT AAATCTTCAT CCCCCCCTAC GTCAGCCAG      120

TCAAGAAAC ATG GGT GCA GGT GGA AGA ATG CAA GTG TCT CCT CCC TCC         168
          Met Gly Ala Gly Gly Arg Met Gln Val Ser Pro Pro Ser
            1               5                  10

AAA AAG TCT GAA ACC GAC AAC ATC AAG CGC GTA CCC TGC GAG ACA CCG       216
Lys Lys Ser Glu Thr Asp Asn Ile Lys Arg Val Pro Cys Glu Thr Pro
 15              20                  25

CCC TTC ACT GTC GGA GAA CTC AAG AAA GCA ATC CCA CCG CAC TGT TTC       264
Pro Phe Thr Val Gly Glu Leu Lys Lys Ala Ile Pro Pro His Cys Phe
 30              35                  40                  45

AAA CGC TCG ATC CCT CGC TCT TTC TCC TAC CTC ATC TGG GAC ATC ATC       312
Lys Arg Ser Ile Pro Arg Ser Phe Ser Tyr Leu Ile Trp Asp Ile Ile
             50                  55                  60

ATA GCC TCC TGC TTC TAC TAC GTC GCC ACC ACT TAC TTC CCT CTC CTC       360
Ile Ala Ser Cys Phe Tyr Tyr Val Ala Thr Thr Tyr Phe Pro Leu Leu
             65                  70                  75

CCT CAC CCT CTC TCC TAC TTC GCC TGG CCT CTC TAC TGG GCC TGC CAG       408
Pro His Pro Leu Ser Tyr Phe Ala Trp Pro Leu Tyr Trp Ala Cys Gln
         80                  85                  90

GGC TGC GTC CTA ACC GGC GTC TGG GTC ATA GCC CAC GAG TGC GGC CAC       456
Gly Cys Val Leu Thr Gly Val Trp Val Ile Ala His Glu Cys Gly His
         95                 100                 105

CAC GCC TTC AGC GAC TAC CAG TGG CTG GAC GAC ACC GTC GGC CTC ATC       504
```

```
His Ala Phe Ser Asp Tyr Gln Trp Leu Asp Asp Thr Val Gly Leu Ile
110                 115                 120                 125

TTC CAC TCC TTC CTC CTC GTC CCT TAC TTC TCC TGG AAG TAC AGT CAT          552
Phe His Ser Phe Leu Leu Val Pro Tyr Phe Ser Trp Lys Tyr Ser His
                130                 135                 140

CGA CGC CAC CAT TCC AAC ACT GGC TCC CTC GAG AGA GAC GAA GTG TTT          600
Arg Arg His His Ser Asn Thr Gly Ser Leu Glu Arg Asp Glu Val Phe
            145                 150                 155

GTC CCC AAG AAG AAG TCA GAC ATC AAG TGG TAC GGC AAG TAC CTC AAC          648
Val Pro Lys Lys Lys Ser Asp Ile Lys Trp Tyr Gly Lys Tyr Leu Asn
        160                 165                 170

AAC CCT TTG GGA CGC ACC GTG ATG TTA ACG GTT CAG TTC ACT CTC GGC          696
Asn Pro Leu Gly Arg Thr Val Met Leu Thr Val Gln Phe Thr Leu Gly
    175                 180                 185

TGG CCT TTG TAC TTA GCC TTC AAC GTC TCG GGG AGA CCT TAC GAC GGC          744
Trp Pro Leu Tyr Leu Ala Phe Asn Val Ser Gly Arg Pro Tyr Asp Gly
190                 195                 200                 205

GGC TTC GCT TGC CAT TTC CAC CCC AAC GCT CCC ATC TAC AAC GAC CGT          792
Gly Phe Ala Cys His Phe His Pro Asn Ala Pro Ile Tyr Asn Asp Arg
                210                 215                 220

GAG CGT CTC CAG ATA TAC ATC TCC GAC GCT GGC ATC CTC GCC GTC TGC          840
Glu Arg Leu Gln Ile Tyr Ile Ser Asp Ala Gly Ile Leu Ala Val Cys
            225                 230                 235

TAC GGT CTC TAC CGC TAC GCT GCT GTC CAA GGA GTT GCC TCG ATG GTC          888
Tyr Gly Leu Tyr Arg Tyr Ala Ala Val Gln Gly Val Ala Ser Met Val
        240                 245                 250

TGC TTC TAC GGA GTT CCT CTT CTG ATT GTC AAC GGG TTC TTA GTT TTG          936
Cys Phe Tyr Gly Val Pro Leu Leu Ile Val Asn Gly Phe Leu Val Leu
    255                 260                 265

ATC ACT TAC TTG CAG CAC ACG CAT CCT TCC CTG CCT CAC TAT GAC TCG          984
Ile Thr Tyr Leu Gln His Thr His Pro Ser Leu Pro His Tyr Asp Ser
270                 275                 280                 285

TCT GAG TGG GAT TGG TTG AGG GGA GCT TTG GCC ACC GTT GAC AGA GAC         1032
Ser Glu Trp Asp Trp Leu Arg Gly Ala Leu Ala Thr Val Asp Arg Asp
                290                 295                 300

TAC GGA ATC TTG AAC AAG GTC TTC CAC AAT ATC ACG GAC ACG CAC GTG         1080
Tyr Gly Ile Leu Asn Lys Val Phe His Asn Ile Thr Asp Thr His Val
            305                 310                 315

GCG CAT CAC CTG TTC TCG ACC ATG CCG CAT TAT CAT GCG ATG GAA GCT         1128
Ala His His Leu Phe Ser Thr Met Pro His Tyr His Ala Met Glu Ala
        320                 325                 330

ACG AAG GCG ATA AAG CCG ATA CTG GGA GAG TAT TAT CAG TTC GAT GGG         1176
Thr Lys Ala Ile Lys Pro Ile Leu Gly Glu Tyr Tyr Gln Phe Asp Gly
    335                 340                 345

ACG CCG GTG GTT AAG GCG ATG TGG AGG GAG GCG AAG GAG TGT ATC TAT         1224
Thr Pro Val Val Lys Ala Met Trp Arg Glu Ala Lys Glu Cys Ile Tyr
350                 355                 360                 365

GTG GAA CCG GAC AGG CAA GGT GAG AAG AAA GGT GTG TTC TGG TAC AAC         1272
Val Glu Pro Asp Arg Gln Gly Glu Lys Lys Gly Val Phe Trp Tyr Asn
                370                 375                 380

AAT AAG TTA TGA AGCAAAGAAG AAACTGAACC TTTCTCTTCT ATGATTGTCT             1324
Asn Lys Leu

TTGTTTAAGA AGCTATGTTT CTGTTTCAAT AATCTTAATT ATCCATTTTG TTGTGTTT         1384

TGACATTTTG GCTAAAATTA TGTGATGTTG GAAGTTAGTG TC                          1426

(2) INFORMATION FOR SEQ ID NO: 4:

(i) SEQUENCE CHARACTERISTICS:
        (A) LENGTH: 384 amino acids
```

(B) TYPE: amino acid
        (D) TOPOLOGY: linear (ii) MOLECULE TYPE: protein (xi) SEQUENCE DESCRIPTION: SEQ ID NO: 4:

Met Gly Ala Gly Gly Arg Met Gln Val Ser Pro Ser Lys Lys Ser
 1               5                  10                  15

Glu Thr Asp Asn Ile Lys Arg Val Pro Cys Glu Thr Pro Phe Thr
                 20                  25                  30

Val Gly Glu Leu Lys Lys Ala Ile Pro Pro His Cys Phe Lys Arg Ser
             35                  40                  45

Ile Pro Arg Ser Phe Ser Tyr Leu Ile Trp Asp Ile Ile Ala Ser
     50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
                115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
                195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
370                 375                 380

(2) INFORMATION FOR SEQ ID NO: 5:

(i) SEQUENCE CHARACTERISTICS:
        (A) LENGTH: 1462 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Glycine max (vii) IMMEDIATE SOURCE:
        (B) CLONE: pSF2-165K (ix) FEATURE:
        (A) NAME/KEY: CDS
        (B) LOCATION: 108..1247

(xi) SEQUENCE DESCRIPTION: SEQ ID NO: 5:

```
CCATATACTA ATATTTGCTT GTATTGATAG CCCCTCCGTT CCCAAGAGTA TAAAACTGCA        60

TCGAATAATA CAAGCCACTA GGCATGGGTC TAGCAAAGGA ACAACA ATG GGA GGT          116
                                                Met Gly Gly
                                                  1

AGA GGT CGT GTG GCC AAA GTG GAA GTT CAA GGG AAG AAG CCT CTC TCA         164
Arg Gly Arg Val Ala Lys Val Glu Val Gln Gly Lys Lys Pro Leu Ser
  5              10                  15

AGG GTT CCA AAC ACA AAG CCA CCA TTC ACT GTT GGC CAA CTC AAG AAA         212
Arg Val Pro Asn Thr Lys Pro Pro Phe Thr Val Gly Gln Leu Lys Lys
 20                  25                  30                  35

GCA ATT CCA CCA CAC TGC TTT CAG CGC TCC CTC CTC ACT TCA TTC TCC         260
Ala Ile Pro Pro His Cys Phe Gln Arg Ser Leu Leu Thr Ser Phe Ser
                  40                  45                  50

TAT GTT GTT TAT GAC CTT TCA TTT GCC TTC ATT TTC TAC ATT GCC ACC         308
Tyr Val Val Tyr Asp Leu Ser Phe Ala Phe Ile Phe Tyr Ile Ala Thr
             55                  60                  65

ACC TAC TTC CAC CTC CTT CCT CAA CCC TTT TCC CTC ATT GCA TGG CCA         356
Thr Tyr Phe His Leu Leu Pro Gln Pro Phe Ser Leu Ile Ala Trp Pro
         70                  75                  80

ATC TAT TGG GTT CTC CAA GGT TGC CTT CTC ACT GGT GTG TGG GTG ATT         404
Ile Tyr Trp Val Leu Gln Gly Cys Leu Leu Thr Gly Val Trp Val Ile
 85                  90                  95

GCT CAC GAG TGT GGT CAC CAT GCC TTC AGC AAG TAC CAA TGG GTT GAT         452
Ala His Glu Cys Gly His His Ala Phe Ser Lys Tyr Gln Trp Val Asp
100                 105                 110                 115

GAT GTT GTG GGT TTG ACC CTT CAC TCA ACA CTT TTA GTC CCT TAT TTC         500
Asp Val Val Gly Leu Thr Leu His Ser Thr Leu Leu Val Pro Tyr Phe
                 120                 125                 130

TCA TGG AAA ATA AGC CAT CGC CGC CAT CAC TCC AAC ACA GGT TCC CTT         548
Ser Trp Lys Ile Ser His Arg Arg His His Ser Asn Thr Gly Ser Leu
             135                 140                 145

GAC CGT GAT GAA GTG TTT GTC CCA AAA CCA AAA TCC AAA GTT GCA TGG         596
Asp Arg Asp Glu Val Phe Val Pro Lys Pro Lys Ser Lys Val Ala Trp
         150                 155                 160

TTT TCC AAG TAC TTA AAC AAC CCT CTA GGA AGG GCT GTT TCT CTT CTC         644
Phe Ser Lys Tyr Leu Asn Asn Pro Leu Gly Arg Ala Val Ser Leu Leu
165                 170                 175

GTC ACA CTC ACA ATA GGG TGG CCT ATG TAT TTA GCC TTC AAT GTC TCT         692
Val Thr Leu Thr Ile Gly Trp Pro Met Tyr Leu Ala Phe Asn Val Ser
```

-continued

```
       180                 185                 190                  195
GGT AGA CCC TAT GAT AGT TTT GCA AGC CAC TAC CAC CCT TAT GCT CCC            740
Gly Arg Pro Tyr Asp Ser Phe Ala Ser His Tyr His Pro Tyr Ala Pro
                    200                 205                 210

ATA TAT TCT AAC CGT GAG AGG CTT CTG ATC TAT GTC TCT GAT GTT GCT            788
Ile Tyr Ser Asn Arg Glu Arg Leu Leu Ile Tyr Val Ser Asp Val Ala
                215                 220                 225

TTG TTT TCT GTG ACT TAC TCT CTC TAC CGT GTT GCA ACC CTG AAA GGG            836
Leu Phe Ser Val Thr Tyr Ser Leu Tyr Arg Val Ala Thr Leu Lys Gly
            230                 235                 240

TTG GTT TGG CTG CTA TGT GTT TAT GGG GTG CCT TTG CTC ATT GTG AAC            884
Leu Val Trp Leu Leu Cys Val Tyr Gly Val Pro Leu Leu Ile Val Asn
        245                 250                 255

GGT TTT CTT GTG ACT ATC ACA TAT TTG CAG CAC ACA CAC TTT GCC TTG            932
Gly Phe Leu Val Thr Ile Thr Tyr Leu Gln His Thr His Phe Ala Leu
260                 265                 270                 275

CCT CAT TAC GAT TCA TCA GAA TGG GAC TGG CTG AAG GGA GCT TTG GCA            980
Pro His Tyr Asp Ser Ser Glu Trp Asp Trp Leu Lys Gly Ala Leu Ala
                280                 285                 290

ACT ATG GAC AGA GAT TAT GGG ATT CTG AAC AAG GTG TTT CAT CAC ATA           1028
Thr Met Asp Arg Asp Tyr Gly Ile Leu Asn Lys Val Phe His His Ile
                295                 300                 305

ACT GAT ACT CAT GTG GCT CAC CAT CTC TTC TCT ACA ATG CCA CAT TAC           1076
Thr Asp Thr His Val Ala His His Leu Phe Ser Thr Met Pro His Tyr
            310                 315                 320

CAT GCA ATG GAG GCA ACC AAT GCA ATC AAG CCA ATA TTG GGT GAG TAC           1124
His Ala Met Glu Ala Thr Asn Ala Ile Lys Pro Ile Leu Gly Glu Tyr
325                 330                 335

TAC CAA TTT GAT GAC ACA CCA TTT TAC AAG GCA CTG TGG AGA GAA GCG           1172
Tyr Gln Phe Asp Asp Thr Pro Phe Tyr Lys Ala Leu Trp Arg Glu Ala
340                 345                 350                 355

AGA GAG TGC CTC TAT GTG GAG CCA GAT GAA GGA ACA TCC GAG AAG GGC           1220
Arg Glu Cys Leu Tyr Val Glu Pro Asp Glu Gly Thr Ser Glu Lys Gly
                360                 365                 370

GTG TAT TGG TAC AGG AAC AAG TAT TGATGGAGCA ACCAATGGGC CATAGTGGG           1274
Val Tyr Trp Tyr Arg Asn Lys Tyr
                375                 380

GTTATGGAAG TTTTGTCATG TATTAGTACA TAATTAGTAG AATGTTATAA ATAAGTGG          1334

TTGCCGCGTA ATGACTTTGT GTGTATTGTG AAACAGCTTG TTGCGATCAT GGTTATAA          1394

TAAAAATAAT TCTGGTATTA ATTACATGTG GAAAGTGTTC TGCTTATAGC TTTCTGCC          1454

AAAAAAAA                                                                  1462
```

(2) INFORMATION FOR SEQ ID NO: 6:

(i) SEQUENCE CHARACTERISTICS:
        (A) LENGTH: 379 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Gly Gly Arg Gly Arg Val Ala Lys Val Glu Val Gln Gly Lys Lys
1               5                   10                  15

Pro Leu Ser Arg Val Pro Asn Thr Lys Pro Pro Phe Thr Val Gly Gln
            20                  25                  30

Leu Lys Lys Ala Ile Pro Pro His Cys Phe Gln Arg Ser Leu Leu Thr
        35                  40                  45
```

```
Ser Phe Ser Tyr Val Val Tyr Asp Leu Ser Phe Ala Phe Ile Phe Tyr
         50                  55                  60

Ile Ala Thr Thr Tyr Phe His Leu Leu Pro Gln Pro Phe Ser Leu Ile
 65                  70                  75                  80

Ala Trp Pro Ile Tyr Trp Val Leu Gln Gly Cys Leu Leu Thr Gly Val
                 85                  90                  95

Trp Val Ile Ala His Glu Cys Gly His His Ala Phe Ser Lys Tyr Gln
            100                 105                 110

Trp Val Asp Asp Val Val Gly Leu Thr Leu His Ser Thr Leu Leu Val
            115                 120                 125

Pro Tyr Phe Ser Trp Lys Ile Ser His Arg Arg His His Ser Asn Thr
            130                 135                 140

Gly Ser Leu Asp Arg Asp Glu Val Phe Val Pro Lys Pro Lys Ser Lys
145                 150                 155                 160

Val Ala Trp Phe Ser Lys Tyr Leu Asn Asn Pro Leu Gly Arg Ala Val
                165                 170                 175

Ser Leu Leu Val Thr Leu Thr Ile Gly Trp Pro Met Tyr Leu Ala Phe
            180                 185                 190

Asn Val Ser Gly Arg Pro Tyr Asp Ser Phe Ala Ser His Tyr His Pro
            195                 200                 205

Tyr Ala Pro Ile Tyr Ser Asn Arg Glu Arg Leu Leu Ile Tyr Val Ser
            210                 215                 220

Asp Val Ala Leu Phe Ser Val Thr Tyr Ser Leu Tyr Arg Val Ala Thr
225                 230                 235                 240

Leu Lys Gly Leu Val Trp Leu Leu Cys Val Tyr Gly Val Pro Leu Leu
                245                 250                 255

Ile Val Asn Gly Phe Leu Val Thr Ile Thr Tyr Leu Gln His Thr His
            260                 265                 270

Phe Ala Leu Pro His Tyr Asp Ser Ser Glu Trp Asp Trp Leu Lys Gly
            275                 280                 285

Ala Leu Ala Thr Met Asp Arg Asp Tyr Gly Ile Leu Asn Lys Val Phe
290                 295                 300

His His Ile Thr Asp Thr His Val Ala His His Leu Phe Ser Thr Met
305                 310                 315                 320

Pro His Tyr His Ala Met Glu Ala Thr Asn Ala Ile Lys Pro Ile Leu
                325                 330                 335

Gly Glu Tyr Tyr Gln Phe Asp Asp Thr Pro Phe Tyr Lys Ala Leu Trp
            340                 345                 350

Arg Glu Ala Arg Glu Cys Leu Tyr Val Glu Pro Asp Glu Gly Thr Ser
            355                 360                 365

Glu Lys Gly Val Tyr Trp Tyr Arg Asn Lys Tyr
370                 375

(2) INFORMATION FOR SEQ ID NO: 7:

(i) SEQUENCE CHARACTERISTICS:
        (A) LENGTH: 1790 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
```

(A) ORGANISM: Zea mays (vii) IMMEDIATE SOURCE:
   (B) CLONE: pFad2#1

(ix) FEATURE:
   (A) NAME/KEY: CDS
   (B) LOCATION: 165..1328

(xi) SEQUENCE DESCRIPTION: SEQ ID NO: 7:

```
CGGCCTCTCC CCTCCCTCCT CCCTGCAAAT CCTGCAGACA CCACCGCTCG TTTTTCTCTC        60

CGGGACAGGA GAAAAGGGGA GAGAGAGGTG AGGCGCGGTG TCCGCCCGAT CTGCTCTGC        120

CCGACGCAGC TGTTACGACC TCCTCAGTCT CAGTCAGGAG CAAG ATG GGT GCC GGC        176
                                                 Met Gly Ala Gly
                                                  1

GGC AGG ATG ACC GAG AAG GAG CGG GAG AAG CAG GAG CAG CTC GCC CGA        224
Gly Arg Met Thr Glu Lys Glu Arg Glu Lys Gln Glu Gln Leu Ala Arg
 5              10                  15                  20

GCT ACC GGT GGC GCC GCG ATG CAG CGG TCG CCG GTG GAG AAG CCT CCG        272
Ala Thr Gly Gly Ala Ala Met Gln Arg Ser Pro Val Glu Lys Pro Pro
             25                  30                  35

TTC ACT CTG GGT CAG ATC AAG AAG GCC ATC CCG CCA CAC TGC TTC GAG        320
Phe Thr Leu Gly Gln Ile Lys Lys Ala Ile Pro Pro His Cys Phe Glu
         40                  45                  50

CGC TCG GTG CTC AAG TCC TTC TCG TAC GTG GTC CAC GAC CTG GTG ATC        368
Arg Ser Val Leu Lys Ser Phe Ser Tyr Val Val His Asp Leu Val Ile
     55                  60                  65

GCC GCG GCG CTC CTC TAC TTC GCG CTG GCC ATC ATA CCG GCG CTC CCA        416
Ala Ala Ala Leu Leu Tyr Phe Ala Leu Ala Ile Ile Pro Ala Leu Pro
 70                  75                  80

AGC CCG CTC CGC TAC GCC GCC TGG CCG CTG TAC TGG ATC GCG CAG GGG        464
Ser Pro Leu Arg Tyr Ala Ala Trp Pro Leu Tyr Trp Ile Ala Gln Gly
 85                  90                  95                 100

TGC GTG TGC ACC GGC GTG TGG GTC ATC GCG CAC GAG TGC GGC CAC CAC        512
Cys Val Cys Thr Gly Val Trp Val Ile Ala His Glu Cys Gly His His
                105                 110                 115

GCC TTC TCG GAC TAC TCG CTC CTG GAC GAC GTG GTC GGC CTG GTG CTG        560
Ala Phe Ser Asp Tyr Ser Leu Leu Asp Asp Val Val Gly Leu Val Leu
                120                 125                 130

CAC TCG TCG CTC ATG GTG CCC TAC TTC TCG TGG AAG TAC AGC CAC CGG        608
His Ser Ser Leu Met Val Pro Tyr Phe Ser Trp Lys Tyr Ser His Arg
        135                 140                 145

CGC CAC CAC TCC AAC ACG GGG TCC CTG GAG CGC GAC GAG GTG TTC GTG        656
Arg His His Ser Asn Thr Gly Ser Leu Glu Arg Asp Glu Val Phe Val
    150                 155                 160

CCC AAG AAG AAG GAG GCG CTG CCG TGG TAC ACC CCG TAC GTG TAC AAC        704
Pro Lys Lys Lys Glu Ala Leu Pro Trp Tyr Thr Pro Tyr Val Tyr Asn
165                 170                 175                 180

AAC CCG GTC GGC CGG GTG GTG CAC ATC GTG GTG CAG CTC ACC CTC GGG        752
Asn Pro Val Gly Arg Val Val His Ile Val Val Gln Leu Thr Leu Gly
                185                 190                 195

TGG CCG CTG TAC CTG GCG ACC AAC GCG TCG GGG CGG CCG TAC CCG CGC        800
Trp Pro Leu Tyr Leu Ala Thr Asn Ala Ser Gly Arg Pro Tyr Pro Arg
                200                 205                 210

TTC GCC TGC CAC TTC GAC CCC TAC GGC CCC ATC TAC AAC GAC CGG GAG        848
Phe Ala Cys His Phe Asp Pro Tyr Gly Pro Ile Tyr Asn Asp Arg Glu
            215                 220                 225

CGC GCC CAG ATC TTC GTC TCG GAC GCC GGC GTC GTG GCC GTG GCG TTC        896
Arg Ala Gln Ile Phe Val Ser Asp Ala Gly Val Val Ala Val Ala Phe
        230                 235                 240
```

```
GGG CTG TAC AAG CTG GCG GCG GCG TTC GGG GTC TGG TGG GTG GTG CGC      944
Gly Leu Tyr Lys Leu Ala Ala Ala Phe Gly Val Trp Trp Val Val Arg
245                 250                 255                 260

GTG TAC GCC GTG CCG CTG CTG ATC GTG AAC GCG TGG CTG GTG CTC ATC      992
Val Tyr Ala Val Pro Leu Leu Ile Val Asn Ala Trp Leu Val Leu Ile
                265                 270                 275

ACC TAC CTG CAG CAC ACC CAC CCG TCG CTC CCC CAC TAC GAC TCG AGC     1040
Thr Tyr Leu Gln His Thr His Pro Ser Leu Pro His Tyr Asp Ser Ser
            280                 285                 290

GAG TGG GAC TGG CTG CGC GGC GCG CTG GCC ACC ATG GAC CGC GAC TAC     1088
Glu Trp Asp Trp Leu Arg Gly Ala Leu Ala Thr Met Asp Arg Asp Tyr
        295                 300                 305

GGC ATC CTC AAC CGC GTG TTC CAC AAC ATC ACG GAC ACG CAC GTC GCG     1136
Gly Ile Leu Asn Arg Val Phe His Asn Ile Thr Asp Thr His Val Ala
    310                 315                 320

CAC CAC CTC TTC TCC ACC ATG CCG CAC TAC CAC GCC ATG GAG GCC ACC     1184
His His Leu Phe Ser Thr Met Pro His Tyr His Ala Met Glu Ala Thr
325                 330                 335                 340

AAG GCG ATC AGG CCC ATC CTC GGC GAC TAC TAC CAC TTC GAC CCG ACC     1232
Lys Ala Ile Arg Pro Ile Leu Gly Asp Tyr Tyr His Phe Asp Pro Thr
                345                 350                 355

CCT GTC GCC AAG GCG ACC TGG CGC GAG GCC GGG GAA TGC ATC TAC GTC     1280
Pro Val Ala Lys Ala Thr Trp Arg Glu Ala Gly Glu Cys Ile Tyr Val
            360                 365                 370

GAG CCC GAG GAC CGC AAG GGC GTC TTC TGG TAC AAC AAG AAG TTC TAG     1335
Glu Pro Glu Asp Arg Lys Gly Val Phe Trp Tyr Asn Lys Lys Phe
        375                 380                 385

CGCTCGCAGA GCTGAGGACG CTACCGTAGG AATGGGAGCA GAAACCAGGA GGAGGAGA     1395

GTACTCGCCC CAAAGTCTCC GTCAACCTAT CTAATCGTTA GTCGTCAGTC TTTTAGAC     1455

GAAGAGAGAT CATTTGGGCA CAGAGACGAA GGCTTACTGC AGTGCCATCG CTAGAGCT     1515

CATCAAGTAC AAGTAGGCAA ATTCGTCAAC TTAGTGTGTC CCATGTTGTT TTTCTTAG     1575

GTCCGCTGCT GTAGGCTTTC CGGCGGCGGT CGTTTGTGTG GTTGGCATCC GTGGCCAT     1635

CTGTGCGTGC GTGGCCGCGC TTGTCGTGTG CGTCTGTCGT CGCGTTGGCG TCGTCTCT     1695

GTGCTCCCCG TGTGTTGTTG TAAAACAAGA AGATGTTTTC TGGTGTCTTT GGCGGAAT     1755

CAGATCGTCC GAACGAAAAA AAAAAAAAAA AAAA                               1790

(2) INFORMATION FOR SEQ ID NO: 8:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO: 8:

Met Gly Ala Gly Gly Arg Met Thr Glu Lys Glu Arg Glu Lys Gln Glu
1               5                   10                  15

Gln Leu Ala Arg Ala Thr Gly Gly Ala Ala Met Gln Arg Ser Pro Val
            20                  25                  30

Glu Lys Pro Pro Phe Thr Leu Gly Gln Ile Lys Lys Ala Ile Pro Pro
        35                  40                  45

His Cys Phe Glu Arg Ser Val Leu Lys Ser Phe Ser Tyr Val Val His
    50                  55                  60

Asp Leu Val Ile Ala Ala Ala Leu Leu Tyr Phe Ala Leu Ala Ile Ile
65                  70                  75                  80
```

-continued

```
Pro Ala Leu Pro Ser Pro Leu Arg Tyr Ala Ala Trp Pro Leu Tyr Trp
                85                  90                  95
Ile Ala Gln Gly Cys Val Cys Thr Gly Val Trp Val Ile Ala His Glu
            100                 105                 110
Cys Gly His His Ala Phe Ser Asp Tyr Ser Leu Leu Asp Asp Val Val
        115                 120                 125
Gly Leu Val Leu His Ser Ser Leu Met Val Pro Tyr Phe Ser Trp Lys
    130                 135                 140
Tyr Ser His Arg Arg His His Ser Asn Thr Gly Ser Leu Glu Arg Asp
145                 150                 155                 160
Glu Val Phe Val Pro Lys Lys Glu Ala Leu Pro Trp Tyr Thr Pro
                165                 170                 175
Tyr Val Tyr Asn Asn Pro Val Gly Arg Val Val His Ile Val Val Gln
            180                 185                 190
Leu Thr Leu Gly Trp Pro Leu Tyr Leu Ala Thr Asn Ala Ser Gly Arg
        195                 200                 205
Pro Tyr Pro Arg Phe Ala Cys His Phe Asp Pro Tyr Gly Pro Ile Tyr
    210                 215                 220
Asn Asp Arg Glu Arg Ala Gln Ile Phe Val Ser Asp Ala Gly Val Val
225                 230                 235                 240
Ala Val Ala Phe Gly Leu Tyr Lys Leu Ala Ala Ala Phe Gly Val Trp
                245                 250                 255
Trp Val Val Arg Val Tyr Ala Val Pro Leu Leu Ile Val Asn Ala Trp
            260                 265                 270
Leu Val Leu Ile Thr Tyr Leu Gln His Thr His Pro Ser Leu Pro His
        275                 280                 285
Tyr Asp Ser Ser Glu Trp Asp Trp Leu Arg Gly Ala Leu Ala Thr Met
    290                 295                 300
Asp Arg Asp Tyr Gly Ile Leu Asn Arg Val Phe His Asn Ile Thr Asp
305                 310                 315                 320
Thr His Val Ala His His Leu Phe Ser Thr Met Pro His Tyr His Ala
                325                 330                 335
Met Glu Ala Thr Lys Ala Ile Arg Pro Ile Leu Gly Asp Tyr Tyr His
            340                 345                 350
Phe Asp Pro Thr Pro Val Ala Lys Ala Thr Trp Arg Glu Ala Gly Glu
        355                 360                 365
Cys Ile Tyr Val Glu Pro Glu Asp Arg Lys Gly Val Phe Trp Tyr Asn
    370                 375                 380
Lys Lys Phe
385

(2) INFORMATION FOR SEQ ID NO: 9:

(i) SEQUENCE CHARACTERISTICS:
        (A) LENGTH: 673 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Ricinus communis (vii) IMMEDIATE SOURCE:
```

(B) CLONE: pRF2-1C (ix) FEATURE:
              (A) NAME/KEY: CDS
              (B) LOCATION: 1..673

(xi) SEQUENCE DESCRIPTION: SEQ ID NO: 9:

```
TGG GTG ATG GCG CAT GAT TGT GGG CAC CAT GCC TTC AGT GAC TAT CAA      48
Trp Val Met Ala His Asp Cys Gly His His Ala Phe Ser Asp Tyr Gln
  1               5                  10                  15

TTG CTT GAT GAT GTA GTT GGT CTT ATC CTA CAC TCC TGT CTC CTT GTC      96
Leu Leu Asp Asp Val Val Gly Leu Ile Leu His Ser Cys Leu Leu Val
                 20                  25                  30

CCT TAT TTT TCA TGG AAA CAC AGC CAT CGC CGA CAT CAT TCC AAC ACA     144
Pro Tyr Phe Ser Trp Lys His Ser His Arg Arg His His Ser Asn Thr
             35                  40                  45

GGG TCC CTG GAA CGG GAT GAA GTG TTT GTT CCC AAG AAG AAA TCT AGT     192
Gly Ser Leu Glu Arg Asp Glu Val Phe Val Pro Lys Lys Lys Ser Ser
 50                  55                  60

ATC CGT TGG TAT TCC AAA TAC CTC AAC AAC CCT CCA GGT CGT ATC ATG     240
Ile Arg Trp Tyr Ser Lys Tyr Leu Asn Asn Pro Pro Gly Arg Ile Met
 65                  70                  75                  80

ACA ATT GCC GTC ACA CTT TCA CTT GGC TGG CCT CTG TAC CTA GCA TTC     288
Thr Ile Ala Val Thr Leu Ser Leu Gly Trp Pro Leu Tyr Leu Ala Phe
                 85                  90                  95

AAT GTT TCA GGC AGG CCA TAT GAT CGG TTC GCC TGC CAC TAT GAC CCA     336
Asn Val Ser Gly Arg Pro Tyr Asp Arg Phe Ala Cys His Tyr Asp Pro
            100                 105                 110

TAT GGC CCG ATC TAC AAT GAT CGC GAG CGA ATC GAG ATA TTC ATA TCA     384
Tyr Gly Pro Ile Tyr Asn Asp Arg Glu Arg Ile Glu Ile Phe Ile Ser
            115                 120                 125

GAT GCT GGT GTT CTT GCT GTC ACT TTT GGT CTC TAC CAA CTT GCT ATA     432
Asp Ala Gly Val Leu Ala Val Thr Phe Gly Leu Tyr Gln Leu Ala Ile
130                 135                 140

GCG AAG GGG CTT GCT TGG GTT GTC TGT GTA TAT GGA GTG CCA TTG TTG     480
Ala Lys Gly Leu Ala Trp Val Val Cys Val Tyr Gly Val Pro Leu Leu
145                 150                 155                 160

GTG GTG AAT TCA TTC CTT GTT CTG ATC ACA TTT CTG CAG CAT ACT CAC     528
Val Val Asn Ser Phe Leu Val Leu Ile Thr Phe Leu Gln His Thr His
                165                 170                 175

CCT GCA TTG CCA CAT TAT GAT TCG TCG GAG TGG GAC TGG CTA AGA GGA     576
Pro Ala Leu Pro His Tyr Asp Ser Ser Glu Trp Asp Trp Leu Arg Gly
            180                 185                 190

GCT CTA GCA ACT GTT GAC AGA GAT TAC GGG ATC TTG AAC AAG GTG TTC     624
Ala Leu Ala Thr Val Asp Arg Asp Tyr Gly Ile Leu Asn Lys Val Phe
            195                 200                 205

CAT AAC ATA ACG GAC ACT CAA GTA GCT CAC CAC CTT TTC ACC ATG CCC     673
His Asn Ile Thr Asp Thr Gln Val Ala His His Leu Phe Thr Met Pro
            210                 215                 220
```

(2) INFORMATION FOR SEQ ID NO: 10:

(i) SEQUENCE CHARACTERISTICS:
         (A) LENGTH: 224 amino acids
         (B) TYPE: amino acid
         (D) TOPOLOGY: linear (ii) MOLECULE TYPE: protein (xi) SEQUENCE DESCRIPTION: SEQ ID NO: 10:

```
Trp Val Met Ala His Asp Cys Gly His His Ala Phe Ser Asp Tyr Gln
  1               5                  10                  15
```

```
Leu Leu Asp Asp Val Val Gly Leu Ile Leu His Ser Cys Leu Leu Val
            20                  25                  30

Pro Tyr Phe Ser Trp Lys His Ser His Arg Arg His His Ser Asn Thr
        35                  40                  45

Gly Ser Leu Glu Arg Asp Glu Val Phe Val Pro Lys Lys Lys Ser Ser
    50                  55                  60

Ile Arg Trp Tyr Ser Lys Tyr Leu Asn Asn Pro Pro Gly Arg Ile Met
65                  70                  75                  80

Thr Ile Ala Val Thr Leu Ser Leu Gly Trp Pro Leu Tyr Leu Ala Phe
                85                  90                  95

Asn Val Ser Gly Arg Pro Tyr Asp Arg Phe Ala Cys His Tyr Asp Pro
                100                 105                 110

Tyr Gly Pro Ile Tyr Asn Asp Arg Glu Arg Ile Glu Ile Phe Ile Ser
            115                 120                 125

Asp Ala Gly Val Leu Ala Val Thr Phe Gly Leu Tyr Gln Leu Ala Ile
        130                 135                 140

Ala Lys Gly Leu Ala Trp Val Val Cys Val Tyr Gly Val Pro Leu Leu
145                 150                 155                 160

Val Val Asn Ser Phe Leu Val Leu Ile Thr Phe Leu Gln His Thr His
                165                 170                 175

Pro Ala Leu Pro His Tyr Asp Ser Ser Glu Trp Asp Trp Leu Arg Gly
            180                 185                 190

Ala Leu Ala Thr Val Asp Arg Asp Tyr Gly Ile Leu Asn Lys Val Phe
        195                 200                 205

His Asn Ile Thr Asp Thr Gln Val Ala His His Leu Phe Thr Met Pro
    210                 215                 220

(2) INFORMATION FOR SEQ ID NO: 11:

(i) SEQUENCE CHARACTERISTICS:
        (A) LENGTH: 1369 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Ricinus communis (vii) IMMEDIATE SOURCE:
        (B) CLONE: pRF197c-42

(ix) FEATURE:
        (A) NAME/KEY: CDS
        (B) LOCATION: 184..1347

(xi) SEQUENCE DESCRIPTION: SEQ ID NO: 11:

CGGCCGGGAT TCCGGTTTTC ACACTAATTT GCAAAAAATG CATGATTTCA CCTCAAATCA        60

AACACCACAC CTTATAACTT AGTCTTAAGA GAGAGAGAGA GAGGAGACAT TTCTCTTCT       120

TGAGATGAGC ACTTCTCTTC CAGACATCGA AGCCTCAGGA AAGTGCTTGA GAAGAGCTT       180

AGA ATG GGA GGT GGT GGT CGC ATG TCT ACT GTC ATA ATC AGC AAC AAC       228
    Met Gly Gly Gly Gly Arg Met Ser Thr Val Ile Ile Ser Asn Asn
    1               5                   10                  15

AGT GAG AAG AAA GGA GGA AGC AGC CAC CTG GAG CGA GCG CCG CAC ACG       276
Ser Glu Lys Lys Gly Gly Ser Ser His Leu Glu Arg Ala Pro His Thr
            20                  25                  30
```

-continued

| | | |
|---|---|---|
| AAG CCT CCT TAC ACA CTT GGT AAC CTC AAG AGA GCC ATC CCA CCC CAT<br>Lys Pro Pro Tyr Thr Leu Gly Asn Leu Lys Arg Ala Ile Pro Pro His<br>35              40              45 | | 324 |
| TGC TTT GAA CGC TCT TTT GTG CGC TCA TTC TCC AAT TTT GCC TAT AAT<br>Cys Phe Glu Arg Ser Phe Val Arg Ser Phe Ser Asn Phe Ala Tyr Asn<br>    50              55              60 | | 372 |
| TTC TGC TTA AGT TTT CTT TCC TAC TCG ATC GCC ACC AAC TTC TTC CCT<br>Phe Cys Leu Ser Phe Leu Ser Tyr Ser Ile Ala Thr Asn Phe Phe Pro<br>65              70              75 | | 420 |
| TAC ATC TCT TCT CCG CTC TCG TAT GTC GCT TGG CTG GTT TAC TGG CTC<br>Tyr Ile Ser Ser Pro Leu Ser Tyr Val Ala Trp Leu Val Tyr Trp Leu<br>80              85              90              95 | | 468 |
| TTC CAA GGC TGC ATT CTC ACT GGT CTT TGG GTC ATC GGC CAT GAA TGT<br>Phe Gln Gly Cys Ile Leu Thr Gly Leu Trp Val Ile Gly His Glu Cys<br>        100             105             110 | | 516 |
| GGC CAT CAT GCT TTT AGT GAG TAT CAG CTG GCT GAT GAC ATT GTT GGC<br>Gly His His Ala Phe Ser Glu Tyr Gln Leu Ala Asp Asp Ile Val Gly<br>    115             120             125 | | 564 |
| CTA ATT GTC CAT TCT GCA CTT CTG GTT CCA TAT TTT TCA TGG AAA TAT<br>Leu Ile Val His Ser Ala Leu Leu Val Pro Tyr Phe Ser Trp Lys Tyr<br>130             135             140 | | 612 |
| AGC CAT CGC CGC CAC CAT TCT AAC ATA GGA TCT CTC GAG CGA GAC GAA<br>Ser His Arg Arg His His Ser Asn Ile Gly Ser Leu Glu Arg Asp Glu<br>145             150             155 | | 660 |
| GTG TTC GTC CCG AAA TCA AAG TCG AAA ATT TCA TGG TAT TCT AAG TAC<br>Val Phe Val Pro Lys Ser Lys Ser Lys Ile Ser Trp Tyr Ser Lys Tyr<br>160             165             170             175 | | 708 |
| TTA AAC AAC CCG CCA GGT CGA GTT TTG ACA CTT GCT GCC ACG CTC CTC<br>Leu Asn Asn Pro Pro Gly Arg Val Leu Thr Leu Ala Ala Thr Leu Leu<br>        180             185             190 | | 756 |
| CTT GGC TGG CCT TTA TAT TTA GCT TTC AAT GTC TCT GGT AGA CCT TAC<br>Leu Gly Trp Pro Leu Tyr Leu Ala Phe Asn Val Ser Gly Arg Pro Tyr<br>    195             200             205 | | 804 |
| GAT CGC TTT GCT TGC CAT TAT GAT CCC TAT GGC CCA ATA TTT TCC GAA<br>Asp Arg Phe Ala Cys His Tyr Asp Pro Tyr Gly Pro Ile Phe Ser Glu<br>210             215             220 | | 852 |
| AGA GAA AGG CTT CAG ATT TAC ATT GCT GAC CTC GGA ATC TTT GCC ACA<br>Arg Glu Arg Leu Gln Ile Tyr Ile Ala Asp Leu Gly Ile Phe Ala Thr<br>225             230             235 | | 900 |
| ACG TTT GTG CTT TAT CAG GCT ACA ATG GCA AAA GGG TTG GCT TGG GTA<br>Thr Phe Val Leu Tyr Gln Ala Thr Met Ala Lys Gly Leu Ala Trp Val<br>240             245             250             255 | | 948 |
| ATG CGT ATC TAT GGG GTG CCA TTG CTT ATT GTT AAC TGT TTC CTT GTT<br>Met Arg Ile Tyr Gly Val Pro Leu Leu Ile Val Asn Cys Phe Leu Val<br>        260             265             270 | | 996 |
| ATG ATC ACA TAC TTG CAG CAC ACT CAC CCA GCT ATT CCA CGC TAT GGC<br>Met Ile Thr Tyr Leu Gln His Thr His Pro Ala Ile Pro Arg Tyr Gly<br>    275             280             285 | | 1044 |
| TCA TCG GAA TGG GAT TGG CTC CGG GGA GCA ATG GTG ACT GTC GAT AGA<br>Ser Ser Glu Trp Asp Trp Leu Arg Gly Ala Met Val Thr Val Asp Arg<br>290             295             300 | | 1092 |
| GAT TAT GGG GTG TTG AAT AAA GTA TTC CAT AAC ATT GCA GAC ACT CAT<br>Asp Tyr Gly Val Leu Asn Lys Val Phe His Asn Ile Ala Asp Thr His<br>305             310             315 | | 1140 |
| GTA GCT CAT CAT CTC TTT GCT ACA GTG CCA CAT TAC CAT GCA ATG GAG<br>Val Ala His His Leu Phe Ala Thr Val Pro His Tyr His Ala Met Glu<br>320             325             330             335 | | 1188 |
| GCC ACT AAA GCA ATC AAG CCT ATA ATG GGT GAG TAT TAC CGG TAT GAT<br>Ala Thr Lys Ala Ile Lys Pro Ile Met Gly Glu Tyr Tyr Arg Tyr Asp | | 1236 |

```
                      340               345                350
GGT ACC CCA TTT TAC AAG GCA TTG TGG AGG GAG GCA AAG GAG TGC TTG       1284
Gly Thr Pro Phe Tyr Lys Ala Leu Trp Arg Glu Ala Lys Glu Cys Leu
            355                 360                 365

TTC GTC GAG CCA GAT GAA GGA GCT CCT ACA CAA GGC GTT TTC TGG TAC       1332
Phe Val Glu Pro Asp Glu Gly Ala Pro Thr Gln Gly Val Phe Trp Tyr
        370                 375                 380

CGG AAC AAG TAT TAAAAAAGTG TCATGTAGCC TGCCG                           1369
Arg Asn Lys Tyr
    385
```

(2) INFORMATION FOR SEQ ID NO: 12:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Gly Gly Gly Arg Met Ser Thr Val Ile Ile Ser Asn Asn Ser
 1               5                  10                  15

Glu Lys Lys Gly Gly Ser Ser His Leu Glu Arg Ala Pro His Thr Lys
            20                  25                  30

Pro Pro Tyr Thr Leu Gly Asn Leu Lys Arg Ala Ile Pro Pro His Cys
        35                  40                  45

Phe Glu Arg Ser Phe Val Arg Ser Phe Ser Asn Phe Ala Tyr Asn Phe
    50                  55                  60

Cys Leu Ser Phe Leu Ser Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Leu
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285
```

```
Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
                340                 345                 350

Thr Pro Phe Tyr Lys Ala Leu Trp Arg Glu Ala Lys Glu Cys Leu Phe
            355                 360                 365

Val Glu Pro Asp Glu Gly Ala Pro Thr Gln Gly Val Phe Trp Tyr Arg
    370                 375                 380

Asn Lys Tyr
385

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY:  misc_feature
        (B) LOCATION:  1..23
        (D) OTHER INFORMATION: /product=
            "synthetic
            oligonucleotide"

(xi) SEQUENCE DESCRIPTION: SEQ ID NO: 13:

TGGGTATGCC AYGANTGYGG NCA                                              23

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY:  misc_feature
        (B) LOCATION:  1..22
        (D) OTHER INFORMATION: /product=
            "synthetic
            oligonucleotide"

(xi) SEQUENCE DESCRIPTION: SEQ ID NO: 14:

AAAARTGRTGG CACRTGNGTR TC                                              22

(2) INFORMATION FOR SEQ ID NO: 15:

(i) SEQUENCE CHARACTERISTICS:
        (A) LENGTH: 2973 base pairs
```

```
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pAGF2-6

(ix) FEATURE:
        (A) NAME/KEY: exon
        (B) LOCATION: 433..520

(ix) FEATURE:
        (A) NAME/KEY: intron
        (B) LOCATION: 521..1654

(xi) SEQUENCE DESCRIPTION: SEQ ID NO: 15:

ATTCGGTAAT TCCTACATAT TTTAGAGATT AGTTTGAGTT TCCATCCATA CTTTACTAGT      60

GATTATAAAT TTAAAATACG TACTTTTCGA CTATAAAGTG AAACTAAGTA AATTAGAACG     120

TGATATTAAA AAGTTAATGT TCACTGTTAT ATTTTTTTCA CAAGTAAAAA ATGGGTTATT     180

TGCGGTAAAT AAAAATACCA GATATTTTGA ATTGATTAAA AAGGTTGAAA TAAGAGAGGA     240

GGGGAAAGAA AAGAAGGTGG GGGCCCAGTA TGAAAGGGAA AGGTGTCATC AAATCATCTC     300

TCTCTCTCTC TACCTTCGAC CCACGGGCCG TGTCCATTTA AAGCCCTGTC TCTTGCCATT     360

CCCCATCTGA CCACCAGAAG AAGAGCCACA CACTCACAAA TTAAAAAGAG AGAGAGAGAG     420

AGAGAGACAG AGAGAGAGAG AGATTCTGCG GAGGAGCTTC TTCTTCGTAG GGTGTTCATC     480

GTTATTAACG TTATCGCCCC TACGTCAGCT CCATCTCCAG GTCCGTCGCT TCTCTTCCAT     540

TTCTTCTCAT TTTCGATTTT GATTCTTATT TCTTTCCAGT AGCTCCTGCT CTGTGAATTT     600

CTCCGCTCAC GATAGATCTG CTTATACTCC TTACATTCAA CCTTAGATCT GGTCTCGATT     660

CTCTGTTTCT CTGTTTTTTT CTTTTGGTCG AGAATCTGAT GTTTGTTTAT GTTCTGTCAC     720

CATTAATAAT GATGAACTCT CTCATTCATA CAATGATTAG TTTCTCTCGT CTACCAAACG     780

ATATGTTGCA TTTTCACTTT TCTTCTTTTT TTCTAAGATG ATTTGCTTTG ACCAATTTGT     840

TTAGATCTTT ATTTTATTTT ATTTTCTGGT GGGTTGGTGG AAATTGAAAA AAAAAAAAAA     900

AAAAGCATAA ATTGTTATTT GTTAATGTAT TCATTTTTTG GCTATTTGTT CTGGGTAAAA     960

ATCTGCTTCT ACTGTTGAAT CTTTCCTGGA TTTTTTACTC CTATTGGGTT TTTATAGTAA    1020

AAATACATAA TAAAAGGAAA ACAAAAGTTT TATAGATTCT CTTAAACCCC TTACGATAAA    1080

AGTTGGAATC AAAATAATTC AGGATCAGAT GCTCTTTGAT TGATTCAGAT GCGATTACAG    1140

TTGCATGGAA AATTTTCTAG ATCCGTCGTC ACATTTTATT TTCTGTTTAA ATATCTAAAT    1200

CTGATATATG ATGTCGACAA ATTCTGGTGG CTTATACATC ACTTCAACTG TTTTCTTTTG    1260

GCTTTGTTTG TCAACTTGGT TTTCAATACG ATTTGTGATT TCGATCGCTG AATTTTTAAT    1320

ACAAGCAAAC TGATGTTAAC CACAAGCAAG AGATGTGACC TGCCTTATTA ACATCGTATT    1380

ACTTACTACT AGTCGTATTC TCAACGCAAT CGTTTTTGTA TTTCTCACAT TATGCCGCTT    1440

CTCTACTCTT TATTCCTTTT GGTCCACGCA TTTTCTATTT GTGGCAATCC CTTTCACAAC    1500

CTGATTTCCC ACTTTGGATC ATTTGTCTGA AGACTCTCTT GAATCGTTAC CACTTGTTTC    1560

TTGTGCATGC TCTGTTTTTT AGAATTAATG ATAAAACTAT TCCATAGTCT TGAGTTTTCA    1620
```

```
GCTTGTTGAT TCTTTTGCTT TTGGTTTTCT GCAGAAACAT GGGTGCAGGT GGAAGAATGC      1680

CGGTTCCTAC TTCTTCCAAG AAATCGGAAA CCGACACCAC AAAGCGTGTG CCGTGCGAGA      1740

AACCGCCTTT CTCGGTGGGA GATCTGAAGA AAGCAATCCC GCCGCATTGT TTCAAACGCT      1800

CAATCCCTCG CTCTTTCTCC TACCTTATCA GTGACATCAT TATAGCCTCA TGCTTCTACT      1860

ACGTCGCCAC CAATTACTTC TCTCTCCTCC CTCAGCCTCT CTCTTACTTG GCTTGGCCAC      1920

TCTATTGGGC CTGTCAAGGC TGTGTCCTAA CTGGTATCTG GGTCATAGCC CACGAATGCG      1980

GTCACCACGC ATTCAGCGAC TACCAATGGC TGGATGACAC AGTTGGTCTT ATCTTCCATT      2040

CCTTCCTCCT CGTCCCTTAC TTCTCCTGGA AGTATAGTCA TCGCCGTCAC CATTCCAACA      2100

CTGGATCCCT CGAAAGAGAT GAAGTATTTG TCCCAAAGCA GAAATCAGCA ATCAAGTGGT      2160

ACGGGAAATA CCTCAACAAC CCTCTTGGAC GCATCATGAT GTTAACCGTC CAGTTTGTCC      2220

TCGGGTGGCC CTTGTACTTA GCCTTTAACG TCTCTGGCAG ACCGTATGAC GGGTTCGCTT      2280

GCCATTTCTT CCCCAACGCT CCCATCTACA ATGACCGAGA ACGCCTCCAG ATATACCTCT      2340

CTGATGCGGG TATTCTAGCC GTCTGTTTTG GTCTTTACCG TTACGCTGCT GCACAAGGGA      2400

TGGCCTCGAT GATCTGCCTC TACGGAGTAC CGCTTCTGAT AGTGAATGCG TTCCTCGTCT      2460

TGATCACTTA CTTGCAGCAC ACTCATCCCT CGTTGCCTCA CTACGATTCA TCAGAGTGGG      2520

ACTGGCTCAG GGGAGCTTTG GCTACCGTAG ACAGAGACTA CGGAATCTTG AACAAGGTGT      2580

TCCACAACAT TACAGACACA CACGTGGCTC ATCACCTGTT CTCGACAATG CCGCATTATA      2640

ACGCAATGGA AGCTACAAAG GCGATAAAGC CAATTCTGGG AGACTATTAC CAGTTCGATG      2700

GAACACCGTG GTATGTGGCG ATGTATAGGG AGGCAAAGGA GTGTATCTAT GTAGAACCGG      2760

ACAGGGAAGG TGACAAGAAA GGTGTGTACT GGTACAACAA TAAGTTATGA GGATGATGGT      2820

GAAGAAATTG TCGACTTTTC TCTTGTCTGT TTGTCTTTTG TTAAAGAAGC TATGCTTCGT      2880

TTTAATAATC TTATTGTCCA TTTTGTTGTG TTATGACATT TTGGCTGCTC ATTATGTTAT      2940

GTGGGAAGTT AGCGTTCAAA TGTTTTGGGT CGG                                  2973

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY:  misc_feature
        (B) LOCATION:  1..23
        (D) OTHER INFORMATION: /product=
            "synthetic
            oligonucleotide"

(xi) SEQUENCE DESCRIPTION: SEQ ID NO: 16:

GGGCATGTNG ARAANARRTG RTG                                              23

(2) INFORMATION FOR SEQ ID NO: 17:

(i) SEQUENCE CHARACTERISTICS:
        (A) LENGTH: 23 base pairs
        (B) TYPE: nucleic acid
```

```
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY:  misc_feature
            (B) LOCATION:  1..23
            (D) OTHER INFORMATION: /product=
                "synthetic
                oligonucleotide"

(xi) SEQUENCE DESCRIPTION: SEQ ID NO: 17:

GGGCATGTRC TRAANARRTG RTG                                              23
```

GENES FOR MICROSOMAL DELTA-12 FATTY ACID DESATURASES AND HYDROXYLASES FROM PLANTS

This is a continuation of application Ser. No. 08/262,401 filed Jun. 20, 1994, now abandoned, which is a national filing continuation-in-part of PCT/US93/09987, filed Oct. 15, 1993, which is a continuation-in-part of 07/977,339, filed Nov. 17, 1992, now abandoned.

FIELD OF THE INVENTION

The invention relates to the preparation and use of nucleic acid fragments encoding fatty acid desaturase enzymes to modify plant lipid composition. Chimeric genes incorporating such nucleic acid fragments and suitable regulatory sequences may be used to create transgenic plants with altered levels of unsaturated fatty acids.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to economically produce large amounts of the desired lipid.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids. The relative amounts of saturated and unsaturated fatty acids in commonly used, edible vegetable oils are summarized below (Table 1):

TABLE 1

Percentages of Saturated and Unsaturated Fatty Acids in the Oils of Selected Oil Crops

|           | Saturated | Mono-unsaturated | Poly-unsaturated |
|-----------|-----------|------------------|------------------|
| Canola    | 6%        | 58%              | 36%              |
| Soybean   | 15%       | 24%              | 61%              |
| Corn      | 13%       | 25%              | 62%              |
| Peanut    | 18%       | 48%              | 34%              |
| Safflower | 9%        | 13%              | 78%              |
| Sunflower | 9%        | 41%              | 51%              |
| Cotton    | 30%       | 19%              | 51%              |

Many recent research efforts have examined the role that saturated and unsaturated fatty acids play in reducing the risk of coronary heart disease. In the past, it was believed that mono-unsaturates, in contrast to saturates and poly-unsaturates, had no effect on serum cholesterol and coronary heart disease risk. Several recent human clinical studies suggest that diets high in mono-unsaturated fat and low in saturated fat may reduce the "bad" (low-density lipoprotein) cholesterol while maintaining the "good" (high-density lipoprotein) cholesterol (Mattson et al., Journal of Lipid Research (1985) 26:194–202).

A vegetable oil low in total saturates and high in mono-unsaturates would provide significant health benefits to consumers as well as economic benefits to oil processors. As an example, canola oil is considered a very healthy oil. However, in use, the high level of poly-unsaturated fatty acids in canola oil renders the oil unstable, easily oxidized, and susceptible to development of disagreeable odors and flavors (Gailliard, 1980, Vol. 4, pp. 85–116 In: Stumpf, P. K., Ed., The Biochemistry of Plants, Academic Press, New York). The levels of poly-unsaturates may be reduced by hydrogenation, but the expense of this process and the concomitant production of nutritionally questionable trans isomers of the remaining unsaturated fatty acids reduces the overall desirability of the hydrogenated oil (Mensink et al., New England J. Medicine (1990) N323: 439–445). Similar problems exist with soybean and corn oils.

For specialized uses, high levels of poly-unsaturates can be desirable. Linoleate and linolenate are essential fatty acids in human diets, and an edible oil high in these fatty acids can be used for nutritional supplements, for example in baby foods.

Mutation-breeding programs have met with some success in altering the levels of poly-unsaturated fatty acid levels found in the edible oils of agronomic species. Examples of commercially grown varieties are high (85%) oleic sunflower and low (2%) linolenic flax (Knowles, (1980) pp. 35–38 In: Applewhite, T. H., Ed., World Conference on Biotechnology for the Fats and Oils Industry Proceedings, American Oil Chemists' Society). Similar commercial progress with the other plants shown in Table 1 has been largely elusive due to the difficult nature of the procedure and the pleiotropic effects of the mutational regime on plant hardiness and yield potential.

The biosynthesis of the major plant lipids has been the focus of much research (Browse et al., Ann. Rev. Plant Physiol. Mol. Biol. (1991) 42:467–506). These studies show that, with the notable exception of the soluble stearoyl-acyl carrier protein desaturase, the controlling steps in the production of unsaturated fatty acids are largely catalyzed by membrane-associated fatty acid desaturases. Desaturation reactions occur in plastids and in the endoplasmic reticulum using a variety of substrates including galactolipids, sulfolipids, and phospholipids. Genetic and physiological analyses of *Arabidopsis thaliana* nuclear mutants defective in various fatty acid desaturation reactions indicates that most of these reactions are catalyzed by enzymes encoded at single genetic loci in the plant. The analyses show further that the different defects in fatty acid desaturation can have profound and different effects on the ultra-structural morphology, cold sensitivity, and photosynthetic capacity of the plants (Ohlrogge, et al., Biochim. Biophys. Acta (1991) 1082:1–26). However, biochemical characterization of the desaturase reactions has been meager. The instability of the enzymes and the intractability of their proper assay has largely limited researchers to investigations of enzyme activities in crude membrane preparations. These investigations have, however, demonstrated the role of delta-12 desaturase and delta-15 desaturase activities in the production of linoleate and linolenate from 2-oleoyl-phosphatidylcholine and 2-linoleoyl-phosphatidylcholine, respectively (Wang et al., Plant Physiol. Biochem. (1988) 26:777–792). Thus, modification of the activities of these enzymes represents an attractive target for altering the levels of lipid unsaturation by genetic engineering.

Nucleotide sequences encoding microsomal delta-9 stearoyl-coenzyme-A desaturases from yeast, rat, and mice have been described (Stukey, et al., J. Biol. Chem. (1990) 265:20144–20149; Thiede, et al., J. Biol. Chem. (1986) 261:13230–13235; Kaestner, et al., J. Biol. Chem. (1989) 264:14755–1476). Nucleotide sequences encoding soluble delta-9 stearoyl-acyl carrier protein desaturases from higher plants have also been described (Thompson, et al., Proc. Natl. Acad. Sci. U.S.A. (1991) 88:2578–2582; Shanklin et al., Proc. Natl. Acad. Sci. USA (1991) 88:2510–2514). A nucleotide sequence from coriander plant encoding a soluble fatty acid desaturase, whose deduced amino acid sequence is highly identical to that of the stearoyl-acyl carrier protein desaturase and which is responsible for introducing the double bond in petroselinic fatty acid (18:1, 6c), has also been described [Cahoon, et. al. (1992) Proc. Natl. Acad. Sci. U.S.A. 89:11184–11188]. Two fatty acid desaturase genes from the cyanobacterium, Synechocystis PCC6803, have been described: one encodes a fatty acid desaturase, designated des A, that catalyzes the conversion of oleic acid at the sn-1 position of galactolipids to linoleic acid [Wada, et al., Nature (1990) 347:200–203]; another encodes a delta-6 fatty acid desaturase that catalyzes the conversion of linoleic acid at the sn-1 position of galactolipids to γ-linolenic acid (18:2, 6c,9c) [WO 9306712]. Nucleotide sequences encoding higher plant membrane-bound microsomal and plastid delta-15 fatty acid desaturases have also been described [WO 9311245]; Arondel, V. et. al. (1992) Science 258:1353–1355]. There is no report of the isolation of higher plant genes encoding fatty acid desaturases other than the soluble delta-6 and delta-9 desaturases and the membrane-bound (microsomal and plastid) delta-15 desaturases. While there is extensive amino acid sequence identity between the soluble desaturases and significant amino acid sequence identity between the higher plant microsomal and plastid delta-15 desaturases, there is no significant homology between the soluble and the membrane-bound desaturases. Sequence-dependent protocols based on the sequences encoding delta-15 desaturases have been unsuccessful in cloning sequences for microsomal delta-12 desaturase. For example, nucleotide sequences of microsomal or plastid delta-15 desaturases as hybridization probes have been unsuccessful in isolating a plant microsomal delta-12 desaturase clone. Furthermore, while we have used a set of degenerate oligomers made to a stretch of 12 amino acids, which is identical in all plant delta-15 desaturases and highly conserved (10/12) in the cyanobacterial des A desaturase, as a hybridization probe to isolate a higher plant nucleotide sequence encoding plastid delta-12 fatty acid desaturase, this method has been unsuccessful in isolating the microsomal delta-12 desaturase cDNAs. Furthermore, there has been no success in isolating the microsomal delta-12 desaturase by using the polymerase chain reaction products derived from plant DNA, plant RNA or plant cDNA library using PCR primers made to stretches of amino acids that are conserved between the higher plant delta-15 and des A desaturases. Thus, there are no teachings which enable the isolation of plant microsomal delta-12 fatty acid desaturases or plant fatty acid desaturase-related enzymes. Furthermore, there is no evidence for a method to control the the level of delta-12 fatty acid desaturation or hydroxlylation in plants using nucleic acids encoding delta-12 fatty acid desaturases or hydroxylases.

The biosynthesis of the minor plant lipids has been less well studied. While hundreds of different fatty acids have been found, many from the plant kingdom, only a tiny fraction of all plants have been surveyed for their lipid content (Gunstone, et al., Eds., (1986) The Lipids Handbook, Chapman and Hall Ltd., Cambridge). Accordingly, little is known about the biosynthesis of these unusual fatty acids and fatty acid derivatives. Interesting chemical features found in such fatty acids include, for example, allenic and conjugated double bonds, acetylenic bonds, trans double bonds, multiple double bonds, and single double bonds in a wide number of positions and configurations along the fatty acid chain. Similarly, many of the structural modifications found in unusual lipids (e.g., hydroxylation, epoxidation, cyclization, etc.) are probably produced via further metabolism following chemical activation of the fatty acid by desaturation or they involve a chemical reaction that is mechanistically similar to desaturation. Many of these fatty acids and derivatives having such features within their structure could prove commercially useful if an agronomically viable species could be induced to synthesize them by introduction of a gene encoding the appropriate desaturase. Of particular interest are vegetable oils rich in 12-hydroxyoctadeca-9-enoic acid (ricinoleic acid). Ricinoleic acid and its derivatives are widely used in the manufacture of lubricants, polymers, cosmetics, coatings and pharmaceuticals (e.g., see Gunstone, et al., Eds., (1986) The Lipids Handbook, Chapman and Hall Ltd., Cambridge). The only commercial source of ricinoleic acid is castor oil and 100% of the castor oil used by the U.S. is derived from beans grown elsewhere in the world, mainly Brazil. Ricinoleic acid in castor beans is synthesized by the addition of an hydroxyl group at the delta-12 position of oleic acid (Galliard & Stumpf (1966) J. Biol. Chem. 241: 5806–5812). This reaction resembles the initial reaction in a possible mechanism for the desaturation of oleate at the delta-12 position to linoleate since dehydration of 12-hydroxyoctadeca-9-enoic acid, by an enzyme activity analogous to the hydroxydecanoyl dehydrase of E. coli (Cronan et al. (1988) J. Biol. Chem. 263:4641–4646), would result in the formation of linoleic acid. Evidence for the hydroxylation reaction being part of a general mechanism of enzyme-catalyzed desaturation in eukaryotes has been obtained by substituting a sulfur atom in the place of carbon at the delta-9 position of stearic acid. When incubated with yeast cell extracts the thiostearate was converted to a 9-sulfoxide (Buist et al. (1987) Tetrahedron Letters 28:857–860). This sulfoxidation was specific for sulfur at the delta-9 position and did not occur in a yeast delta-9-desaturase deficient mutant (Buist & Marecak (1991) Tetrahedron Letters 32:891–894). The 9-sulfoxide is the sulfur analogue of 9-hydroxyoctadecastearate, the proposed intermediate of stearate desaturation.

Hydroxylation of oleic acid to ricinoleic acid.in castor bean cells, like microsomal desaturation of oleate in plants, occurs at the delta-12 position of the fatty acid at the sn-2 position of phosphatidylcholine in microsomes (Bafor et al. (1991) Plant Physiol 280:507–514). Furthermore, castor oleate delta-12 hydroxylation and plant oleate microsomal delta-12 desaturation are both inhibited by iron chelators and require molecular oxygen [Moreau & Stumpf (1981) Plant Physiology 67:672–676; Somerville, C. (1992) MSU-DOE Plant Research Laboratory Annual Report]. These biochemical similarities in conjunction with the observation that antibodies raised against cytochrome $b_5$ completely inhibit the activities of both oleate delta-12 desaturation in safflower microsomes and oleate delta-12 hydroxylase in castor microsomes [Somerville, C. (1992) MSU-DOE Plant Research Laboratory Annual Report] comprise strong evidence that the hydroxylase and the desaturase are functionally related. It seems reasonable to assume, therefore, that the nucleotide sequence encoding a plant delta-12 desaturase would be useful in cloning the oleate hydroxylase gene from castor by sequence-dependent protocols. For example, by screening a castor DNA library with oligomers based on amino acid regions conserved between delta-12 desaturases, or regions conserved between delta-12 and other desaturases, or with oligomers based on amino acids conserved between delta-12 desaturases and known membrane-associated hydroxylases. It would be more efficient to isolate the castor oleate hydroxylase cDNA by combining the sequence dependent protocols with a "differential" library approach. One example of such a difference library would be based on different stages of castor seed development, since ricinoleic acid is not synthesized by very young castor seeds (less than 12 DAP, corresponding to stage I and stage II seeds in the scheme of Greenwood & Bewley, Can. J. Bot. (1982) 60:1751–1760), in the 20 days following these early stages the relative ricinoleate content increases from 0% to almost 90% of total seed fatty acids (James et al. Biochem. J. (1965) 95:448–452, Canvin. Can. J. Biochem. Physiol. (1963) 41:1879–1885). Thus it would be possible to make a cDNA "difference" library made from mRNA present in a stage when ricinoleic acid was being synthesized at a high rate but from which mRNA present in earlier stages was removed. For the earlier stage mRNA, a stage such as stage II (10 DAP) when ricinoleic acid is not being made but when other unsaturated fatty acids are, would be appropriate. The construction of libraries containing only differentially expressed genes is well known in the art (Sargent. Meth. Enzymol. (1987) 152:423–432). Assembly of the free ricinoleic acid, via ricinoleoyl-CoA, into triacylglycerol is readily catalyzed by canola and safflower seed microsomes (Bafor et al., Biochem J. (1991) 280:507–514, Wiberg et al. 10th International Symposium on the Metabolism, Strucure & Function of Plant Lipids (1992), Jerba, Tunisia) and ricinoleic acid is removed from phosphatidylcholine by a lipase common to all oilseeds investigated. Thus, expression of the castor bean oleate hydroxylase gene in oil crops, such as canola seeds and soybeans, would be expected to result in an oil rich in triglycerides containing ricinoleic acid.

SUMMARY OF THE INVENTION

Applicants have discovered a means to control the nature and levels of unsaturated fatty acids in plants. Nucleic acid fragments from cDNAs or genes encoding fatty acid desaturases are used to create chimeric genes. The chimeric genes may be used to transform various plants to modify the fatty acid composition of the plant or the oil produced by the plant. More specifically, one embodiment of the invention is an isolated nucleic acid fragment comprising a nucleotide sequence encoding a fatty acid desaturase or a fatty acid desaturase-related enzyme with an amino acid identity of 50%, 60%, 90% or greater respectively to the polypeptide encoded by SEQ ID NOS:1, 3, 5, 7, 9, 11, or 15. Most specifically, the invention pertains to a gene sequence for plant microsomal delta-12 fatty acid desaturase or desaturase-related enzyme. The plant in this embodiment may more specifically be soybean, oilseed Brassica species, *Arabidopsis thaliana*, castor, and corn.

Another embodiment of this invention involves the use of these nucleic acid fragments in sequence-dependent protocols. Examples include use of the fragments as hybridization probes to isolate nucleotide sequences encoding other fatty acid desaturases or fatty acid desaturase-related enzymes. A related embodiment involves using the disclosed sequences for amplification of RNA or DNA fragments encoding other fatty acid desaturases or fatty acid desaturase-related enzymes.

Another aspect of this invention involves chimeric genes capable of modifying the fatty acid composition in the seed of a transformed plant, the gene comprising nucleic acid fragments related as defined to SEQ ID NOS:1, 3, 5, 7, 9, or 15 encoding fatty acid desaturases or SEQ ID NOS:11 encoding a desaturase or desaturase-related enzyme operably-linked in suitable orientation to suitable regulatory sequences. Preferred are those chimeric genes which incorporate nucleic acid fragments encoding microsomal delta-12 fatty acid desaturase or desaturase-related enzymes.

Yet another embodiment of the invention involves a method of producing seed oil containing altered levels of unsaturated fatty acids comprising: (a) transforming a plant cell with a chimeric gene described above; (b) growing sexually mature plants from the transformed plant cells of step (a); (c) screening progeny seeds from the sexually mature plants of step (b) for the desired levels of unsaturated fatty acids, and (d) processing the progeny seed of step (c) to obtain seed oil containing altered levels of the unsaturated fatty acids. Preferred plant cells and oils are derived from soybean, rapeseed, sunflower, cotton, cocoa, peanut, safflower, coconut, flax, oil palm, and corn. Preferred methods of transforming such plant cells would include the use of Ti and Ri plasmids of Agrobacterium, electroporation, and high-velocity ballistic bombardment.

The invention also is embodied in a method of RFLP breeding to obtain altered levels of oleic acids in the seed oil of oil producing plant species. This method involves (a) making a cross between two varieties of oil producing plant species differing in the oleic acid trait; (b) making a Southern blot of restriction enzyme digested genomic DNA isolated from several progeny plants resulting from the cross; and (c) hybridizing the Southern blot with the radiolabelled nucleic acid fragments encoding the fatty acid desaturases or desaturase-related enzymes.

The invention is also embodied in a method of RFLP mapping that uses the isolated microsomal delta-12 desaturase cDNA or related genomic fragments described herein.

The invention is also embodied in plants capable of producing altered levels of fatty acid desaturase by virtue of containing the chimeric genes described herein. Further, the invention is embodied by seed oil obtained from such plants.

BRIEF DESCRIPTION OF THE SEOUENCE DESCRIPTIONS

The invention can be more fully understood from the following detailed description and the Sequence Descriptions which form a part of this application. The Sequence Descriptions contain the three letter codes for amino acids as defined in 37 C.F.R. 1.822 which are incorporated herein by reference.

SEQ ID NO:1 shows the 5' to 3' nucleotide sequence of 1372 base pairs of the *Arabidopsis thaliana* cDNA which encodes microsomal delta-12 desaturase. Nucleotides 93–95 and nucleotides 1242–1244 are, respectively, the putative initiation codon and the termination codon of the open reading frame (nucleotides 93–1244). Nucleotides 1–92 and 1245–1372 are, respectively, the 5' and 3' untranslated nucleotides.

SEQ ID NO:2 is the 383 amino acid protein sequence deduced from the open reading frame (nucleotides 93–1244 in SEQ ID NO:1.

SEQ ID NO:3 shows the 5' to 3' nucleotide sequence of 1426 base pairs of the *Brassica napus* cDNA which encodes microsomal delta-12 desaturase in plasmid pCF2-165 d. Nucleotides 130 to 132 and nucleotides 1282 to 1284 are, respectively, the putative initiation codon and the termination codon of the open reading frame (nucleotides 130 to 1284). Nucleotides 1 to 129 and 1285 to 1426 are, respectively, the 5' and 3' ntranslated nucleotides.

SEQ ID NO:4 is the 384 amino acid protein sequence deduced from the open reading frame (nucleotides 130 to 1284) in SEQ ID NO:3.

SEQ ID NO:5 shows the 5' to 3' nucleotide sequence of 1369 base pairs of soybean (*Glycine max*) cDNA which encodes microsomal delta-12 desaturase in plasmid pSF2-169K. Nucleotides 108 to 110 and nucleotides 1245 to 1247 are, respectively, the putative initiation codon and the termination codon of the open reading frame (nucleotides 108 to 1247). Nucleotides 1 to 107 and 1248 to 1369 are, respectively, the 5' and 3' untranslated nucleotides.

SEQ ID NO:6 is the 381 amino acid protein sequence deduced from the open reading frame (nucleotides 113 to 1258) in SEQ ID NO:5.

SEQ ID NO:7 shows the 5' to 3' nucleotide sequence of 1790 base pairs of corn (*Zea mays*) cDNA which encodes microsomal delta-12 desaturase in plasmid pFad2#1. Nucleotides 165 to 167 and nucleotides 1326 to 1328 are, respectively, the putative initiation codon and the termination codon of the open reading frame (nucleotides 164 to 1328). Nucleotides 1 to 163 and 1329 to 1790 are, respectively, the 5' and 3' untranslated nucleotides.

SEQ ID NO:8 is the 387 amino acid protein sequence deduced from the open reading frame (nucleotides 164 to 1328) in SEQ ID NO:7.

SEQ ID NO:9 shows the 5' to 3' nucleotide sequence of 673 base pairs of castor (*Ricinus communis*) incomplete cDNA which encodes part of a microsomal delta-12 desaturase in plasmid pRF2-1C. The sequence encodes an open reading frame from base 1 to base 673.

SEQ ID NO:10 is the 219 amino acid protein sequence deduced from the open reading frame (nucleotides 1 to 657) in SEQ ID NO:9.

SEQ ID NO:11 shows the 5' to 3' nucleotide sequence of 1369 base pairs of castor (*Ricinus communis*) cDNA which encodes part of a microsomal delta-12 desaturase or desaturase-related enzyme in plasmid pRF197C-42. Nucleotides 184 to 186 and nucleotides 1340 to 1342 are, respectively, the putative initiation codon and the termination codon of the open reading frame (nucleotides 184 to 1347). Nucleotides 1 to 183 and 1348 to 1369 are, respectively, the 5' and 3' untranslated nucleotides.

SEQ ID NO:12 is the 387 amino acid protein sequence deduced from the open reading frame (nucleotides 184 to 1342) in SEQ ID NO:11.

SEQ ID NO:13 is the sequence of a set of 64-fold degenerate 26 nucleotide-long oligomers, designated NS3, made to conserved amino acids 101–109 of SEQ ID NO:2, designed to be used as sense primers in PCR to isolate novel sequences encoding microsomal delta-12 desaturases or desaturase-like enzymes.

SEQ ID NO:14 is the sequence of a set of 64-fold degenerate and 26 nucleotide-long oligomers, designated NS9, which is made to conserved amino acids 313–321 of SEQ ID NO:2 and designed to be used as antisense primers in PCR to isolate novel sequences encoding microsomal delta-12 desaturases or desaturase-like enzymes.

SEQ ID NO:15 shows the 5' to 3' nucleotide sequence of 2973 bp of *Arabidopsis thaliana* genomic fragment containing the microsomal delta-12 desaturase gene contained in plasmid pAGF2-6. Its nucleotides 433 and 2938 correspond to the start and end, respectively, of SEQ ID NO:1. Its nucleotides 521 to 1654 are the 1134 bp intron.

SEQ ID NO:16 is the sequence of a set of 256-fold degenerate and 25 nucleotide-long oligomers, designated RB5a, which is made to conserved amino acids 318–326 of SEQ ID NO:2 and designed to be used as antisense primers in PCR to isolate novel sequences encoding microsomal delta-12 desaturases or desaturase-like enzymes.

SEQ ID NO:17 is the sequence of a set of 128-fold degenerate and 25 nucleotide-long oligomers, designated RB5b, which is made to conserved amino acids 318–326 of SEQ ID NO:2 and designed to be used as antisense primers in PCR to isolate novel sequences encoding microsomal delta-12 desaturases or desaturase-like enzymes.

DETAILED DESCRIPTION OF THE INVENTION

Applicants have isolated nucleic acid fragments that encode plant fatty acid desaturases and that are useful in modifying fatty acid composition in oil-producing species by genetic transformation.

Thus, transfer of the nucleic acid fragments of the invention or a part thereof that encodes a functional enzyme, along with suitable regulatory sequences that direct the transcription of their mRNA, into a living cell will result in the production or over-production of plant fatty acid desaturases and will result in increased levels of unsaturated fatty acids in cellular lipids, including triacylglycerols.

Transfer of the nucleic acid fragments of the invention or a part thereof, along with suitable regulatory sequences that direct the transcription of their antisense RNA, into plants will result in the inhibition of expression of the endogenous fatty acid desaturase that is substantially homologous with the transferred nucleic acid fragment and will result in decreased levels of unsaturated fatty acids in cellular lipids, including triacylglycerols.

Transfer of the nucleic acid fragments of the invention or a part thereof, along with suitable regulatory sequences that direct the transcription of their mRNA, into plants may result in inhibition by cosuppression of the expression of the endogenous fatty acid desaturase gene that is substantially homologous with the transferred nucleic acid fragment and may result in decreased levels of unsaturated fatty acids in cellular lipids, including triacylglycerols.

The nucleic acid fragments of the invention can also be used as restriction fragment length polymorphism (RFLP) markers in plant genetic mapping and plant breeding programs.

The nucleic acid fragments of the invention or oligomers derived therefrom can also be used to isolate other related fatty acid desaturase genes using DNA, RNA, or a library of cloned nucleotide sequences from the same or different species by well known sequence-dependent protocols, including, for example, methods of nucleic acid hybridization and amplification by the polymerase chain reaction.

Definitions

In the context of this disclosure, a number of terms shall be used. Fatty acids are specified by the number of carbon atoms and the number and position of the double bond: the numbers before and after the colon refer to the chain length and the number of double bonds, respectively. The number following the fatty acid designation indicates the position of the double bond from the carboxyl end of the fatty acid with the "c" affix for the cis-configuration of the double bond. For example, palmitic acid (16:0), stearic acid (18:0), oleic acid (18:1,9c), petroselinic acid (18:1, 6c), linoleic acid (18:2, 9c,12c), γ-linolenic acid (18:3, 6c,9c,12c) and α-linolenic acid (18:3, 9c,12c,15c). Unless otherwise specified 18:1, 18:2 and 18:3 refer to oleic, linoleic and linolenic fatty acids. Ricinoleic acid refers to an 18 carbon fatty acid with a cis-9 double bond and a 12-hydroxyl group. The term "fatty acid desaturase" used herein refers to an enzyme which catalyzes the breakage of a carbon-hydrogen bond and the introduction of a carbon-carbon double bond into a fatty acid molecule. The fatty acid may be free or esterified to another molecule including, but not limited to, acyl-carrier protein, coenzyme A, sterols and the glycerol moiety of glycerolipids. The term "glycerolipid desaturases" used herein refers to a subset of the fatty acid desaturases that act on fatty acyl moieties esterified to a glycerol backbone. "Delta-12 desaturase" refers to a fatty acid desaturase that catalyzes the formation of a double bond between carbon positions 6 and 7 (numbered from the methyl end), (i.e., those that correspond to carbon positions 12 and 13 (numbered from the carbonyl carbon) of an 18 carbon-long fatty acyl chain. "Delta-15 desaturase" refers to a fatty acid desaturase that catalyzes the formation of a double bond between carbon positions 3 and 4 (numbered from the methyl end), (i.e., those that correspond to carbon positions 15 and 16 (numbered from the carbonyl carbon) of an 18 carbon-long fatty acyl chain. Examples of fatty acid desaturases include, but are not limited to, the microsomal delta-12 and delta-15 desaturases that act on phosphatidylcholine lipid substrates; the chloroplastic or plastid delta-12 and delta-15 desaturases that act on phosphatidyl glycerol and galactolipids; and other desaturases that act on such fatty acid substrates such as phospholipids, galactolipids, and sulfolipids. "Microsomal desaturase" refers to the cytoplasmic location of the enzyme, while "chloroplast desaturase" and "plastid desaturase" refer to the plastid location of the enzyme. These fatty acid desaturases may be found in a variety of organisms including, but not limited to, higher plants, diatoms, and various eukaryotic and prokaryotic microorganisms such as fungi and photosynthetic bacteria and algae. The term "homologous fatty acid desaturases" refers to fatty acid desaturases that catalyze the same desaturation on the same lipid substrate. Thus, microsomal delta-15 desaturases, even from different plant species, are homologous fatty acid desaturases. The term "heterologous fatty acid desaturases" refers to fatty acid desaturases that catalyze desaturations at different positions and/or on different lipid substrates. Thus, for example, microsomal delta-12 and delta-15 desaturases, which act on phosphatidylcholine lipids, are heterologous fatty acid desaturases, even when from the same plant. Similarly, microsomal delta-15 desaturase, which acts on phosphatidylcholine lipids, and chloroplast delta-15 desaturase, which acts on galactolipids, are heterologous fatty acid desaturases, even when from the same plant. It should be noted that these fatty acid desaturases have never been isolated and characterized as proteins. Accordingly, the terms such as "delta-12 desaturase" and "delta-15 desaturase" are used as a convenience to describe the proteins encoded by nucleic acid fragments that have been isolated based on the phenotypic effects caused by their disruption. They do not imply any catalytic mechanism. For example, delta-12 desaturase refers to the enzyme that catalyzes the formation of a double bond between carbons 12 and 13 of an 18 carbon fatty acid irrespective of whether it "counts" the carbons from the methyl, carboxyl end, or the first double bond. The term "fatty acid desaturase-related enzyme" refers to enzymes whose catalytic product may not be a carbon-carbon double bond but whose mechanism of action is similar to that of a fatty acid desaturase (that is, catalysis of the displacement of a carbon-hydrogen bond of a fatty acid chain to form a fatty-hydroxyacyl intermediate or end-product). Examples include delta-12 hydroxylase which means a delta-12 fatty acid hydroxylase or the oleate hydroxylase responsible for the synthesis of ricinoleic acid from oleic acid.

The term "nucleic acid" refers to a large molecule which can be single-stranded or double-stranded, composed of monomers (nucleotides) containing a sugar, a phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to the sequence of DNA or RNA polymers, which can be single- or double-stranded, optionally containing synthetic, non-natural or altered nucleotide bases capable of incorporation into DNA or RNA polymers. The term "oligomer" refers to short nucleotide sequences, usually up to 100 bases long. As used herein, the term "homologous to" refers to the relatedness between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.); or by the comparison of sequence similarity between two nucleic acids or proteins, such as by the method of Needleman et al. (J. Mol. Biol. (1970) 48:443–453). As used herein, "substantially homologous" refers to nucleotide sequences that have more than 90% overall identity at the nucleotide level with the coding region of the claimed sequence, such as genes and pseudo-genes corresponding to the coding regions. The nucleic acid fragments described herein include molecules which comprise possible variations, both man-made and natural, such as but not limited to (a) those that involve base changes that do not cause a change in an encoded amino acid, or (b) which involve base changes that alter an amino acid but do not affect the functional properties of the protein encoded by the DNA sequence, (c) those derived from deletions, rearrangements, amplifications, random or controlled mutagenesis of the nucleic acid fragment, and (d) even occasional nucleotide sequencing errors.

"Gene" refers to a nucleic acid fragment that expresses a specific protein, including regulatory sequences preceding (5' non-coding) and following (3' non-coding) the coding region. "Fatty acid desaturase gene" refers to a nucleic acid fragment that expresses a protein with fatty acid desaturase activity. "Native" gene refers to an isolated gene with its own regulatory sequences as found in nature. "Chimeric gene" refers to a gene that comprises heterogeneous regulatory and coding sequences not found in nature. "Endogenous" gene refers to the native gene normally found in its natural location in the genome and is not isolated. A "foreign" gene refers to a gene not normally found in the host organism but that is introduced by gene transfer. "Pseudo-gene" refers to a genomic nucleotide sequence that does not encode a functional enzyme.

"Coding sequence" refers to a DNA sequence that codes for a specific protein and excludes the non-coding sequences. It may constitute an "uninterrupted coding sequence", i.e., lacking an intron or it may include one or more introns bounded by appropriate splice junctions. An "intron" is a nucleotide sequence that is transcribed in the primary transcript but that is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the coding sequence uninterrupted by introns between initiation and termination codons that encodes an amino acid sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases.

As used herein, "suitable regulatory sequences" refer to nucleotide sequences in native or chimeric genes that are located upstream (5'), within, and/or downstream (3') to the nucleic acid fragments of the invention, which control the expression of the nucleic acid fragments of the invention. The term "expression", as used herein, refers to the transcription and stable accumulation of the sense (mRNA) or the antisense RNA derived from the nucleic acid fragment(s) of the invention that, in conjunction with the protein apparatus of the cell, results in altered levels of the fatty acid desaturase(s). Expression or overexpression of the gene involves transcription of the gene and translation of the mRNA into precursor or mature fatty acid desaturase proteins. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a foreign gene which has substantial homology to an endogenous gene resulting in the suppression of expression of both the foreign and the endogenous gene. "Altered levels" refers to the production of gene product(s) in transgenic organisms in amounts or proportions that differ from that of normal or non-transformed organisms.

"Promoter" refers to a DNA sequence in a gene, usually upstream (5') to its coding sequence, which controls the expression of the coding sequence by providing the recognition for RNA polymerase and other factors required for proper transcription. In artificial DNA constructs promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Transformation" herein refers to the transfer of a foreign gene into the genome of a host organism and its genetically stable inheritance. "Restriction fragment length polymorphism" (RFLP) refers to different sized restriction fragment lengths due to altered nucleotide sequences in or around variant forms of genes. "Molecular breeding" refers to the use of DNA-based diagnostics, such as RFLP, RAPDs, and PCR in breeding. "Fertile" refers to plants that are able to propagate sexually.

"Plants" refer to photosynthetic organisms, both eukaryotic and prokaryotic, whereas the term "Higher plants" refers to eukaryotic plants. "Oil-producing species" herein refers to plant species which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling Brassica species, and *Arabidopsis thaliana*, and wild species which may be a source of unique fatty acids.

"Sequence-dependent protocols" refer to techniques that rely on a nucleotide sequence for their utility. Examples of sequence-dependent protocols include, but are not limited to, the methods of nucleic acid and oligomer hybridization and methods of DNA and RNA amplification such as are exemplified in various uses of the polymerase chain reaction (PCR).

Various solutions used in the experimental manipulations are referred to by their common names such as "SSC", "SSPE", "Denhardt's solution", etc. The composition of these solutions may be found by reference to Appendix B of Sambrook, et al. (Molecular Cloning, A Laboratory Manual, 2nd ed. (1989), Cold Spring Harbor Laboratory Press).

T-DNA Mutagenesis and Identification of an Arabidopsis Mutant Defective in Microsomal Delta-12 Desaturation In T-DNA mutagenesis (Feldmann, et al., Science (1989) 243:1351–1354), the integration of T-DNA in the genome can interrupt normal expression of the gene at or near the site of the integration. If the resultant mutant phenotype can be detected and shown genetically to be tightly linked to the T-DNA insertion, then the "tagged" mutant locus and its wild type counterpart can be readily isolated by molecular cloning by one skilled in the art.

Arabidopsis thaliana seeds were transformed by Agrobacterium tumefaciens C58C1rif strain harboring the avirulent Ti-plasmid pGV3850::pAK1003 that has the T-DNA region between the left and right T-DNA borders replaced by the origin of replication region and ampicillin resistance gene of plasmid pBR322, a bacterial kanamycin resistance gene, and a plant kanamycin resistance gene (Feldmann, et al., Mol. Gen. Genetics (1987) 208:1–9). Plants from the treated seeds were self-fertilized and the resultant progeny seeds, germinated in the presence of kanamycin, were self-fertilized to give rise to a population, designated T3, that was segregating for T-DNA insertions. T3 seeds from approximately 1700 T2 plants were germinated and grown under controlled environment. One leaf from each of ten T3 plants of each line were pooled and analyzed for fatty acid composition. One line, designated 658, showed an incresed level of oleic acid (18:1). Analysis of twelve individual T3 seeds of line 658 identified two seeds that contained greater than 36% oleic acid while the remaining seeds contained 12–22% oleic acid. The mutant phenotype of increased level of oleic acid in leaf and seed tissues of line 658 and its segregation in individual T3 seeds suggested that line 658 harbors a mutation that affects desaturation of oleic acid to linoleic acid in both leaf and seed tissues. When approximately 200 T3 seeds of line 658 were tested for their ability to germinate in the presence of kanamycin, four kanamycin-sensitive seeds were identified, suggesting multiple, possibly three, T-DNA inserts in the original T2 line. When progeny seeds of 100 individual T3 plants were analyzed for fatty acid composition and their ability to germinate on kanamycin, one plant, designated 658-75, was identified whose progeny segregated 7 wild type:2 mutant for the increased oleic acid and 28 sensitive:60 resistant for kanamycin resistance. Approximately 400 T4 progeny seeds of derivative line 658-75 were grown and their leaves analyzed for fatty acid composition. Ninety one of these seedlings were identified as homozygous for the mutant (high oleic acid) phenotype. Eighty-three of these homozygous plants were tested for the presence of nopaline, another marker for T-DNA, and all of them were nopaline positive. On the basis of these genetic studies it was concluded that the mutation in microsomal delta-12 desaturation was linked to the T-DNA.

Isolation of Arabidopsis 658-75 Genomic DNA Containing the Disrupted Gene Controlling Microsomal Delta-12 Desaturation In order to isolate the gene controlling microsomal delta-12 desaturation from wild-type Arabidopsis, a T-DNA-plant DNA "junction" fragment containing a T-DNA border integrated into the host plant DNA was isolated from the homozygous mutant plants of the 658-75 line of Arabidopsis. For this, genomic DNA from the mutant plant was isolated and completely digested by either Bam HI or Sal I restriction enzymes. In each case, one of the resultant fragments was expected to contain the origin of replication and ampicillin-resistance gene of pBR322 as well as the left T-DNA-plant DNA junction fragment. Such fragments were rescued as plasmids by ligating the digested genomic DNA fragments at a dilute concentration to facilitate self-ligation and then using the ligated fragments to transform E. coli cells. While no ampicillin-resistant colony was obtained from the plasmid rescue of Sal I-digested plant genomic DNA, a single ampicillin-resistant colony was obtained from the plasmid rescue of Bam HI-digested plant genomic DNA. The plasmid obtained from this transformant was designated p658-1. Restriction analysis of plasmid p658-1 with Bam HI, Sal I and Eco RI restriction enzymes strongly suggested that it contained the expected 14.2 kb portion of the T-DNA (containing pBR322 sequences) and a putative plant DNA/left T-DNA border fragment in a 1.6 kB Eco RI-Bam HI fragment. The 1.6 kb Eco RI-Bam HI fragment was subcloned into pBluescript SK [Stratagene] by standard cloning procedures described in Sambrook et al., (Molecular Cloning, A Laboratory Manual, 2nd ed. (1989), Cold Spring Harbor Laboratory Press) and the resultant plasmid, designated pS1658.

Isolation of Microsomal Delta-12 Desaturase cDNA and Gene from Wild type Arabidopsis The 1.6 kb Eco RI-Bam HI fragment, which contained the putative plant DNA flanking T-DNA, in plasmid p658-1 was isolated and used as a radiolabeled hybridization probe to screen a cDNA library made to polyA$^+$ mRNA from the above-ground parts of Arabidopsis thaliana plants, which varied in size from those that had just opened their primary leaves to plants which had bolted and were flowering [Elledge et al. (1991) Proc. Natl. Acad Sci. USA 88:1731–1735]. The cDNA inserts in the library were made into an Xho I site flanked by Eco RI sites in lambda Yes vector [Elledge et al. (1991) Proc. Natl. Acad Sci. USA 88:1731–1735]. Of the several positively-hybridizing plaques, four were subjected to plaque purification. Plasmids were excised from the purified phages by site-specific recombination using the cre-lox recombination system in E. coli strain BNN132 [Elledge et al. (1991) Proc. Natl. Acad Sci. USA 88:1731–1735]. The four excised plasmids were digested by Eco RI restriction enzyme and shown to contain cDNA inserts ranging in size between 1 kB and 1.5 kB. Partial nucleotide sequence determination and restriction enzyme mapping of all four cDNAs revealed their common identity.

The partial nucleotide sequences of two cDNAs, designated pSF2b and p92103, containing inserts of ca. 1.2 kB and ca. 1.4 kB, respectively, were determined. The composite sequence derived from these plasmids is shown as SEQ ID NO:1 and is expected to be contained completely in plasmid p92103. SEQ ID NO:1 shows the 5' to 3' nucleotide sequence of 1372 base pairs of the Arabidopsis cDNA which encodes microsomal delta-12 fatty acid desaturase. Nucleotides 93–95 are the putative initiation codon of the open reading frame (nucleotides 93–1244), (identified by comparison of other plant delta-12 desaturases in this application). Nucleotides 1242–1244 are the termination codon. Nucleotides 1 to 92 and 1245–1372 are the 5' and 3' untranslated nucleotides, respectively. The 383 amino acid protein sequence in SEQ ID NO:2 is that deduced from the open reading frame and has an estimated molecular weight of 44 kD.

The gene corresponding to SEQ ID NO:1 was isolated by screening an Arabidopsis genomic DNA library using radiolabeled pSF2b cDNA insert, purifying the positively-hybridizing plaque, and subcloning a 6 kB Hind III insert fragment from the phage DNA in pbluescript vector. The sequence of 2973 nucleotides of the gene is shown in SEQ ID NO:15. Comparison of the sequences of the gene (SEQ ID NO:15) and the cDNA (SEQ ID NO:1) revealed the presence of a single intron of 1134 bp at a position between nucleotide positions 88 and 89 of the cDNA, which is 4 nucleotides 5' to the initiation codon.

The 1.6 kB Eco RI-Bam HI genomic border fragment insert in pS1658 was also partially sequenced from the Bam HI and Eco RI ends. Comparison of the nucleotide sequences of the gene (SEQ ID NO:15), the cDNA (SEQ ID NO:1), the border fragment, and the published sequence of the left end of T-DNA (Yadav et al., (1982) Proc. Natl. Acad. Sci. 79:6322–6326) revealed that a) the sequence of the first 451 nucleotides of the border fragment from the Bam HI end is collinear with that of nucleotides 539 (Bam HI site) to 89 of the cDNA, b) from the Eco RI end, the border fragment is collinear from nucleotides 1 to 61 with that of the left end of T-DNA (except for a deletion of 9 contiguous nucleotides at position 42 in the border fragment), and is collinear from nucleotides 57 to 104 with that of nucleotides 41–88 of the cDNA, and c) the sequence divergences between the border fragment and the cDNA are due to the presence of the intron in the border fragment. These results show that the T-DNA disrupted the microsomal delta-12 desaturase gene in the transcribed region between the promoter and the coding region and 5' to the intron in the untranslated sequence.

A phage DNA containing Arabidopsis microsomal delta-12 desaturase gene was used as a RFLP marker on a Southern blot containing genomic DNA from several progeny of *Arabidopsis thaliana* (ecotype Wassileskija and marker line W100 ecotype Landesberg background) digested with Hind III. This mapped the microsomal delta-12 desaturase gene 13.6 cM proximal to locus c3838, 9.2 cM distal to locus 1At228, and 4.9 cM proximal to Fad D locus on chromosome 3 [Koorneef, M. et al., (1993) in Genetic Maps, Ed. O'Brien, S. J.; Yadav et al. (1993) Plant Physiology 103:467–476]. This position corresponds closely to previously suggested locus for microsomal delta-12 desaturation (Fad 2) [Hugly, S. et al., (1991) Heredity 82:4321].

The open reading frames in SEQ ID NO:1 and in sequences encoding Arabidopsis microsomal delta-15 desaturase [WO 9311245], Arabidopsis plastid delta-15 desaturase [WO 9311245], and cyanobacterial desaturase, des A, [Wada, et al., Nature (1990) 347:200–203; Genbank ID:CSDESA; GenBank Accession No:X53508] as well as their deduced amino acid sequences were compared by the method of Needleman et al. [J. Mol. Biol. (1970) 48:443–453] using gap weight and gap length weight values of 5.0 and 0.3, respectively, for the nucleotide sequences and 3.0 and 0.1, respectively, for protein sequences. The overall identities are summarized in Table 2.

TABLE 2

Percent Identity Between Different Fatty Acid Desaturases at the Nucleotide and Amino Acid Levels

|    |            | a3          | ad          | des A       |
|----|------------|-------------|-------------|-------------|
| a2 | nucleotide | 48(8 gaps)  | 46(6 gaps)  | 43(10 gaps) |
|    | amino acid | 39(9 gaps)  | 34(8 gaps)  | 24(10 gaps) |
| a3 | nucleotide | —           | 65(1 gap)   | 43(9 gaps)  |
|    | amino acid | —           | 65(2 gaps)  | 26(11 gaps) |
| ad | nucleotide | —           | —           | 43(9 gaps)  |
|    | amino acid | —           | —           | 26(11 gaps) | a2, a3, ad, and des A refer, respectively, to SEQ ID NO:1/2, Arabidopsis microsomal delta-15 desaturase, Arabidopsis plastid delta-15 desaturase, and cyanobacterial desaturase, des A. The percent identities in each comparison are shown at both the nucleotide and amino acid levels; the number of gaps imposed by the comparisons are shown in brackets following the percent identities. As expected on the basis of unsuccessful attempts in using delta-15 fatty acid nucleotide sequences as hybridization probes to isolate nucleotide sequences encoding microsomal delta-12 fatty acid desaturase, the overall homology at the nucleotide level between microsomal delta-12 fatty acid desaturase (SEQ ID NO:1) and the nucleotide sequences encoding the other three desaturases is poor (ranging between 43% and 48%). At the amino acid level too, the microsomal delta-12 fatty acid desaturase (SEQ ID NO:2) is poorly related to cyanobacterial des A (less than 24% identity) and the plant delta-15 desaturases (less than 39% identity).

While the overall relatedness between the deduced amino acid sequence of the said invention and the published fatty acid desaturases is limited, more significant identities are observed in shorter stretches of amino acid sequences in the above comparisons. These results confirmed that the T-DNA in line 658-75 had interrupted the normal expression of a fatty acid desaturase gene. Based on the fatty acid phenotype of homozygous mutant line 658-75, Applicants concluded that SEQ ID NO:1 encoded the delta-12 desaturase. Further, Applicants concluded that it was the microsomal delta-12 desaturase, and not the chloroplastic delta-12 desaturase, since: a) the mutant phenotype was expressed strongly in the seed but expressed poorly, if at all, in the leaf of line 658-75, and b) the delta-12 desaturase polypeptide, by comparison to the microsomal and plastid delta-15 desaturase polypeptides [WO 9311245], did not have an N-terminal extension of a transit peptide expected for a nuclear-encoded plastid desaturase.

Plasmid p92103 was deposited on Oct. 16, 1992 with the American Type Culture Collection of Rockville, Md. under the provisions of the Budapest Treaty and bears accession number ATCC 69095.

Expression Of Microsomal Delta-12 Fatty Acid Desaturase In Arabidopsis Fad2-1 Mutant To Complement Its Mutation In Delta-12 Fatty Acid Desaturation To confirm the identity of SEQ ID NO:1 (Arabidopsis microsomal delta-12 fatty acid desaturase cDNA) a chimeric gene comprising of SEQ ID NO:1 was transformed into an Arabidopsis mutant affected in microsomal delta-12 fatty acid desaturation. For this, the ca. 1.4 kb Eco RI fragment containing the cDNA (SEQ ID NO:1) was isolated from plasmid p92103 and sub-cloned in pGA748 vector [An et. al.(1988) Binary Vectors. In: Plant Molecular Biology Manual. Eds Gelvin, S. B. et al. Kluwer Academic Press], which was previously linearized with Eco RI restriction enzyme. In one of the resultant binary plasmid, designated pGA-Fad2, the cDNA was placed in the sense orientation behind the CaMV 35S promoter of the vector to provide constitutive expression.

Binary vector pGA-Fad2 was transformed by the freeze/thaw method [Holsters et al. (1978) Mol. Gen. Genet. 163:181–187] into *Agrobacterium tumefaciens* strain R1000, carrying the Ri plasmid pRiA4b from *Agrobacterium rhizogenes* [Moore et al., (1979) Plasmid 2:617–626] to result in transformants R1000/pGA-Fad2.

Agrobacterium strains R1000 and R1000/pGA-Fad2 were used to transform Arabidopsis mutant fad2-1 [Miquel, M. & Browse, J. (1992) Journal of Biological Chemistry 267:1502–1509] and strain R1000 was used to transform wild type Arabidopsis. Young bolts of plants were sterilized and cut so that a single node was present in each explant. Explants were inoculated by Agrobacteria and incubated at 25° C. in the dark on drug-free MS minimal organics medium with 30 g/L sucrose (Gibco). After four days, the explants were transferred to fresh MS medium containing 500 mg/L cefotaxime and 250 mg/ml carbenicillin for the counterselection of Agrobacterium. After 5 days, hairy roots derived from R1000/pGA-Fad2 transformation were excised and transferred to the same medium containing 50 mg/ml kanamycin. Fatty acid methyl esters were prepared from 5–10 mm of the roots essentially as described by Browse et al., (Anal. Biochem. (1986) 152:141–145) except that 2.5% H$_2$SO$_4$ in methanol was used as the methylation reagent and samples were heated for 1.5 h at 80° C. to effect the methanolysis of the seed triglycerides. The results are shown in Table 3. Root samples 41 to 46, 48 to 51, 58, and 59 are derived from transformation of fad2-1 plants with R1000/pGA Fad2; root samples 52, 53, and 57 were derived from transformation of fad2-1 plants with R1000 and serve as controls; root sample 60 is derived from transformation of wild type Arabidopsis with R1000 and also serves as a control.

TABLE 3

Fatty acid Composition in Transgenic Arabidopsis fad2-1 Hairy Roots Transformed with Agrobacterium R1000/pGA-fad2

| Sample | 16:0 | 16:1 | 18:0 | 18:1 | 18:2 | 18:3 |
|---|---|---|---|---|---|---|
| 41 | 24.4 | 1.8 | 1.7 | 5.0 | 29.4 | 33.8 |
| 42 | 25.6 | 3.7 | 1.3 | 20.0 | 22.0 | 27.5 |
| 43 | 23.6 | — | 1.6 | 7.2 | 27.6 | 36.1 |
| 44 | 24.4 | 1.3 | 4.6 | 16.0 | 18.1 | 33.6 |
| 45 | 20.7 | — | 8.1 | 44.7 | 11.8 | 14.8 |
| 46 | 20.1 | — | 1.8 | 7.5 | 33.7 | 36.0 |
| 48 | 26.1 | 2.9 | 2.1 | 9.5 | 17.6 | 33.4 |
| 49 | 30.8 | 1.0 | 2.4 | 8.7 | 18.7 | 31.1 |
| 50 | 19.8 | 1.9 | 3.3 | 27.7 | 21.8 | 24.4 |
| 51 | 20.9 | 1.1 | 5.0 | 13.7 | 25.0 | 32.1 |
| 58 | 23.5 | 0.3 | 1.4 | 3.6 | 22.1 | 45.9 |
| 59 | 22.6 | 0.6 | 1.4 | 2.8 | 29.9 | 40.4 |
| 52, cont. | 12.3 | — | 2.6 | 64.2 | 4.6 | 16.4 |
| 53, cont. | 20.3 | 9.1 | 2.2 | 55.2 | 1.7 | 9.2 |
| 57, cont. | 10.4 | 2.4 | 0.7 | 65.9 | 3.8 | 12.7 |
| 60,WT | 23.0 | 1.7 | 0.8 | 6.0 | 35.0 | 31.8 |

These results show that expression of Arabidopsis microsomal delta-12 desaturase in a mutant Arabidopsis lacking delta-12 desaturation can result in partial to complete complementation of the mutant. The decrease in oleic acid levels in transgenic roots is accompanied by increases in the levels of both 18:2 and 18:3. Thus, overexpression of this gene in other oil crops, especially canola, which is a close relative of Arabidopsis and which naturally has high levels of 18:1 in seeds, is also expected to result in higher levels of 18:2, which in conjunction with the overexpression of the microsomal delta-15 fatty acid desaturase will result in very high levels of 18:3.

Using Arabidopsis Microsomal Delta-12 Desaturase cDNA as a Hybridization Probe to Isolate Microsomal Delta-12 Desaturase cDNAs from Other Plant Species Evidence for conservation of the delta-12 desaturase sequences amongst species was provided by using the Arabidopsis cDNA insert from pSF2b as a hybridization probe to clone related sequences from *Brassica napus*, and soybean. Furthermore, corn and castor bean microsomal delta-12 fatty acid desaturase were isolated by PCR using primers made to conserved regions of microsomal delta-12 desaturases.

Cloning of a *Brassica napus* Seed cDNA Encoding Seed Microsomal Delta-12 Fatty Acid Desaturase For the purpose of cloning the *Brassica napus* seed cDNA encoding a delta-12 fatty acid desaturase, the cDNA insert from pSF2b was isolated by digestion of pSF2b with EcoR I followed by purification of the 1.2 kb insert by gel electrophoresis. The 1.2 kb fragment was radiolabeled and used as a hybridization probe to screen a lambda phage cDNA library made with poly A$^+$ mRNA from developing *Brassica napus* seeds 20–21 days after pollination. Approximately 600,000 plaques were screened under low stringency hybridization conditions (50 mM Tris pH 7.6, 6×SSC, 5×Denhardt's, 0.5% SDS, 100 ug denatured calf thymus DNA and 50° C.) and washes (two washes with 2×SSC, 0.5% SDS at room temperature for 15 min each, then twice with 0.2×SSC, 0.5% SDS at room temperature for 15 min each, and then twice with 0.2×SSC, 0.5% SDS at 50° C. for 15 min each). Ten strongly-hybridizing phage were plaque-purified and the size of the cDNA inserts was determined by PCR amplication of the insert using phage as template and T3/T7 oligomers for primers. Two of these phages, 165D and 165F, had PCR amplified inserts of 1.6 kb and 1.2 kb respectively and these phages were also used to excise the phagemids as described above. The phagemid derived from phage 165D, designated pCF2-165D, contained a 1.5 kb insert which was sequenced completely on one strand. SEQ ID NO:3 shows the 5' to 3' nucleotide sequence of 1426 base pairs of the *Brassica napus* cDNA which encodes delta-12 desaturase in plasmid pCF2-165d. Nucleotides 130 to 102 and nucleotides 1282 to 1284 are, respectively, the putative initiation codon and the termination codon of the open reading frame (nucleotides 130 to 1284). Nucleotides 1 to 129 and 1280 to 1426 are, respectively, the 5' and 3' untranslated nucleotides. The 383 amino acid protein sequence deduced from the open reading frame in SEQ ID NO:3 is shown in SEQ ID NO:4. While the other strand can easily be sequenced for confirmation, comparisons of SEQ ID NOS:1 and 3 and of SEQ ID NOS:2 and 4, even admitting of possible sequencing errors, showed an overall homology of approximately 84% at level the nucleotide and 90% amino acid level, which confirmed that pCF2-165D is a *Brassica napus* seed cDNA that encoded delta-12 desaturase. Plasmid pCF2-165D has been deposited on Oct. 16, 1992 with the American Type Culture Collection of Rockville, Md. under the provisions of the Budapest Treaty and bears accession number ATCC 69094.

Cloning of a Soybean (*Glycine max*) cDNA Encoding Seed Microsomal Delta-12 Fatty Acid Desaturase A cDNA library was made to poly A$^+$ mRNA isolated from developing soybean seeds, and screened as described above. Radiolabelled probe prepared from pSF2b as described above was added, and allowed to hybridize for 18 h at 50° C. The probes were washed as described above. Autoradiography of the filters indicated that there were 14 strongly hybridizing plaques, and numerous weakly hybridizing plaques. Six of the 14 strongly hybridizing plaques were plaque purified as described above and the cDNA insert size was determined by PCR amplication of the insert using phage as template and T3/T7 oligomers for primers. One of these phages, 169K, had an insert sizes of 1.5 kb and this phage was also used to excise the phagemid as described above. The phagemid derived from phage 169K, designated pSF2-169K, contained a 1.5 kb insert which was sequenced completely on both strands. SEQ ID NO:5 shows the 5' to 3' nucleotide sequence of 1473 base pairs of soybean (*Glycine max*) cDNA which encodes delta-12 desaturase in plasmid pSF2-169K. Nucleotides 108 to 110 and nucleotides 1245 to 1247 are, respectively, the putative initiation codon and the termination codon of the open reading frame (nucleotides 108 to 1247). Nucleotides 1 to 107 and 1248 to 1462 are, respectively, the 5' and 3' untranslated nucleotides. The 380 amino acid protein sequence deduced from the open reading frame in SEQ ID NO:5 is shown in SEQ ID NO:6. Comparisons of SEQ ID NOS:1 and 5 and of SEQ ID NOS:2 and 6, even admitting of possible sequencing errors, showed an overall homology of approximately 65% at the nucleotide level and approximately 70% at the amino acid level, which confirmed that pSF2-169K is a soybean seed cDNA that encoded delta-12 desaturase. A further description of this clone can be obtained by comparison of the SEQ ID NO:1, SEQ ID NO:3, and SEQ ID NO:5 and by analyzing the phenotype of transgenic plants produced by using chimeric genes incorporating the insert of pSF2-169K, in sense or antisense orientation, with suitable regulatory sequences. Plasmid pSF2-169K was deposited on Oct. 16, 1992 with the American Type Culture Collection of Rockville, Md. under the provisions of the Budapest Treaty and bears accession number ATCC 69092.

Cloning of a Corn (*Zea mays*) cDNA Encoding Seed Microsomal Delta-12 Fatty Acid Desaturase Corn microsomal delta-12 desaturase cDNA was isolated using a PCR approach. For this, a cDNA library was made to poly $A^+$ RNA from developing corn embryos in Lambda Zap II vector. This library was used as template for PCR using sets of degenerate oligomers NS3 (SEQ ID NO:13) and RB5A/B (SEQ ID NOS:16 and 17) as sense and antisense primers, respectively. NS3 and RB5A/B correspond to stretches of amino acids 101–109 and 318–326, respectively, of SEQ ID NO:2, which are conserved in most microsomal delta-12 desaturases (for example, SEQ ID NOS:2, 4, 6, 8). PCR was carried out using a PCR kit (Perkin-Elmer) by 40 cycles of 94° C. 1', 45° C., 1 min, and 55° C., 2 min. Analyses of the PCR products on an agarose gel showed the presence of a product of the expected size (720 bp), which was absent in control reactions containing either the sense or antisense primers alone. The fragment was gel purified and then used as a probe for screening the corn cDNA library at 60° C. as described above. One positively-hybridizing plaque was purified and partial sequence determination of its cDNA showed it to be a nucleotide sequence encoding microsomal delta-12 desaturase but truncated at the 3' end. The cDNA insert encoding the partial desaturase was gel isolated and used to probe the corn cDNA library again. Several positive plaques were recovered and characterized. DNA sequence analysis revealed that all of these clones seem to represent the same sequence with the different length of 5' or 3' ends. The clone containing the longest insert, designated pFad2#1, was sequenced completely. The total length of the cDNA is 1790 bp (SEQ ID NO:7) comprising of an open reading frame from nucleotide 165 to 1328 bp that encoded a polypeptide of 388 amino acids. The deduced amino acid sequence of the polypeptide (SEQ ID NO:8) shared overall identities of 71%, 40%, and 38% to Arabidopsis microsomal delta-12 desaturase, Arabidopsis microsomal delta-15 desaturase, and Arabidopsis plastid delta-15 desaturase, respectively. Furthermore, it lacked an N-terminal amino acid extension that would indicate it is a plastid enzyme. Based on these considerations, it is concluded that it encodes a microsomal delta-12 desaturase.

Isolation of cDNAs Encoding Delta-12 Microsomal Fatty Acid Desaturases and Desaturase-Related Enzymes from Castor Bean Seed Polysomal mRNA was isolated from castor beans of stages I–II (5–10 DAP) and also from castor beans of stages IV–V (20–25 DAP). Ten ng of each mRNA was used for separate RT-PCR reactions, using the Perkin-Elmer RT-PCR kit. The reverse transcriptase reaction was primed with random hexamers and the PCR reaction with degenerate delta-12 desaturase primers NS3 and NS9 (SEQ ID NOS:13 and 14). The annealing-extension temperature of the PCR reaction was 50° C. A DNA fragment of approx. 700 bp was amplified from both stage I–II and stage IV–V mRNA. The amplified DNA fragment from one of the reactions was gel purified and cloned into a pGEM-T vector using the Promega pGEM-T PCR cloning kit to create the plasmid pRF2-1C. The 700 bp insert in pRF2-1C was sequenced, as described above, and the resulting DNA sequence is shown in SEQ ID NO:9. The DNA sequence in SEQ ID NO:9 contains an open-reading frame encoding 219 amino acids (SEQ ID NO:10) which has 81% identity (90% similarity) with amino acids 135 to 353 of the Arabidopsis microsomal delta-12 desaturase described in SEQ ID NO:2. The cDNA insert in pRF2-1C is therefore a 676 bp fragment of a full-length cDNA encoding a castor bean seed microsomal delta-12 desaturase. The full length castor bean seed microsomal delta-12 desaturase cDNA may isolated by screening a castor seed cDNA library, at 60° C., with the labeled insert of pRF2-1C as described in the example above. The insert in pRF2-1C may also be used to screen castor bean libraries at lower temperatures to isolate delta-12 desaturase-related sequences, such as the delta-12 hydroxylase.

A cDNA library made to poly $A^+$ mRNA isolated from developing castor beans (stages IV–V, 20–25 DAP) was screened as described above. Radiolabeled probe prepared from pSF2b or pRF2-1C, as described above, were added, and allowed to hybridize for 18 h at 50° C. The filters were washed as described above. Autoradiography of the filters indicated that there were numerous hybridizing plaques, which appeared either strongly-hybridising or weakly-hybridising. Three of the strongly hybridisng plaques (190A-41, 190A-42 and 190A-44) and three of the weakly hybridising plaques, (190B-41, 190b-43 and 197c-42), were plaque purified using the methods described above. The cDNA insert size of the purified phages were determined by PCR amplication of the insert using phage as template and lambda-gt11 oligomers (Clontech lambda-gt11 Amplimers) for primers. The PCR-amplified inserts of the amplified phages were subcloned into pBluescript (Pharmacia) which had been cut with Eco RI and filled in with Klenow (Sambrook et al. (Molecular Cloning, A Laboratory Approach, 2nd. ed. (1989) Cold Spring Harbor Laboratory Press). The resulting plasmids were called pRF190a-41, pRF190a-42, pRF190a-44, pRF190b-41, pRF190b-43 and pRF197c-42. All of the inserts were about 1.1 kb with the exception of pRF197c-42 which was approx. 1.5 kb. The inserts in the plasmids were sequenced as described above. The insert in pRF190b-43 did not contain any open reading frame and was not identified. The inserts in pRF190a-41, pRF190a-42, pRF190a-44 and pRF190b-41 were identical. The insert in pRF197c-42 contained all of the nucleotides of the inserts in pRF190a-41, pRF190a-42, pRF190a-44 and pRF190b-41 plus an additional approx. 400 bp. It was deduced therefore that the insert in pRF197c-42 was a longer version of the inserts in pRF190a-41, pRF190a-42, pRF190a-44 and pRF190b-41 and all were derived from the same full-length mRNA. The complete cDNA sequence of the insert in plasmid pRF197c-42 is shown in SEQ ID NO:11. The deduced amino acid sequence of SEQ ID NO:11, shown in SEQ ID NO:12, is 78.5% identical (90% similarity) to the castor microsomal delta-12 desaturase described above (SEQ ID NO:10) and 66% identical (80% similarity) to the Arabidopsis delta-12 desaturase amino acid sequence in SEQ ID NO:2. These similarities confirm that pRF197c-42 is a castor bean seed cDNA that encodes a microsomal delta-12 desaturase or a microsomal delta-12 desaturase-related enzyme, such as a delta-12 hydroxylase. Specific PCR primers for pRF2-1C and pRF197c-42 were made. For pRF2-1c the upstream primer was bases 180 to 197 of the cDNA sequence in SEQ ID NO:9. For pRF197c-42 the upstream primer was bases 717 to 743 of the cDNA sequence in SEQ ID NO:11. A common downstream primer was made corresponding to the exact complement of the nucleotides 463 to 478 of the sequence described in SEQ ID NO:9. Using RT-PCR with random hexamers and the above primers it was observed that the cDNA contained in pRF2-1C is expressed in both Stage I–II and Stage IV–V castor bean seeds whereas the cDNA contained in plasmid pRF197c-42 is expressed only in Stage IV–V castor bean seeds, i.e., it is only expressed in tissue actively synthesizing ricinoleic acid. Thus, it is possible that this cDNA encodes a delta-12 hydroxylase.

There is enough deduced amino acid sequence from the two castor sequences described in SEQ ID NOS:10 and 12 to compare the highly conserved region corresponding to amino acids 311 to 353 of SEQ ID NO:2. When SEQ ID NOS:2, 4, 6, 8, and 10 are aligned by the Hein method described above the consensus sequence corresponds exactly to the amino acids 311 to 353 of SEQ ID NO:2. All of the seed microsomal delta-12 desaturases described above have a high degree of identity with the consensus over this region, namely Arabidopsis (100% identity), soybean (90% identity), corn (95% identity), canola (93% identity) and one (pRF2-1c) of the castor bean sequences (100% identity). The other castor bean seed delta-12 desaturase or desaturase-related sequence (pRF197c-42) however has less identity with the consensus, namely 81% for the deduced amino acid sequence of the insert in pRF197c-42 (described in SEQ ID NO:12). Thus while it remains possible that the insert in pRF197c-42 encodes a microsomal delta-12 desaturase, this observation supports the hypothesis that it encodes a desaturase-related sequence, namely the delta-12 hydroxylase.

An additional approach to cloning a castor bean seed delta-12 hydroxylase is the screening of a differential population of cDNAs. A lambda-Zap (Stratagene) cDNA library made to polysomal mRNA isolated from developing castor bean endosperm (stages IV–V, 20–25 DAP) was screened with $^{32}$P-labeled cDNA made from polysomal mRNA isolated from developing castor bean endosperm (stage I–II, 5–10 DAP) and with $^{32}$P-labeled cDNA made from polysomal mRNA isolated from developing castor bean endosperm (stages IV–V, 20–25 DAP). The library was screened at a density of 2000 plaques per 137 mm plate so that individual plaques were isolated. About 60,000 plaques were screened and plaques which hybridised with late (stage IV/V) cDNA but not early (stage I/II) cDNA, which corresponded to about 1 in every 200 plaques, were pooled.

The library of differentially expressed cDNAs may be screened with the castor delta-12 desaturase cDNA described above and/or with degenerate oligonucleotides based on sequences of amino conserved among delta-12 desaturases to isolate related castor cDNAs, including the cDNA encoding the delta-12 oleate hydroxylase enzyme. These regions of amino acid conservation may include, but are not limited to amino acids 101 to 109, 137 to 145, and 318 to 327 of the amino acid sequence described in SEQ ID NO:2 or any of the sequences described in Table 7 below.

Examples of such oligomers are SEQ ID NOS:13, 14, 16, and 17. The insert in plasmid pCF2-197c may be cut with Eco RI to remove vector sequences, purified by gel electrophoresis and labeled as described above. Degenerate oligomers based on the above conserved amino acid sequences may be labeled with $^{32}$P as described above. The cDNAs cloned from the developing ehdosperm difference library which do not hybridize with early mRNA probe but do hybridize with late mRNA probe and hybridize with either castor delta-12 desaturase cDNA or with an oligomer based on delta-12 desaturase sequences are likely to be the castor delta-12 hydroxylase. The pBluescript vector containing the putative hydroxylase cDNA can be excised and the inserts directly sequenced, as described above.

Clones such as pRF2-1C and pRF197c-42, and other clones from the differential screening, which, based on their DNA sequence, are less related to castor bean seed microsomal delta-12 desaturases and are not any of the known fatty-acid desaturases described above or in WO 9311245, may be expressed, for example, in soybean embryos or another suitable plant tissue, or in a microorganism, such as yeast, which does not normally contain ricinoleic acid, using suitable expression vectors and transformation protocols. The presence of novel ricinoleic acid in the transformed tissue(s) expressing the castor cDNA would confirm the identity of the castor cDNA as DNA encoding for an oleate hydroxylase.

Sequence Comparisons Among Seed Microsomal Delta-12 Desaturases

The percent overall identities between coding regions of the full-length nucleotide sequences encoding microsomal delta-12 desaturases was determined by their alignment by the method of Needleman et al. (J. Mol. Biol. (1970) 48:443–453) using gap weight and gap length weight values of 5.0 and 0.3 (Table 4). Here, a2, c2, s2, z2 and des A refer, respectively, to the nucleotide sequences encoding microsomal delta-12 fatty acid desaturases from Arabidopsis (SEQ ID NO:1), Brassica napus (SEQ ID NO:3), soybean (SEQ ID NO:5), corn (SEQ ID NO:7), and cyanobacterial des A, whereas r2 refers to the microsomal delta-12 desaturase or desaturase-related enzyme from castor bean (SEQ ID NO:12).

TABLE 4

Percent Identity Between the Coding Regions of Nucleotide Sequences Encoding Different Microsomal Delta-12 Fatty Acid Desaturases

|    | c2 | s2 | z2 | des A |
|----|----|----|----|-------|
| a2 | 84 | 66 | 64 | 43    |
| c2 | —  | 65 | 62 | 42    |
| s2 | —  | —  | 62 | 42    |

The overall relatedness between the deduced amino acid sequences of microsomal delta-12 desaturases or desaturase-related enzymes of the invention (i.e., SEQ ID NOS:2, 4, 6, 8, and 12) determined by their alignment by the method of Needleman et al. (J. Mol. Biol. (1970) 48:443–453) using gap weight and gap length weight values of 3.0 and 0.1, respectively, is shown in Table 5. Here a2, c2, s2, z2 and des A refer, respectively, to microsomal delta-12 fatty acid desaturases from Arabidopsis (SEQ ID NO:2), Brassica napus (SEQ ID NO:4), soybean (SEQ ID NO:6), corn (SEQ ID NO:8), and cyanobacterial des A, whereas r2 refers to the microsomal desaturase or desaturase-related enzyme from castor bean (SEQ ID NO:12). The relatedness between the enzymes is shown as percent overall identity/percent overall similarity.

TABLE 5

Relatedness Between Different Microsomal Delta-12 Fatty Acid Desaturases

|    | c2    | s2    | r2    | z2    | des A |
|----|-------|-------|-------|-------|-------|
| a2 | 84/89 | 70/85 | 66/80 | 71/83 | 24/50 |
| c2 | —     | 67/80 | 63/76 | 69/79 | 24/51 |
| s2 | —     | —     | 67/83 | 66/82 | 23/49 |
| r2 | —     | —     | —     | 61/78 | 24/51 |
| z2 | —     | —     | —     | —     | 25/49 |

The high degree of overall identity (60% or greater) at the the amino acid levels between the *Brassica napus*, soybean, castor and corn enzymes with that of Arabidopsis microsomal delta-12 desaturase and their lack of an N-terminal extension of a transit peptide expected for a nuclear-encoded chloroplast desaturase leads Applicants to conclude that SEQ ID NOS:4, 6, 8, 10, and 12 encode the microsomal delta-12 desaturases or desaturase-related enzymes. Further confirmation of this identity will come from biological function, that is, by analyzing the phenotype of transgenic plants or other organisms produced by using chimeric genes incorporating the above-mentioned sequences in sense or antisense orientation, with suitable regulatory sequences. Thus, one can isolate cDNAs and genes for homologous fatty acid desaturases from the same or different higher plant species, especially from the oil-producing species. Furthermore, based on these comparisons, the Applicants expect all higher plant microsomal delta-12 desaturases from all higher plants to show an overall identity of 60% or more and to be able to readily isolate homologous fatty acid desaturase sequences using SEQ ID NOS:1, 3, 5, 7, 9, and 11 by sequence-dependent protocols.

The overall percent identity at the amino acid level, using the above alignment method, between selected plant desaturases is illustrated in Table 6.

TABLE 6

Percent Identity Between Selected Plant Fatty Acid Desaturases at the Amino Acid Level

|    | a3 | aD | c3 | cD | S3 |
|----|----|----|----|----|----|
| a2 | 38 | 33 | 38 | 35 | 34 |
| a3 | —  | 65 | 93 | 66 | 67 |
| aD | —  | —  | 66 | 87 | 65 |
| c3 | —  | —  | —  | 67 | 67 |
| cD | —  | —  | —  | —  | 65 |

In Table 6, a2, a3, ad, c3, cD, and S3 refer, respectively, to SEQ ID NO:2, Arabidopsis microsomal delta-15 desaturase, Arabidopsis plastid delta-15 desaturase, canola microsomal delta-15 desaturase, canola plastid delta-15 desaturase, and soybean microsomal delta-15 desaturase. Based on these comparisons, the delta-15 desaturases, of both microsomal and plastid types, have overall identities of 65% or more at the amino acid level, even when from the same plant species. Based on the above the Applicants expect microsomal delta-12 desaturases from all higher plants to show similar levels of identity (that is, 60% or more identity at the amino acid level) and that SEQ ID NOS:1, 3, 5, 7, and 9 can also be used as hybridization probe to isolate homologous delta-12 desaturase sequences, and possibly for sequences for fatty acid desaturase-related enzymes, such as oleate hydroxylase, that have an overall amino acid homology of 50% or more.

Similar alignments of protein sequences of plant microsomal fatty acid delta-12 desaturases [SEQ ID NOS:2, 4, 6, and 8] and plant delta-15 desaturases [microsomal and plastid delta-15 desaturases from Arabidopsis and *Brassica napus*, WO 9311245] allows identification of amino acid sequences conserved between the different desaturases (Table 7).

TABLE 7

Amino Acid Sequences Conserved Between Plant Microsomal Delta-12 Desatuases and Microsomal and Plastid Delta-15 Desaturases

| Region | Conserved AA Positions in SEQ ID NO:2 | Consensus Conserved AA Sequence in Δ$^{12}$Desaturases | Consensus Conserved AA Sequence in Δ$^{15}$Desaturases | Consensus AA Sequence |
|--------|-----|-----------|-----------|-----------------------|
| A | 39–44   | AIPPHC    | AIPKHC    | AIP(P/K)HC            |
| B | 86–90   | WP(L/I)YW | WPLYW     | WP(L/I)YW             |
| C | 104–109 | AHFCGH    | GHDCGH    | (A/G)H(D/E)CGH        |
| D | 130–134 | LLVPY     | ILVPY     | (L/I)LVPY             |
| E | 137–142 | WKYSHR    | WRISHR    | W(K/R)(Y/I)SHR        |
| F | 140–145 | SHRRHH    | SHRTHH    | SHR(R/T)HH            |
| G | 269–274 | ITYLQ     | VTYLH     | (I/V)TYL(Q/H)         |
| H | 279–282 | LPHY      | LPWY      | LP(H/W)Y              |
| I | 289–294 | WL(R/K)GAL| YLRGGL    | (W/Y)L(R/K)G(A/G)L    |
| J | 296–302 | TVDRDYG   | TLDRDYG   | T(V/L)DRDYG           |
| K | 314–321 | THVAHHLF  | THVIHHLF  | THV(A/I)HHLF          |
| L | 318–327 | HHLFSTMPHY| HHLFPQIPHY| HHFL(S/P)(T/Q)(I/M)PHY|

Table 7 shows twelve regions of conserved amino acid sequences, designated A-L (column 1), whose positions in SEQ ID NO:2 are shown in column 2. The consensus sequences for these regions in plant delta-12 fatty acid desaturases and plant delta-15 fatty acid desaturases are shown in columns 3 and 4, respectively; amino acids are shown by standard abbreviations, the underlined amino acids are conserved between the delta-12 and the delta-15 desaturases, and amino acids in brackets represent substitutions found at that position. The consensus sequence of these regions are shown in column 5. These short conserved amino acids and their relative positions further confirm that the isolated isolated cDNAs encode a fatty acid desaturase.

Isolation of Nucleotide Sequences Encoding Homologous and Heterologous Fatty acid Desaturases and Desaturase-like Enzymes Fragments of the instant invention may be used to isolate cDNAs and genes of homologous and heterologous fatty acid desaturases from the same species as the fragments of the invention or from different species. Isolation of homologous genes using sequence-dependent protocols is well-known in the art and Applicants have demonstrated that Arabidopsis microsomal delta-12 desaturase cDNA sequence can be used to isolate cDNA for related fatty acid desaturases from *Brassica napus*, soybean, corn and castor bean.

More importantly, one can use the fragments containing SEQ ID NOS:1, 3, 5, 7, and 9 or their smaller, more conserved regions to isolate novel fatty acid desaturases and fatty acid desaturase-related enzymes.

In a particular embodiment of the present invention, regions of the nucleic acid fragments of the invention that are conserved between different desaturases may be used by one skilled in the art to design a mixture of degenerate oligomers for use in sequence-dependent protocols aimed at isolating nucleic acid fragments encoding homologous or heterologous fatty acid desaturase cDNA's or genes. For example, in the polymerase chain reaction (Innis, et al., Eds, (1990) PCR Protocols: A Guide to Methods and Applications, Academic Press, San Diego), two short pieces of the present fragment of the invention can be used to amplify a longer fatty acid desaturase DNA fragment from DNA or RNA. The polymerase chain reaction may also be performed on a library of cloned nucleotide sequences with one primer based on the fragment of the invention and the other on either the poly $A^+$ tail or a vector sequence. These oligomers may be unique sequences or degenerate sequences derived from the nucleic acid fragments of the invention. The longer piece of homologous fatty acid desaturase DNA generated by this method could then be used as a probe for isolating related fatty acid desaturase genes or cDNAs from Arabidopsis or other species and subsequently identified by differential screening with known desaturase sequences and by nucleotide sequence determination. The design of oligomers, including long oligomers using deoxyinosine, and "guessmers" for hybridization or for the polymerase chain reaction are known to one skilled in the art and discussed in Sambrook et al., (Molecular Cloning, A Laboratory Manual, 2nd ed. (1989), Cold Spring Harbor Laboratory Press). Short stretches of amino acid sequences that are conserved between cyanobacterial delta-12 desaturase (Wada et al., Nature (1990) 347:200–203) and plant delta-15 desaturases [WO 9311245] were previously used to make oligonucleotides that were degenerate and/or used deoxyinosine/s. One set of these oligomers made to a stretch of 12 amino acids conserved between cyanobacterial delta-12 desaturase and higher plant delta-15 desaturases was successful in cloning the plastid delta-12 desaturase cDNAs; these plant desaturases have more than 50% identity to the cyanobacterial delta-12 desaturase. Some of these oligonucleotides were also used as primers to make polymerase chain reaction (PCR) products using poly $A^+$ RNA from plants. However, none of the oligonucleotides and the PCR products were successful as radiolabeled hybridization probes in isolating nucleotide sequences encoding microsomal delta-12 fatty acid desaturases. Thus, as expected, none of the stretches of four or more amino acids conserved between Arabidopsis delta-12 and Arabidopsis delta-15 desaturases are identical in the cyanobacterial desaturase, just like none of the stretches of four or more amino acids conserved between Arabidopsis delta-15 and the cyanobacterial desaturase are identical in SEQ ID NO:2. Stretches of conserved amino acids between the present invention and delta-15 desaturases now allow for the design of oligomers to be used to isolate sequences encoding other desaturases and desaturase-related enzymes. For example, conserved stretches of amino acids between delta-12 desaturase and delta-15 desaturase, shown in Table 7, are useful in designing long oligomers for hybridization as well as shorter ones for use as primers in the polymerase chain reaction. In this regard, sequences conserved between delta-12 and delta-15 desaturases (shown in Table 7) would be particularly useful. The consensus sequences will also take into account conservative substitutions known to one skilled in the art, such as Lys/Arg, Glu/Asp, Ile/Val/Leu/Met, Ala/Gly, Gln/Asn, and Ser/Thr. Amino acid sequences as short as four amino acids long can successfully be used in PCR [Nunberg et. al. (1989) Journal of Virology 63:3240–3249]. Amino acid sequences conserved between delta-12 desaturases (SEQ ID NOS:2, 4, 6, 8, and 10) may also be used in sequence-dependent protocols to isolate fatty acid desaturases and fatty acid desaturase-related enzymes expected to be more related to delta-12 desaturases, such as the oleate hydroxylase from castor bean. Particularly useful are conserved sequences in column 3 (Table 7), since they are also conserved well with delta-15 desaturases (column 4, Table 7).

Determining the conserved amino acid sequences from diverse desaturases will also allow one to identify more and better consensus sequences that will further aid in the isolation of novel fatty acid desaturases, including those from non-plant sources such as fungi, algae (including the desaturases involved in the desaturations of the long chain n-3 fatty acids), and even cyano-bacteria, as well as other membrane-associated desaturases from other organisms.

The function of the diverse nucleotide fragments encoding fatty acid desaturases or desaturase-related enzymes that can be isolated using the present invention can be identified by transforming plants with the isolated sequences, linked in sense or antisense orientation to suitable regulatory sequences required for plant expression, and observing the fatty acid phenotype of the resulting transgenic plants. Preferred target plants for the transformation are the same as the source of the isolated nucleotide fragments when the goal is to obtain inhibition of the corresponding endogenous gene by antisense inhibition or cosuppression. Preferred target plants for use in expression or overexpression of the isolated nucleic acid fragments are wild type plants or plants with known mutations in desaturation reactions, such as the Arabidopsis mutants fadA, fadB, fadC, fadD, fad2, and fad3; mutant flax deficient in delta-15 desaturation; or mutant sunflower deficient in delta-12 desaturation. Alternatively, the function of the isolated nucleic acid fragments can be determined similarly via transformation of other organisms, such as yeast or cyanobacteria, with chimeric genes containing the nucleic acid fragment and suitable regulatory sequences followed by analysis of fatty acid composition and/or enzyme activity.

Overexpression of the Fatty Acid Desaturase Enzymes in Transgenic Species

The nucleic acid fragment(s) of the instant invention encoding functional fatty acid desaturase(s), with suitable regulatory sequences, can be used to overexpress the enzyme(s) in transgenic organisms. An example of such expression or overexpression is demonstrated by transformation of the Arabidopsis mutant lacking oleate desaturation. Such recombinant DNA constructs may include either the native fatty acid desaturase gene or a chimeric fatty acid desaturase gene isolated from the same or a different species as the host organism. For overexpression of fatty acid desaturase(s), it is preferable that the introduced gene be from a different species to reduce the likelihood of cosuppression. For example, overexpression of delta-12 desaturase in soybean, rapeseed, or other oil-producing species to produce altered levels of polyunsaturated fatty acids may be achieved by expressing RNA from the full-length cDNA found in p92103, pCF2–165D, and pSF2-169K. Transgenic lines overexpressing the delta-12 desaturase, when crossed with lines overexpressing delta-15 desaturases, will result in ultrahigh levels of 18:3. Similarly, the isolated nucleic acid fragments encoding fatty acid desaturases from Arabidopsis, rapeseed, and soybean can also be used by one skilled in the art to obtain other substantially homologous full-length cDNAs, if not already obtained, as well as the corresponding genes as fragments of the invention. These, in turn, may be used to overexpress the corresponding desaturases in plants. One skilled in the art can also isolate the coding sequence(s) from the fragment(s) of the invention by using and/or creating sites for restriction endonucleases, as described in Sambrook et al., (Molecular Cloning, A Laboratory Manual, 2nd ed. (1989), Cold Spring Harbor Laboratory Press).

One particularly useful application of the claimed inventions is to repair the agronomic performance of plant mutants containing ultra high levels of oleate in seed oil. In Arabidopsis reduction in linoleate in phosphatidylcholine due to a mutation in microsomal delta-12 desaturase affected low temperature survival [Miquel, M. et. al. (1993) Proc. Natl Acad. Sci. USA 90:6208–6212]. Furthermore, there is evidence that the poor agronomic performance of canola plants containing ultra high (>80%)levels of oleate in seed is due to mutations in the microsomal delta-12 desaturase genes that reduce the level of linoleate in phosphotidylcholine of roots and leaves. That is, the mutations are not seed-specific. Thus, the root and/or leaf-specific expression (that is, with no expression in the seeds) of microsomal delta-12 desaturase activity in mutants of oilseeds with ultra-high levels of oleate in seed oil will result in agronomically-improved mutant plants with ultra high levels of oleate in seed oil.

Inhibition of Plant Target Genes by Use of Antisense RNA

Antisense RNA has been used to inhibit plant target genes in a tissue-specific manner (see van der Krol et al., Biotechniques (1988) 6:958–976). Antisense inhibition has been shown using the entire cDNA sequence (Sheehy et al., Proc. Natl. Acad. Sci. USA (1988) 85:8805–8809) as well as a partial cDNA sequence (Cannon et al., Plant Molec. Biol. (1990) 15:39–47). There is also evidence that the 3' non-coding sequences (Ch'ng et al., Proc. Natl. Acad. Sci. USA (1989) 86:10006–10010) and fragments of 5' coding sequence, containing as few as 41 base-pairs of a 1.87 kb cDNA (Cannon et al., Plant Molec. Biol. (1990) 15:39–47), can play important roles in antisense inhibition.

The use of antisense inhibition of the fatty acid desaturases may require isolation of the transcribed sequence for one or more target fatty acid desaturase genes that are expressed in the target tissue of the target plant. The genes that are most highly expressed are the best targets for antisense inhibition. These genes may be identified by determining their levels of transcription by techniques, such as quantitative analysis of mRNA levels or nuclear run-off transcription, known to one skilled in the art.

The entire soybean microsomal delta-12 desaturase cDNA was cloned in the antisense orientation with respect to either soybean b-conglycinin, soybean KTi3, and bean phaseolin promoter and the chimeric gene transformed into soybean somatic embryos that were previously shown to serve as good model system for soybean zygotic embryos and are predictive of seed composition (Table 11). Transformed somatic embryos showed inhibition of linoleate biosyntheis. Similarly, the entire Brassica napus microsomal delta-12 desaturase cDNA was cloned in the antisense orientation with respect to a rapeseed napin promoter and the chimeric gene transformed into B. napus. Seeds of transformed B. napus plants showed inhibition of linoleate biosynthesis. Thus, antisense inhibition of delta-12 desaturase in oil-producing species, including corn, Brassica napus, and soybean resulting in altered levels of polyunsaturated fatty acids may be achieved by expressing antisense RNA from the entire or partial cDNA encoding microsomal delta-12 desaturase.

Inhibition of Plant Target Genes by Cosuppression

The phenomenon of cosuppression has also been used to inhibit plant target genes in a tissue-specific manner. Cosuppression of an endogenous gene using the entire cDNA sequence (Napoli et al., The Plant Cell (1990) 2:279–289; van der Krol et al., The Plant Cell (1990) 2:291–299) as well as a partial cDNA sequence (730 bp of a 1770 bp cDNA) (Smith et al., Mol. Gen. Genetics (1990) 224:477–481) are known.

The nucleic acid fragments of the instant invention encoding fatty acid desaturases, or parts thereof, with suitable regulatory sequences, can be used to reduce the level of fatty acid desaturases, thereby altering fatty acid composition, in transgenic plants which contain an endogenous gene substantially homologous to the introduced nucleic acid fragment. The experimental procedures necessary for this are similar to those described above for the overexpression of the fatty acid desaturase nucleic acid fragments except that one may also use a partial cDNA sequence. For example, cosuppression of delta-12 desaturase in Brassica napus and soybean resulting in altered levels of polyunsaturated fatty acids may be achieved by expressing in the sense orientation the entire or partial seed delta-12 desaturase cDNA found in pCF2-165D and pSF2-165K, respectively. Endogenous genes can also be inhibited by non-coding regions of an introduced copy of the gene [For example, Brusslan, J. A. et al. (1993) Plant Cell 5:667–677; Matzke, M. A. et al., Plant Molecular Biology 16:821–830]. We have shown that an Arabidopsis gene (SEQ ID NO:15) corresponding to the cDNA (SEQ ID NO:1) can be isolated. One skilled in the art can readily isolate genomic DNA containing or flanking the genes and use the coding or non-coding regions in such transgene inhibition methods.

Analysis of the fatty acid composition of roots and seeds of Arabidopsis mutants deficient in microsomal delta-12 desaturation shows that they have reduced levels of 18:2 as well as reduced levels of 16:0 (as much as 40% reduced level in mutant seeds as compared to wild type seeds) [Miquel and Browse (1990) in Plant Lipid Biochemistry, Structure, and Utilization, pages 456–458, Ed. Quinn, P. J. and Harwood, J. L., Portland Press. Reduction in the level of 16:0 is also observed in ultra high oleate mutants of *B. napus*. Thus, one can expect that ultra high level of 18:1 in transgenic plants due to antisense inhibition or cosupression using the claimed sequences will also reduce the level of 16:0.

One particularly useful application of the claimed invention is to combine the high oleate trait of the transformed seeds with mutations for altered fatty acid compositions to obtain novel fatty acid compositions and/or improved agronomy. Fatty acid compositions, such as ultra-high oleate levels (EPO 323753 and see below), resulting from mutagenesis alone, such as by combining mutations, may be affected in agronomy or seed germination. Transgene and mutant genes may be combined either by making a genetic cross between the two lines or by transforming the chimeric genes of the inventions into the mutant lines as known to one skilled in the art.

As examples, the high oleic acid trait of the invention can be combined with high stearate mutations, such as soybean A6 [Hammond, E. G. and Fehr, W. R. (1983)] or low linolenic acid mutations and soybean mutants A5, A23, A16 and C1640 [Fehr, W. R. et al. (1992) in Crop Science 32:903–906]. Oils produced from such combinations will provide improved feedstocks for production of margarines, shortenings, spray coating and frying oils and will eliminate or reduce the need for hydrogenation. Furthermore, these oils would provide a health benefit for consumers, for example by reducing or eliminating trans fatty acids which have recently been found to be associated with high risk to cardiovascular diseases.

It can also be combined with other high oleic acid mutants that will result in even higher oleic acid content. Examples of high oleate mutants include soybean lines A5 and N782245 [Martin, B. A. and Rinne, R. W. (1985) Crop Science 25:1055–1058] and rapeseed lines containing about 69% to 77% oleic acid. A mutant (IMC 129) was derived by chemical mutagenesis of Westar and is presently in commercial production in the U.S. This variety has yields comparable to Westar, a leading Canadian variety. Its high oleate trait can be attributed to a mutation found in the coding region ($Glu_{106}$ to $Lys_{106}$) one of the two delta-12 desaturase structural genes found in Westar. Re-mutagenesis of this line resulted in a second mutation in the other delta-12 desaturase structural gene and even higher seed oleic acid content in the double mutant. However the double mutant has significantly higher levels of oleic acid in its leaves and roots than Westar, i.e., the mutant phenotype is not seed specific. The double mutant has extremely poor agronomy characteristics, which appear to be related to the high oleate in its leaves and/or roots. Thus, one can combine the seed-specific high oleic acid content resulting from seed-specific antisense inhibition or cosuppression of the microsomal delta-12 desaturase in transgenic seeds with that in the single mutant with 69–77% oleic acid to obtain levels of seed oleic acid that are as high or higher than that in the double mutant without affecting agronomy. The increased levels of oleic acid in the double homozygotes are associated with reduced levels of saturates. The reduction in saturates is also observed with seed-specific inhibition of delta-12 desaturase in soybean seeds.

Selection of Hosts, Promoters and Enhancers

A preferred class of heterologous hosts for the expression of the nucleic acid fragments of the invention are eukaryotic hosts, particularly the cells of higher plants. Particularly preferred among the higher plants are the oil-producing species, such as soybean (*Glycine max*), rapeseed (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), and peanut (*Arachis hypogaea*).

Expression in plants will use regulatory sequences functional in such plants. The expression of foreign genes in plants is well-established (De Blaere et al., Meth. Enzymol. (1987) 153:277–291). The source of the promoter chosen to drive the expression of the fragments of the invention is not critical provided it has sufficient transcriptional activity to accomplish the invention by increasing or decreasing, respectively, the level of translatable mRNA for the fatty acid desaturases in the desired host tissue. Preferred promoters include (a) strong constitutive plant promoters, such as those directing the 19S and 35S transcripts in cauliflower mosaic virus (Odell et al., Nature (1985) 313:810–812; Hull et al., Virology (1987) 86:482–493),(b) tissue- or developmentally-specific promoters, and (c) other transcriptional promoter systems engineered in plants, such as those using bacteriophage T7 RNA polymerase promoter sequences to express foreign genes. Examples of tissue-specific promoters are the light-inducible promoter of the small subunit of ribulose 1,5-bis-phosphate carboxylase (if expression is desired in photosynthetic tissues), the maize zein protein promoter (Matzke et al., EMBO J. (1984) 3:1525–1532), and the chlorophyll a/b binding. protein promoter (Lampa et al., Nature (1986) 316:750–752).

Particularly preferred promoters are those that allow seed-specific expression. This may be especially useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., Ann. Rev. Plant Physiol. (1984) 35:191–221; Goldberg et al., Cell (1989) 56:149–160). Moreover, different seed storage proteins may be expressed at different stages of seed development.

Expression of seed-specific genes has been studied in great detail (See reviews by Goldberg et al., Cell (1989) 56:149–160 and Higgins et al., Ann. Rev. Plant Physiol. (1984) 35:191–221). There are currently numerous examples of seed-specific expression of seed storage protein genes in transgenic dicotyledonous plants. These include genes from dicotyledonous plants for bean b-phaseolin (Sengupta-Gopalan et al., Proc. Natl. Acad. Sci. USA (1985) 82:3320–3324; Hoffman et al., Plant Mol. Biol. (1988) 11:717–729), bean lectin (Voelker et al., EMBO J. (1987) 6:3571–3577), soybean lectin (Okamuro et al., Proc. Natl. Acad. Sci. USA (1986) 83:8240–8244), soybean Kunitz trypsin inhibitor (Perez-Grau et al., Plant Cell (1989) 1:095–1109), soybean b-conglycinin (Beachy et al., EMBO J. (1985) 4:3047–3053; pea vicilin (Higgins et al., Plant Mol. Biol. (1988) 11:683–695), pea convicilin (Newbigin et al., Planta (1990) 180:461–470), pea legumin (Shirsat et al., Mol. Gen. Genetics (1989) 215:326–331); rapeseed napin (Radke et al., Theor. Appl. Genet. (1988) 75:685–694) as well as genes from monocotyledonous plants such as for maize 15 kD zein (Hoffman et al., EMBO J. (1987) 6:3213–3221), maize 18 kD oleosin (Lee et al., *Proc. Natl. Acad. Sci. USA* (1991) 888:6181–6185), barley b-hordein (Marris et al., Plant Mol. Biol. (1988) 10:359–366) and wheat glutenin (Colot et al., EMBO J. (1987) 6:3559–3564). Moreover, promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in Arabidopsis and *B. napus* seeds (Vandekerckhove et al., Bio/Technology (1989) 7:929–932), bean lectin and bean b-phaseolin promoters to express luciferase (Riggs et al., Plant Sci. (1989) 63:47–57), and wheat glutenin promoters to express chloramphenicol acetyl transferase (Colot et al., EMBO J. (1987) 6:3559–3564).

Of particular use in the expression of the nucleic acid fragment of the invention will be the heterologous promoters from several soybean seed storage protein genes such as those for the Kunitz trypsin inhibitor (Jofuku et al., Plant Cell (1989) 1:1079–1093; glycinin (Nielson et al., Plant Cell (1989) 1:313–328), and b-conglycinin (Harada et al., Plant Cell (1989) 1:415–425). Promoters of genes for a- and b-subunits of soybean b-conglycinin storage protein will be particularly useful in expressing the mRNA or the antisense RNA in the cotyledons at mid- to late-stages of seed development (Beachy et al., EMBO J. (1985) 4:3047–3053) in transgenic plants. This is because there is very little position effect on their expression in transgenic seeds, and the two promoters show different temporal regulation. The promoter for the a-subunit gene is expressed a few days before that for the b-subunit gene. This is important for transforming rapeseed where oil biosynthesis begins about a week before seed storage protein synthesis (Murphy et al., J. Plant Physiol. (1989) 135:63–69).

Also of particular use will be promoters of genes expressed during early embryogenesis and oil bio-synthesis. The native regulatory sequences, including the native promoters, of the fatty acid desaturase genes expressing the nucleic acid fragments of the invention can be used following their isolation by those skilled in the art. Heterologous promoters from other genes involved in seed oil biosynthesis, such as those for *B. napus* isocitrate lyase and malate synthase (Comai et al., Plant Cell (1989) 1:293–300), delta-9 desaturase from safflower (Thompson et al. Proc. Natl. Acad. Sci. USA (1991) 88:2578–2582) and castor (Shanklin et al., Proc. Natl. Acad. Sci. USA (1991) 88:2510–2514), acyl carrier protein (ACP) from Arabidopsis (Post-Beittenmiller et al., Nucl. Acids Res. (1989) 17:1777), *B. napus* (Safford et al., Eur. J. Biochem. (1988) 174:287–295), and *B. campestris* (Rose et al., Nucl. Acids Res. (1987) 15:7197), b-ketoacyl-ACP synthetase from barley (Siggaard-Andersen et al., Proc. Natl. Acad. Sci. USA (1991) 88:4114–4118), and oleosin from *Zea mays* (Lee et al., Proc. Natl. Acad. Sci. USA (1991) 88:6181–6185), soybean (Genbank Accession No: X60773) and *B. napus* (Lee et al., Plant Physiol. (1991) 96:1395–1397) will be of use. If the sequence of the corresponding genes is not disclosed or their promoter region is not identified, one skilled in the art can use the published sequence to isolate the corresponding gene and a fragment thereof containing the promoter. The partial protein sequences for the relatively-abundant enoyl-ACP reductase and acetyl-CoA carboxylase are also published (Slabas et al., Biochim. Biophys. Acta (1987) 877:271–280; Cottingham et al., Biochim. Biophys. Acta (1988) 954:201–207) and one skilled in the art can use these sequences to isolate the corresponding seed genes with their promoters. Similarly, the fragments of the present invention encoding fatty acid desaturases can be used to obtain promoter regions of the corresponding genes for use in expressing chimeric genes.

Attaining the proper level of expression of the nucleic acid fragments of the invention may require the use of different chimeric genes utilizing different promoters. Such chimeric genes can be transferred into host plants either together in a single expression vector or sequentially using more than one vector.

It is envisioned that the introduction of enhancers or enhancer-like elements into the promoter regions of either the native or chimeric nucleic acid fragments of the invention will result in increased expression to accomplish the invention. This would include viral enhancers such as that found in the 35S promoter (Odell et al., Plant Mol. Biol. (1988) 10:263–272), enhancers from the opine genes (Fromm et al., Plant Cell (1989) 1:977–984), or enhancers from any other source that result in increased transcription when placed into a promoter operably linked to the nucleic acid fragment of the invention.

Of particular importance is the DNA sequence element isolated from the gene for the a-subunit of b-conglycinin that can confer 40-fold seed-specific enhancement to a constitutive promoter (Chen et al., Dev. Genet. (1989) 10:112–122). One skilled in the art can readily isolate this element and insert it within the promoter region of any gene in order to obtain seed-specific enhanced expression with the promoter in transgenic plants. Insertion of such an element in any seed-specific gene that is expressed at different times than the b-conglycinin gene will result in expression in transgenic plants for a longer period during seed development.

The invention can also be accomplished by a variety of other methods to obtain the desired end. In one form, the invention is based on modifying plants to produce increased levels of fatty acid desaturases by virtue of introducing more than one copy of the foreign gene containing the nucleic acid fragments of the invention. In some cases, the desired level of polyunsaturated fatty acids may require introduction of foreign genes for more than one kind of fatty acid desaturase.

Any 3' non-coding region capable of providing a polyadenylation signal and other regulatory sequences that may be required for the proper expression of the nucleic acid fragments of the invention can be used to accomplish the invention. This would include 3' ends of the native fatty acid desaturase(s), viral genes such as from the 35S or the 19S cauliflower mosaic virus transcripts, from the opine synthesis genes, ribulose 1,5-bisphosphate carboxylase, or chlorophyll a/b binding protein. There are numerous examples in the art that teach the usefulness of different 3l non-coding regions.

Transformation Methods

Various methods of transforming cells of higher plants according to the present invention are available to those skilled in the art (see EPO Pub. 0 295 959 A2 and 0 318 341 A1). Such methods include those based on transformation vectors utilizing the Ti and Ri plasmids of Agrobacterium spp. It is particularly preferred to use the binary type of these vectors. Ti-derived vectors transform a wide variety of higher plants, including monocotyledonous and dicotyledonous plants (Sukhapinda et al., Plant Mol. Biol. (1987) 8:209–216; Potrykus, Mol. Gen. Genet. (1985) 199:183). Other transformation methods are available to those skilled in the art, such as direct uptake of foreign DNA constructs (see EPO Pub. 0 295 959 A2), techniques of electro-poration (Fromm et al., Nature (1986) (London) 319:791) or high-velocity ballistic bombardment with metal particles coated with the nucleic acid constructs (Kline et al., Nature (1987) (London) 327:70). Once transformed, the cells can be regenerated by those skilled in the art.

Of particular relevance are the recently described methods to transform foreign genes into commercially important crops, such as rapeseed (De Block et al., Plant Physiol. (1989) 91:694–701), sunflower (Everett et al., Bio/Technology (1987) 5:1201), and soybean (Christou et al., Proc. Natl. Acad. Sci USA (1989) 86:7500–7504.

Application to Molecular Breeding

The 1.6 kb insert obtained from the plasmid pSF2-169K was used as a radiolabelled probe on a Southern blot containing genomic DNA from soybean (*Glycine max* (cultivar Bonus) and *Glycine soja* (PI81762)) digested with one of several restriction enzymes. Different patterns of hybridization (polymorphisms) were identified in digests performed with restriction enzymes Hind III and Eco RI. These polymorphisms were used to map two pSF2-169 loci relative to other loci on the soybean genome essentially as described by Helentjaris et al., (Theor. Appl. Genet. (1986) 72:761–769). One mapped to linkage group 11 between 4404.00 and 1503.00 loci (4.5 cM and 7.1 cM from 4404.00 and 1503.00, respectively) and the other to linkage group 19 between 4010.00 and 5302.00 loci (1.9 cM and 2.7 cM from 4010.00 and 5302.00, respectively) [Rafalski, A and Tingey, S. (1993) in Genetic Maps, Ed. O'Brien, S. J.]. The use of restriction fragment length polymorphism (RFLP) markers in plant breeding has been well-documented in the art (Tanksley et al., Bio/Technology (1989) 7:257–264). Thus, the nucleic acid fragments of the invention can be used as RFLP markers for traits linked to expression of fatty acid desaturases. These traits will include altered levels of unsaturated fatty acids. The nucleic acid fragment of the invention can also be used to isolate the fatty acid desaturase gene from variant (including mutant) plants with altered levels of unsaturated fatty acids. Sequencing of these genes will reveal nucleotide differences from the normal gene that cause the variation. Short oligonucleotides designed around these differences may also be used in molecular breeding either as hybridization probes or in DNA-based diagnostics to follow the variation in fatty acids. Oligonucleotides based on differences that are linked to the variation may be used as molecular markers in breeding these variant oil traits.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Example 1

ISOLATION OF GENOMIC DNA FLANKING THE T-DNA SITE OF INSERTION IN *ARABIDOPSIS THALIANA* MUTANT LINE 658

Identification of an *Arabidopsis thaliana* T-DNA Mutant with High Oleic Acid Content A population of *Arabidopsis thaliana* (geographic race Wassilewskija) transformants containing the modified T-DNA of *Acrobacterium tumefaciens* was generated by seed transformation as described by Feldmann et al., (Mol. Gen. Genetics (1987) 208:1–9). In this population the transformants contain DNA sequences encoding the pBR322 bacterial vector, nopaline synthase, neomycin phosphotransferase (NPTII, confers kanamycin resistance), and b-lactamase (confers ampicillin resistance) within the T-DNA border sequences. The integration of the T-DNA into different areas of the chromosomes of individual transformants may cause a disruption of plant gene function at or near the site of insertion, and phenotypes associated with this loss of gene function can be analyzed by screening the population for the phenotype.

T3 seed was generated from the wild type seed treated with *Agrobacterium tumefaciens* by two rounds of self-fertilization as described by Feldmann et al., (Science (1989) 243:1351–1354). These progeny were segregating for the T-DNA insertion, and thus for any mutation resulting from the insertion. Approximately 10–12 leaves of each of 1700 lines were combined and the fatty acid content of each of the 1700 pooled samples was determined by gas chromatography of the fatty acyl methyl esters essentially as described by Browse et al., (Anal. Biochem. (1986) 152:141–145) except that 2.5% $H_2SO_4$ in methanol was used as the methylation reagent. A line designated "658" produced a sample that gave an altered fatty acid profile compared to those of lines 657 and 659 sampled at the same time (Table 8).

TABLE 8

| Fatty Acid Methyl Ester | 657 Leaf Pool | 659 Leaf Pool | 658 Leaf Pool |
| --- | --- | --- | --- |
| 16:0 | 14.4 | 14.1 | 13.6 |
| 16:1 | 4.4 | 4.6 | 4.5 |
| 16:2 | 2.9 | 2.2 | 2.7 |
| 16:3 | 13.9 | 13.3 | 13.9 |
| 18:0 | 1.0 | 1.1 | 0.9 |
| 18:1 | 2.6 | 2.5 | 4.9 |
| 18:2 | 14.0 | 13.6 | 12.8 |
| 18:3 | 42.9 | 46.1 | 44.4 |

Analysis of the fatty acid composition of 12 individual T3 seeds of line 658 indicated that the 658 pool was composed of seeds segregating in three classes: "high", "mid-range" and "low" classes with approximately, 37% (12 seeds), 21% (7 seeds), and 14% (3 seeds) oleic acid, respectively (Table 9).

TABLE 9

|  | "High" Class | "Mid-range" Class | "Low" Class |
| --- | --- | --- | --- |
| 16:0 | 8.9 | 8.7 | 9.3 |
| 16:1c | 2.0 | 1.6 | 2.6 |
| 18:0 | 4.5 | 4.3 | 4.4 |
| 18:1 | 37.0 | 20.7 | 14.4 |
| 18:2 | 8.0 | 24.9 | 27.7 |

TABLE 9-continued

| | "High" Class | "Mid-range" Class | "Low" Class |
|---|---|---|---|
| 18:3 | 10.6 | 14.3 | 13.6 |
| 20:1 | 25.5 | 21.6 | 20.4 |

Thus, the high oleic acid mutant phenotype segregates in an approximately Mendelian ratio. To determine the number of independently segregating T-DNA inserts in line 658, 200 T3 seeds were tested for their ability to germinate and grow in the presence of kanamycin [Feldman et al. (1989) Science 243:1351–1354]. In this experiment, only 4 kanamycin-sensitive individual plants were identified. The segregation ratio (approximately 50:1) indicated that line 658 harbored three T-DNA inserts. In this and two other experiments a total of 56 kanamycin-sensitive plants were identified; 53 of these were analyzed for fatty acid composition and at least seven of these displayed oleic acid levels that were higher than would be expected for wild type seedlings grown under these conditions.

In order to more rigorously test whether the mutation resulting in high oleic acid is the result of T-DNA insertion, Applicants identified a derivative line that was segregating for the mutant fatty acid phenotype as well as a single kanamycin resistance locus. For this, approximately 100 T3 plants were individually grown to maturity and seeds collected. One sample of seed from each T3 plant was tested for the ability to germinate and grow in the presence of kanamycin. In addition, the fatty acid compositions of ten additional individual seeds from each line were determined. A T3 plant, designated 658-75, was identified whose progeny seeds segregated 28 kanamycin-sensitive to 60 kanamycin-resistant and 7 with either low or intermediate oleic acid to 2 high oleic acid.

A total of approximately 400 T4 progeny seeds of the derivative line 658-75 were grown and the leaf fatty acid composition analyzed. A total of 91 plants were identified as being homozygous for the high oleic acid trait (18:2/18:1 less than 0.5). The remaining plants (18:2/18:1 more than 1.2) could not be definitively assigned to wild type and heterozygous classes on the basis of leaf fatty acid composition and thus could not be used to test linkage between the kanamycin marker and the fatty acid mutation. Eighty three of the 91 apparently homozygous high oleic acid mutant were tested for the presence of nopaline, another T-DNA marker, in leaf extracts (Errampalli et al. The Plant Cell (1991)3:149–157 and all 83 plants were positive for the presence of nopaline. This tight linkage of the mutant fatty acid phenotype and a T-DNA marker provides evidence that the high oleic acid trait in mutant 658 is the result of T-DNA insertion.

Plasmid Rescue and Analysis

One-half and one microgram of genomic DNA from the homozygous mutant plants of the 658-75 line, prepared from leaf tissue as described [Rogers, S. O. and A. J. Bendich (1985) Plant Molecular Biology 5:69–76], was digested with 20 units of either Bam HI or Sal I restriction enzyme (Bethesda Research Laboratory) in a 50 µL reaction volume according to the manufacturer's specifications. After digestion the DNA was extracted with buffer-saturated phenol (Bethesda Research Laboratory) followed by precipitation in ethanol. One-half to one microgram of Bam HI or Sal I digested genomic DNA was resuspended in 200 uL or 400 uL of ligation buffer containing 50 mM Tris-Cl, pH 8.0, 10 mM $MgCl_2$, 10 mM dithiothreitol, 1 mM ATP, and 4 units of T4 DNA ligase (Bethesda Research Laboratory). The dilute DNA concentration of approximate 2.5 ug/mL in the ligation reaction was chosen to facilitate circularization, as opposed to intermolecular joining. The reaction was incubated for 16 h at 16° C. Competent DH10B cells (Bethesda Research Laboratory) were transfected with 10 ng of ligated DNA per 100 µL of competent cells according to the manufacturer's specifications. Transformants from Sal I or Bam HI digests were selected on LB plates (10 g Bacto-tryptone, 5 g Bacto-yeast extract, 5 g NaCl, 15 g agar per liter, pH 7.4) containing 100 µg/mL ampicillin. After overnight incubation at 37° C. the plates were scored for ampicillin-resistant colonies.

A single ampicillin-resistant transformant derived from Bam HI-digested plant DNA was used to start a culture in 35 mL LB medium. (10 g Bacto-tryptone, 5 g yeast-extract, 5 g NaCl per liter) containing 25 mg/L ampicillin. The culture was incubated with shaking overnight at 37° C. and the cells were then collected by centrifugation at 1000×g for 10 min. Plasmid DNA, designated p658-1, was isolated from the cells by the alkaline lysis method of Birmbiom et al. [Nucleic Acid Research (1979) 7:1513–1523], as described in Sambrook et al., (Molecular Cloning, A Laboratory Manual, 2nd ed (1989) Cold Spring Harbor Laboratory Press). Plasmid p658-1 DNA was digested by restriction enzymes Bam HI,. Eco RI and Sal I (Bethesda Reseach Laboratory) and electrophoresed through a 1% agarose gel in 1×TBE buffer (0.089 M tris-borate, 0.002 M EDTA). The restriction pattern indicated the presence in this plasmid of the expected 14.2 kB T-DNA fragment and a 1.6 kB putative plant DNA/T-DNA border fragment.

Example 2

CLONING OF ARABIDOPSIS *THALIANA* MICROSOMAL DELTA-12 DESATURASE cDNA USING GENOMIC DNA FLANKING THE T-DNA SITE OF INSERTION IN *ARABIDOPSIS THALIANA* MUTANT LINE 658-75 AS A HYBRIDIZATION PROBE

Two hundred nanograms of the 1.6 kB Eco RI-Bam HI fragment from plasmid p658-1, following digestion of the plasmid with Eco RI and Bam HI and purification by electrophoresis in agarose, was radiolabelled with alpha [32P]-dCTP using a Random Priming Labeling Kit (Bethesda Research Laboratory) under conditions recommended by the manufacturer.

The radiolabeled DNA was used as a probe to screen an Arabidopsis cDNA library made from RNA isolated from above ground portions of various growth stages (Elledge et al., (1991) Proc. Nat. Acad. Sci., 88:1731–1735) essentially as described in Sambrook et al., (Molecular Cloning, A Laboratory Manual, 2nd ed. (1989), Cold Spring Harbor Laboratory Press). For this, approximately 17,000 plaque-forming units were plated on seven 90 mm petri plates containing a lawn of LE392 *E. coli* cells on NZY agar media (5 g NaCl, 2 g MgSO4–7 $H_2O$, 5 g yeast extract, 10 g casein acid hydrolysate, 13 g agar per liter). Replica filters of the phage plaques were prepared by adsorbing the plaques onto nitrocellulose filters (BA85, Schleicher and Schuell) then soaking successively for five min each in 0.5 M NaOH/1 M NaCl, 0.5 M Tris(pH 7.4)/1.5 M NaCl and 2×SSPE (0.36 M NaCl, 20 mM NaH2PO4(pH7.4), 20 mM EDTA (pH 7.4)). The filters were then air dried and baked for 2 h at 80° C. After baking the filters were wetted in 2×SSPE, and then incubated at 42° C. in prehybridization buffer (50% Formamide, 5×SSPE, 1% SDS, 5×Denhardt's Reagent, and 100 ug/mL denatured salmon sperm DNA) for 2 h. The filters were removed from the prehybridization buffer, and then transferred to hybridization buffer (50% Formamide, 5×SSPE, 1% SDS, 1×Denhardt's Reagent, and 100 ug/mL denatured salmon sperm DNA) containing the denatured radiolabeled probe (see above) and incubated for 40 h at 42° C. The filters were washed three times in 2×SSPE/0.2% SDS at 42° C. (15 min each) and twice in 0.2×SSPE/0,2% SDS at 55° C. (30 min each), followed by autoradiography on Kodak XAR-5 film with an intensifying screen at −80° C., overnight. Fifteen plaques were identified as positively-hybridizing on replica filters. Five of these were subjected to plaque purification essentially as described in Sambrook et al., (Molecular Cloning, A Laboratory Manual, 2nd ed. (1989), Cold Spring Harbor Laboratory Press). The lambda YES-R cDNA clones were converted to plasmid by propagating the phage in the E. coli BNN-132 cells, which expresses Cre protein that excises the cDNA insert as a double-stranded plasmid by cre-mediated in vivo site-speicifc recombination at a 'lox' sites present in the phage. Ampicillin-resistant plasmid clones containing cDNA inserts were grown in liquid culture, and plasmid DNA was prepared using the alkaline lysis method as previously described. The sizes of the resulting plasmids were analyzed by electrophoresis in agarose gels. The agarose gels were treated with 0.5 M NaOH/1 M NaCl, and 0.5 M Tris(pH 7.4), 1.5 M NaCl for 15 min each, and the gel was then dried completely on a gel drier at 65° C. The gel was hydrated in 2×SSPE and incubated overnight, at 42° C., in hybridization buffer containing the denatured radiolabeled probe, followed by washing as described above. After autoradiography, the inserts of four of the purified cDNA clones were found to have hybridized to the probe. Plasmid DNA from the hybridizing clones was purified by equilibration in a CsCl/ethidium bromide gradient (see above). The four cDNA clones were sequenced using Sequenase T7 DNA polymerase (US Biochemical Corp.) and the manufacturer's instructions, beginning with primers homologous to vector sequences that flank the cDNA insert. After comparing the partial sequences of the inserts obtained from the four clones, it was apparent that they each contained sequences in common. One cDNA clone, p92103, containing ca. 1.4 kB cDNA insert, was sequenced. The longest three clones were subcloned into the plasmid vector pBluescript (Stratagene). One of these clones, designated pSF2b, containing ca 1.2 kB cDNA insert was also sequenced serially with primers designed from the newly acquired sequences as the sequencing experiment progressed. The composite sequence derived from pSF2b and p92103 is shown in SEQ ID NO:1.

Example 3

CLONING OF PLANT FATTY ACID DESATURASE cDNAs USING THE *ARABIDOPSIS THALIANA* MICROSOMAL DELTA-12 DESATURASE cDNA CLONE AS A HYBRIDIZATION PROBE

An approximately 1.2 kb fragment containing the Arabidopsis delta-12 desaturase coding sequence of SEQ ID NO:1 was obtained from plasmid pSF2b. This plasmid was digested with EcoR I and the 1.2 kb delta-12 desaturase cDNA fragment was purified from the vector sequence by agarose gel electrophoresis. The fragment was radiolabelled with $^{32}P$ as previously described.

Cloning of a *Brassica napus* Seed cDNA Encoding Microsomal Delta-12 Fatty Acid Desaturase The radiolabelled probe was used to screen a *Brassica napus* seed cDNA library. In order to construct the library, *Brassica napus* seeds were harvested 20–21 days after pollination, placed in liquid nitrogen, and polysomal RNA was isolated following the procedure of Kamalay et al., (Cell (1980) 19:935–946). The polyadenylated mRNA fraction was obtained by affinity chromatography on oligo-dT cellulose (Aviv et al., Proc. Natl. Acad. Sci. USA (1972) 69:1408–1411). Four micrograms of this mRNA were used to construct a seed cDNA library in lambda phage (Uni-ZAP™ XR vector) using the protocol described in the ZAP-cDNA™ Synthesis Kit (1991 Stratagene Catalog, Item #200400). Approximately 600,000 clones were screened for positively hybridizing plaques using the radiolabelled EcoR I fragment from pSF2b as a probe essentially as described in Sambrook et al., (Molecular Cloning: A Laboratory Manual, 2nd ed. (1989) Cold Spring Harbor Laboratory Press) except that low stringency hybridization conditions (50 mM Tris, pH 7.6, 6×SSC, 5×Denhardt's, 0.5% SDS, 100 μg denatured calf thymus DNA and 50° C.) were used and post-hybridization washes were performed twice with 2×SSC, 0.5% SDS at room temperature for 15 min, then twice with 0.2×SSC, 0.5% SDS at room temperature for 15 min, and then twice with 0.2×SSC, 0.5% SDS at 50° C. for 15 min. Ten positive plaques showing strong hybridization were picked, plated out, and the screening procedure was repeated. From the secondary screen nine pure phage plaques were isolated. Plasmid clones containing the cDNA inserts were obtained through the use of a helper phage according to the in vivo excision protocol provided by Stratagene. Double-stranded DNA was prepared using the alkaline lysis method as previously described, and the resulting plasmids were size-analyzed by electrophoresis in agarose gels. The largest one of the nine clones, designated pCF2-165D, contained an approximately 1.5 kb insert which was sequenced as described above. The sequence of 1394 bases of the cDNA insert of pCF2-165D is shown in SEQ ID NO:3. Contained in the insert but not shown in SEQ ID NO:3 are approximately 40 bases of the extreme 5' end of the 5' non-translated region and a poly A tail of about 38 bases at the extreme 3' end of the insert.

Cloning of a Soybean Seed cDNA Encoding Microsomal Delta-12 Fatty Acid Desaturase A cDNA library was made as follows: Soybean embryos (ca. 50 mg fresh weight each) were removed from the pods and frozen in liquid nitrogen. The frozen embryos were ground to a fine powder in the presence of liquid nitrogen and then extracted by Polytron homogenization and fractionated to enrich for total RNA by the method of Chirgwin et al. (Biochemistry (1979) 18:5294–5299). The nucleic acid fraction was enriched for poly $A^+RNA$ by passing total RNA through an oligo-dT cellulose column and eluting the poly $A^+RNA$ with salt as described by Goodman et al. (Meth. Enzymol. (1979) 68:75–90). cDNA was synthesized from the purified poly $A^+RNA$ using cDNA Synthesis System (Bethesda Research Laboratory) and the manufacturer's instructions. The resultant double-stranded DNA was methylated by Eco RI DNA methylase (Promega) prior to filling-in its ends with T4 DNA polymerase (Bethesda Research Laboratory) and blunt-end ligation to phosphorylated Eco RI linkers using T4 DNA ligase (Pharmacia). The double-stranded DNA was digested with Eco RI enzyme, separated from excess linkers by passage through a gel filtration column (Sepharose CL-4B), and ligated to lambda ZAP vector (Stratagene) according to manufacturer's instructions. Ligated DNA was packaged into phage using the Gigapack packaging extract (Stratagene) according to manufacturer's instructions. The resultant cDNA library was amplified as per Stratagene's instructions and stored at −80° C.

Following the instructions in the Lambda ZAP Cloning Kit Manual (Stratagene), the cDNA phage library was used to infect *E. coli* BB4 cells and approximately 600,000 plaque forming units were plated onto 150 mm diameter petri plates. Duplicate lifts of the plates were made onto nitrocellulose filters (Schleicher & Schuell). The filters were prehybridized in 25 mL of hybridization buffer consisting of 6×SSPE, 5×Denhardt's solution, 0.5% SDS, 5% dextran sulfate and 0.1 mg/mL denatured salmon sperm DNA (Sigma Chemical Co.) at 50° C. for 2 h. Radiolabelled probe prepared from pSF2b as described above was added, and allowed to hybridize for 18 h at 50° C. The filters were washed exactly as described above. Autoradiography of the filters indicated that there were 14 strongly hybridizing plaques. The 14 plaques were subjected to a second round of screening as before. Numerous, strongly hybridizing plaques were observed on 6 of the 14 filters, and one, well-isolated from other phage, was picked from each of the six plates for further analysis.

Following the Lambda ZAP Cloning Kit Instruction Manual (Stratagene), sequences of the pBluescript vector, including the cDNA inserts, from the purified phages were excised in the presence of a helper phage and the resultant phagemids were used to infect *E. coli* XL-1 Blue cells. DNA from the plasmids was made by the Promega "Magic Miniprep" according to the. manufacturers instructions. Restriction analysis indicated that the plasmids contained inserts ranging in size from 1 kb to 2.5 kb. The alkali-denatured double-stranded DNA from one of these, designated pSF2-169K contained an insert of 1.6 kb, was sequenced as described above. The nucleotide sequence of the cDNA insert in plasmid pSF2-169K shown in SEQ ID NO:5.

Cloning of a Corn (*Zea mays*) cDNA Encoding Seed Microsomal Delta-12 Fatty Acid Desaturase Corn microsomal delta-12 desaturase cDNA was isolated using a PCR approach. For this, a cDNA library was made to poly A+ RNA from developing corn embryos in Lambda ZAP II vector (Stratagene). 5–10 ul of this library was used as a template for PCR using 100 pmol each of two sets of degenerate oligomers NS3 (SEQ ID NO:13) and equimolar amounts of RB5a/b (that is, equimolar amounts of SEQ ID NOS:16/17) as sense and antisense primers, respectively. NS3 and RB5a/b correspond to stretches of amino acids 101–109 and 318–326, respectively, of SEQ ID NO:2, which are conserved in most microsomal delta-12 desaturases (SEQ ID NOS:2, 4, 6, 8). PCR was carried out using the PCR 35 kit (Perkin-Elmer) using 40 cycles of 94° C. 1 min, 45° C., 1 min, and 55° C., 2 min. Analyses of the PCR products on an agarose gel showed the presence of a product of the expected size (720 bp), which was absent in control reactions containing either the sense or antisense primers alone. The PCR product fragment was gel purified and then used as a probe for screening the same corn cDNA library at 60° C. as described above. One positively-hybridizing plaque was purified and partial sequence determination of its cDNA showed it to be a nucleotide sequence encoding microsomal delta-12 desaturase but truncated at the 3' end. The cDNA insert encoding the partial desaturase was gel isolated and used to probe the corn cDNA library again. Several positive plaques were recovered and characterized. DNA sequence analysis revealed that all of these clones seem to represent the same sequence with the different length of 5' or 3' ends. The clone containing the longest insert, designated pFad2#1, was sequenced completely. SEQ ID NO:7 shows the 5' to 3' nucleotide sequence of 1790 base pairs of corn (*Zea mays*) cDNA which encodes microsomal delta-12 desaturase in plasmid pFad2#1. Nucleotides 165 to 167 and nucleotides 1326 to 1328 are, respectively, the putative initiation codon and the termination codon of the open reading frame (nucleotides 164 to 1328). SEQ ID NO:8 is the 387 amino acid protein sequence deduced from the open reading frame (nucleotides 164 to 1328) in SEQ ID NO:7. The deduced amino acid sequence of the polypeptide shared overall identities of 71%, 40%, and 38% to Arabidopsis microsomal delta-12 desaturase, Arabidopsis microsomal delta-15 desaturase, and Arabidopsis plastid delta-15 desaturase, respectively. Furthermore, it lacked an N-terminal amino acid extension that would indicate it is a plastid enzyme. Based on these considerations, it is concluded that it encodes a microsomal delta-12 desaturase.

Cloning of a cDNA Encoding A Microsomal Delta-12 Desaturase and of cDNAs Encoding Microsomal Delta-12 Desaturase-Related Enzymes from Castor Bean Seed Castor microsomal delta-12 desaturase cDNA was isolated using a RT-PCR approach. Polysomal mRNA was isolated from castor beans of stages I–II (5–10 DAP) and also from castor beans of stages IV–V (20–25 DAP). Ten ng of each mRNA was used for separate RT-PCR reactions, using the Perkin-Elmer RT-PCR kit with the reagent concentration as recommended by the kit protocol. The reverse transcriptase reaction was primed with random hexamers and the PCR reaction with 100 pmol each of the degenerate delta-12 desaturase primers NS3 and NS9 (SEQ ID NOS:13 and 14, respectively). The reverse transcriptase reaction was incubated at 25° C. for 10 min, 42° C. for 15 min, 99° C. for 5 min and 5° C. for 5 min. The PCR reaction was incubated at 95° C. for 2 min followed by 35 cycles of 95° C. for 1 min/50° C. for 1 min. A final incubation at 60° C. for 7 min completed the reaction. A DNA fragment of 720 bp was amplified from both stage I–II and stage IV–V mRNA. The amplified DNA fragment from one of the reactions was gel purified and cloned into a pGEM-T vector using the Promega pGEM-T PCR cloning kit to create the plasmid pRF2-1C. The 720 bp insert in pRF2-1C was sequenced, as described above, and the resulting DNA sequence is shown in SEQ ID NO:9. The DNA sequence in SEQ ID NO:9 contains an open-reading frame encoding 219 amino acids (SEQ ID NO:10), which has 81% identity (90% similarity) with amino acids 135 to 353 of the Arabidopsis microsomal delta-12 desaturase described in SEQ ID NO:2. The cDNA insert in pRF2-1C is therefore a 673 bp fragment of a full-length cDNA encoding a castor bean seed microsomal delta-12 desaturase. The full length castor bean seed microsomal delta-12 desaturase cDNA may isolated by screening a castor seed cDNA library, at 60° C., with the labeled insert of pRF2-1C as described in the example above. The insert in pRF2-1C may also be used to screen castor bean libraries at lower temperatures to isolate delta-12 desaturase related sequences, such as the delta-12 hydroxylase.

A cDNA library made to poly A+ mRNA isolated from developing castor beans (stages IV–V, 20–25 DAP) was screened as described above. Radiolabeled probe prepared from pSF2b or pRF2-1C, as described above, were added, and allowed to hybridize for 18 h at 50° C. The filters were washed as described above. Autoradiography of the filters indicated that there were numerous hybridizing plaques, which appeared either strongly hybridising or weakly hybridising. Three of the strongly hybridisng plaques (190A-41, 190A-42 and 190A-44) and three of the weakly hybridising plaques, (190B-41, 190b-43 and 197c-42), were plaque purified using the methods described above. The cDNA insert size of the purified phages were determined by PCR amplication of the insert using phage as template and lambda-gt11 oligomers (Clontech lambda-gt11 Amplimers) for primers. The PCR-amplified inserts of the amplified phages were subcloned into pBluescript (Pharmacia) which had been cut with Eco RI and filled in with Klenow (Sambrook et al. (Molecular Cloning, A Laboratory Approach, 2nd. ed. (1989) Cold Spring Harbor Laboratory Press). The resulting plasmids were called pRF190a-41, pRF190a-42, pRF190a-44, pRF190b-41, pRF190b-43 and pRF197c-42. All of the inserts were about 1.1 kb with the exception of pRF197c-42 which was approx. 1.5 kb. The inserts in the plasmids were sequenced as described above. The insert in pRF190b-43 did not contain any open reading frame and was not identified. The inserts in pRF190a-41, pRF190a-42, pRF190a-44 and pRF190b-41 were identical. The insert in pRF197c-42 contained all of the nucleotides of the inserts in pRF190a-41, pRF190a-42, pRF190a-44 and pRF190b-41 plus an additional approx. 400 bp. It was deduced therefore that the insert in pRF197c-42 was a longer version of the inserts in pRF190a-41, pRF190a-42, pRF190a-44 and pRF190b-41 and all were derived from the same full-length mRNA. The complete cDNA sequence of the insert in plasmid pRF197c-42 is shown in SEQ ID NO:11. The deduced amino acid sequence of SEQ ID NO:11, shown in SEQ ID NO:12, is 78.5% identical (90% similarity) to the castor microsomal delta-12 desaturase described above (SEQ ID NO:10) and 66% identical (80% similarity) to the Arabidopsis delta-12 desaturase amino acid sequence in SEQ ID NO:2. These similarities confirm that pRF197c-42 is a castor bean seed cDNA that encodes a microsomal delta-12 desaturase or a microsomal delta-12 desaturase-related enzyme, such as a delta-12 hydroxylase. Specific PCR primers for pRF2-1C and pRF197c-42 were made. For pRF2-1c the upstream primer was bases 180 to 197 of the cDNA sequence in SEQ ID NO:9. For pRF197c-42 the upstream primer was bases 717 to 743 of the cDNA sequence in SEQ ID NO:11. A common downstream primer was made corresponding to the exact complement of the nucleotides 463 to 478 of the sequence described in SEQ ID NO:9. Using RT-PCR with random hexamers and the above primers, and the incubation temperatures described above, it was observed that mRNA which gave rise to the cDNA contained in pRF2-1C is present in both Stage I–II and Stage IV–V castor bean seeds whereas mRNA which gave rise to the cDNA contained in plasmid pRF197c-42 is present only in Stage IV–V castor bean seeds, i.e., it is only expressed in tissue actively synthesizing ricinoleic acid. Thus it is possible that this cDNA encodes a delta-12 hydroxylase.

Clones such as pRF2-1C and pRF197c-42, and other clones from the differential screening, which, based on their DNA sequence, are less related to castor bean seed microsomal delta-12 desaturases and are not any of the known fatty-acid desaturases described above or in WO 9311245, may be expressed, for example, in soybean embryos or another suitable plant tissue, or in a microorganism, such as yeast, which does not normally contain ricinoleic acid, using suitable expression vectors and transformation protocols. The presence of novel ricinoleic acid in the transformed tissue(s) expressing the castor cDNA would confirm the identity of the castor cDNA as DNA encoding for an oleate hydroxylase.

Example 4

USE OF THE ARABIDOPSIS THALIANA DELTA-12 DESATURASE GENOMIC CLONE AS A RESTRICTION FRAGMENT LENGTH POLYMORPHISM (RFLP) MARKER TO MAP THE DELTA-12 DESATURASE LOCUS IN ARABIDOPSIS

The gene encoding Arabidopsis microsomal delta-12 desaturase was used to map the genetic locus encoding the microsomal delta-12 desaturase of *Arabidopsis thaliana*. pSF2b cDNA insert encoding Arabidopsis microsomal delta-12 desaturase DNA was radiolabeled and used to screen an Arabidopsis genomic DNA library. DNA from several pure strongly-hybridizing phages was isolated. Southern blot analysis of the DNA from different phages using radiolabeled pSF2b cDNA insert as the probe identified a 6 kb Hind III insert fragment to contain the coding region of the gene. This fragment was subcloned in pBluescript vector to result in plasmid pAGF2-6 and used for partial sequence determination. This sequence (SEQ ID NO:15) confirmed that it is the microsomal delta-12 desaturase gene. DNA from two phages was isolated and labelled with $^{32}$P using a random priming kit from Pharmacia under conditions recommended by the manufacturer. The radioactive DNA was used to probe a Southern blot containing genomic DNA from *Arabidopsis thaliana* (ecotype Wassileskija and marker line W100 ecotype Landesberg background) digested with one of several restriction endonucleases. Following hybridization and washes under standard conditions (Sambrook et al., Molecular Cloning: A Laboratory Manual, 2nd ed. (1989) Cold Spring Harbor Laboratory Press), autoradiograms were obtained. A different pattern of hybridization (polymorphism) was identified in Hind III-digested genomic DNAs using one of the phage DNAs. This polymorphism was located to a 7 kB Hind III fragment in the phage DNA that revealed the polymorphism. The 7 kb fragment was subcloned in pBluescript vector to result in plasmid pAGF2-7. Plasmid pAGF2-7 was restricted with Hind III enzyme.and used as a radiolabelled probe to map the polymorphism essentially as described by Helentjaris et al., (Theor. Appl. Genet. (1986) 72:761–769). The radiolabelled DNA fragment was applied as described above to Southern blots of Hind III-digested genomic DNA isolated from 117 recombinant inbred progeny (derived from single-seed descent lines to the $F_6$ generation) resulting from a cross between *Arabidopsis thaliana* marker line W100 and ecotype Wassileskija (Burr et al., Genetics (1988) 118:519–526). The bands on the autoradiograms were interpreted as resulting from inheritance of either paternal (ecotype Wassileskija) or maternal (marker line W100) DNA or both (a heterozygote). The resulting segregation data were subjected to genetic analysis using the computer program Mapmaker (Lander et al., Genomics (1987) 1:174–181). In conjunction with previously obtained segregation data for 63 anonymous RFLP markers and 9 morphological markers in *Arabidopsis thaliana* (Chang et al., Proc. Natl. Acad. Sci. USA (1988) 85:6856–6860; Nam et al., Plant Cell (1989) 1:699–705), a single genetic locus was positioned corresponding to the microsomal delta-12 desaturase gene. The location of the microsomal delta-12 desaturase gene was thus determined to be 13.6 cM proximal to locus c3838, 9.2 cM distal to locus 1At228, and 4.9 cM proximal to FadD locus on chromosome 3 [Koorneef, M. et. al. (1993) in Genetic Maps, Ed. O'Brien, S. J.; Yadav et al. (1993) Plant Physiology 103:467–476.]

Example 5

USE OF SOYBEAN MICROSOMAL DELTA-12 DESATURASE cDNA SEQUENCE AS A RESTRICTION FRAGMENT LENGTH POLYMORPHISM (RFLP) MARKER

The 1.6 kb insert obtained from the plasmid pSF2-169K as previously described was radiolabelled with $^{32}$P using a Random Priming Kit from Bethesda Research Laboratories under conditions recommended by the manufacturer. The resulting radioactive probe was used to probe a Southern blot (Sambrook et al., Molecular Cloning: A Laboratory Manual, 2nd Ed. (1989) Cold Spring Harbor Laboratory Press) containing genomic DNA from soybean (*Glycine max* (cultivar Bonus) and *Glycine soja* (PI81762)) digested with one of several restriction enzymes. After hybridization and washes under low stringency conditions (50 mM Tris, pH 7.5, 6×SSPE, 10% dextran sulfate, 1% SDS at 56° C. for the hybridization and initial washes, changing to 2×SSPE and 0.1% SDS for the final wash), autoradiograms were obtained, and different patterns of hybridization (polymorphisms) were identified in digests performed with restriction enzymes Hind III and Eco RI. These polymorphisms were used to map two pSF2-169k loci relative to other loci on the soybean genome essentially as described by Helentjaris et al., (Theor. Appl. Genet. (1986) 72:761–769). The map positions of the polymorphisms were determined to be in linkage group 11 between 4404.00 and 1503.00 loci (4.5 cM and 7.1 cM from 4404.00 and 1503.00, respectively) and linkage group 19 between 4010.00 and 5302.00 loci (1.9 cM and 2.7 cM from 4010.00 and 5302.00, respectively) [Rafalski, A. and Tingey, S. (1993) in Genetic Maps, Ed. 0' Brien, S. J.].

Example 6

EXPRESSION OF MICROSOMAL DELTA-12 DESATURASE IN SOYBEANS

Construction of Vectors for Transformation of *Glycine max* for Reduced Expression of Microsomal Delta-12 Desaturases in Developing Soybean Seeds Plasmids containing the antisense *G. max* microsomal delta-12 desaturase cDNA sequence under control of the soybean Kunitz Trypsin Inhibitor 3 (KTi3) promoter (Jofuku and Goldberg, Plant Cell (1989) 1:1079–1093) the *Phaseblus vulgaris* 7S seed storage protein (phaseolin) promoter (Sengupta-Gopalan et al., Proc. Natl. Acad. Sci. USA (1985) 82:3320–3324; Hoffman et al., Plant Mol. Biol. (1988) 11:717–729) and soybean beta-conglycinin promoter (Beachy et al., EMBO J. (1985) 4:3047–3053), were constructed. The construction of vectors expressing the soybean delta-12 desaturase antisense cDNA under the control of these promoters was facilitated by the use of the following plasmids: pML70, pCW108 and pCW109A.

The pML70 vector contains the KTi3 promoter and the KTi3 3' untranslated region and was derived from the commercially available vector pTZ18R (Pharmacia) via the intermediate plasmids pML51, pML55, pML64 and pML65. A 2.4 kb Bst BI/Eco RI fragment of the complete soybean KTi3 gene (Jofuku and Goldberg (1989) Plant Cell 1:1079–1093), which contains all 2039 nucleotides of the 5' untranslated region and 390 bases of the coding sequence of the KTi3 gene ending at the Eco RI site corresponding to bases 755 to 761 of the sequence described in Jofuku et al (1989) Plant Cell 1:427–435, was ligated into the Acc I/Eco RI sites of pTZ18R to create the plasmid pML51. The plasmid pML51 was cut with Nco I, filled in using Klenow, and religated, to destroy an Nco I site in the middle of the 5' untranslated region of the KTi3 insert, resulting in the plasmid pML55. The plasmid pML55 was partially digested with Xmn I/Eco RI to release a 0.42 kb fragment, corresponding to bases 732 to 755 of the above cited sequence, which was discarded. A synthetic Xmn I/Eco RI linker containing an Nco I site, was constructed by making a dimer of complementary synthetic oligonucleotides consisting of the coding sequence for an Xmn I site (5'-TCTTCC-3') and an Nco I site (5'-CCATGGG-3') followed directly by part of an Eco RI site (5'-GAAGG-3'). The Xmn I and Nco I/Eco RI sites were linked by a short intervening sequence (5'-ATAGCCCCCCAA-3'). This synthetic linker was ligated into the Xmn I/Eco RI sites of the 4.94 kb fragment to create the plasmid pML64. The 3' untranslated region of the KTi3 gene was amplified from the sequence described in Jofuku et al (Ibid.) by standard PCR protocols (Perkin Elmer Cetus, GeneAmp PCR kit) using the primers ML51 and ML52. Primer ML51 contained the 20 nucleotides corresponding to bases 1072 to 1091 of the above cited sequence with the addition of nucleotides corresponding to Eco RV (5'-GATATC-3'), Nco I (5'-CCATGG-3'), Xba I (5'-TCTAGA-3'), Sma I (5'-CCCGGG-3') and Kpn I (5'-GGTACC-3') sites at the 5' end of the primer. Primer ML52 contained to the exact compliment of the nucleotides corresponding to bases 1242 to 1259 of the above cited sequence with the addition of nucleotides corresponding to Sma I (5'-CCCGGG-3'), Eco RI (5'-GAATTC-3'), Bam HI (5'-GGATCC-3') and Sal I (5'-GTCGAC-3') sites at the 5' end of the primer. The PCR-amplified 3' end of the KTi3 gene was ligated into the Nco I/Eco RI sites of pML64 to create the plasmid pML65. A synthetic multiple cloning site linker was constructed by making a dimer of complementary synthetic oligonucleotides consisting of the coding sequence for Pst I (5'-CTGCA-3'), Sal I (5'-GTCGAC-3'), Bam HI (5'-GGATCC-3') and Pst I (5'-CTGCA-3') sites. The linker was ligated into the Pst I site (directly 5' to the KTi3 promoter region) of pML65 to create the plasmid pML70.

The 1.46 kb Sma I/Kpn I fragment from pSF2-169K (soybean delta-12 desaturase cDNA described above) was ligated into the corresponding sites in pML70 resulting in the plasmid pBS10. The desaturase cDNA fragment was in the reverse (antisense) orientation with respect to the KTi3 promoter in pBS10. The plasmid pBS10 was digested with Bam HI and a 3.47 kb fragment, representing the KTi3 promoter/antisense desaturase cDNA/KTi3-3' end transcriptional unit was isolated by agarose gel electrophoresis. The vector pML18 consists of the non-tissue specific and constitutive cauliflower mosaic virus (35S) promoter (Odell et al., Nature (1985) 313:810–812; Hull et al., Virology (1987) 86:482–493), driving expression of the neomycin phosphotransferase gene described in (Beck et al. (1982) Gene 19:327–336) followed by the 3' end of the nopaline synthase gene including nucleotides 848 to 1550 described by (Depicker et al. (1982) J. Appl. Genet. 1:561–574). This transcriptional unit was inserted into the commercial cloning vector pGEM9Z (Gibco-BRL) and is flanked at the 5' end of the 35S promoter by the restriction sites Sal I, Xba I, Bam HI and Sma I in that order. An additional Sal I site is present at the 3' end of the NOS 3' sequence and the Xba I, Bam HI and Sal I sites are unique. The 3.47 kb transcriptional unit released from pBS10 was ligated into the Bam HI site of the vector pML18. When the resulting plasmids were double digested with Sma I and Kpn I, plasmids containing inserts in the desired orientation yielded 3 fragments of 5.74, 2.69 and 1.46 kb. A plasmid with the transcriptional unit in the correct orientation was selected and was designated pBS13.

The pCW108 vector contains the bean phaseolin promoter and 3' untranslated region and was derived from the commercially available pUC18 plasmid (Gibco-BRL) via plasmids AS3 and pCW104. Plasmid AS3 contains 495 base pairs of the bean (Phaseolus vulgaris) phaseolin (7S seed storage protein) promoter starting with 5'-TGGTCTTTTGGT-3' followed by the entire 1175 base pairs of the 3' untranslated region of the same gene (see sequence descriptions in Doyle et al., (1986) J. Biol. Chem. 261:9228–9238 and Slightom et al., (1983) Proc. Natl. Acad. Sci. USA, 80:1897–1901. Further sequence description may be found in WO 9113993) cloned into the Hind III site of pUC18. The additional cloning sites of the pUC18 multiple cloning region (Eco RI, Sph I, Pst I and Sal I) were removed by digesting with Eco RI and Sal I, filling in the ends with Klenow and religating to yield the plasmid pCW104. A new multiple cloning site was created between the 495 bp of the 5' phaseolin and the 1175 bp of the 3' phaseolin by inserting a dimer of complementary synthetic oligonucleotides consisting of the coding sequence for a Nco I site (5'-CCATGG-3') followed by three filler bases (5'-TAG-3'), the coding sequence for a Sma I site (5'-CCCGGG-3'), the last three bases of a Kpn I site (5'-TAC-3'), a cytosine and the coding sequence for an Xba I site (5'-TCTAGA-3') to create the plasmid pCW108. This plasmid contains unique Nco I, Sma I, Kpn I and Xba I sites directly behind the phaseolin promoter. The 1.4 kb Eco RV/Sma I fragment from pSF2-169K was ligated into the Sma I site of the commercially available phagemid pBC SK+ (Stratagene). A phagemid with the cDNA in the desired orientation was selected by digesting with Pfl MI/Xho I to yield fragments of approx. 1 kb and 4 kb and designated pM1-SF2. The 1.4 kb Xmn I/Xba I fragment from pM1-SF2 was inserted into the Sma I/Xba I sites of pCW108 to yield the plasmid pBS11, which has the soybean delta-12 desaturase cDNA in the reverse (3'–5') orientation behind the phaseolin promoter. The plasmid pBS11 was digested with Bam HI and a 3.07 kb fragment, representing the phaseolin promoter/antisense desaturase cDNA/phaseolin 3' end transcriptional unit was isolated by agarose gel electrophoresis and ligated into the Hind III site of pML18 (described above). When the resulting plasmids were digested with Xba I, plasmids containing inserts in the desired orientation yielded 2 fragments of 8.01 and 1.18 kb. A plasmid with the transcriptional unit in the correct orientation was selected and was designated pBS14.

The vector pCW109A contains the soybean b-conglycinin promoter sequence and the phaseolin 3' untranslated region and is a modified version of vector pCW109 which was derived from the commercially available plasmid pUC18 (Gibco-BRL). The vector pCW109 was made by inserting into the Hind III site of the cloning vector pUC18 a 555 bp 5' non-coding region (containing the promoter region) of the b-conglycinin gene followed by the multiple cloning sequence containing the restriction endonuclease sites for Nco I, Sma I, Kpn I and Xba I, as described for pCW108 above, then 1174 bp of the common bean phaseolin 3' untranslated region into the Hind III site (described above). The b-conglycinin promoter region used is an allele of the published b-conglycinin gene (Doyle et al., J. Biol. Chem. (1986) 261:9228–9238) due to differences at 27 nucleotide positions. Further sequence description of this gene may be found in Slightom (WO 9113993). To facilitate use in antisense constructions, the Nco I site and potential translation start site in the plasmid pCW109 was destroyed by digestion with Nco I, mung bean exonuclease digestion and re-ligation of the blunt site to give the modified plasmid pCW109A. The plasmid pCW109A was digested with Hind III and the resulting 1.84 kb fragment, which contained the b-conglycinin/antisense delta-12 desaturase cDNA/phaseolin 3' untranslated region, was gel isolated. The plasmid pML18 (described above) was digested with Xba I, filled in using Klenow and religated, in order to remove the Xba I site. The resulting plasmid was designated pBS16. The 1.84 kb fragment of plasmid pCW109A (described above) was ligated into the Hind III site of pBS16. A plasmid containing the insert in the desired orientation yielded a 3.53 kb and 4.41 kb fragment when digested with Kpn I and this plasmid was designated pCST2. The Xmn I/Xba I fragment of pML1-SF2 (described above) was ligated into the Sma I/Xba I sites of pCST2 to yield the vector pST11.

Transformation Of Somatic Soybean Embryo Cultures and Regeneration Of Soybean Plants Soybean embryogenic suspension cultures were maintained in 35 mL liquid media (SB55 or SBP6) on a rotary shaker, 150 rpm, at 28° C. with mixed florescent and incandescent lights on a 16:8 h day/night schedule. Cultures were subcultured every four weeks by inoculating approximately 35 mg of tissue into 35 mL of liquid medium.

Soybean embryogenic suspension cultures were transformed with pCS3FdST1R by the method of particle gun bombardment (see Kline et al. (1987) Nature (London) 327:70). A DuPont Biolistic PDS1000/HE instrument (helium retrofit) was used for these transformations.

To 50 mL of a 60 mg/mL 1 mm gold particle suspension was added (in order); 5 uL DNA(1 ug/uL), 20 uL spermidine (0.1 M), and 50 ul $CaCl_2$ (2.5 M). The particle preparation was agitated for 3 min, spun in a microfuge for 10 sec and the supernatant removed. The DNA-coated particles were then washed once in 400 uL 70% ethanol and re suspended in 40 uL of anhydrous ethanol. The DNA/particle suspension was sonicated three times for 1 sec each. Five uL of the DNA-coated gold particles were then loaded on each macro carrier disk.

Approximately 300–400 mg of a four week old suspension culture was placed in an empty 60×15 mm petri dish and the residual liquid removed from the tissue with a pipette. For each transformation experiment, approximately 5–10 plates of tissue were normally bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Eleven days post bombardment, the liquid media was exchanged with fresh SB55 containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as independent transformation event. These suspensions can then be maintained as suspensions of embryos clustered in an immature developmental stage through subculture or regenerated into whole plants by maturation and germination of individual somatic embryos.

Transformed embryogenic clusters were removed from liquid culture and placed on a solid agar media (SB103) containing no hormones or antibiotics. Embryos were cultured for eight weeks at 26° C. with mixed florescent and incandescent lights on a 16:8 h day/night schedule. During this period, individual embryos were removed from the clusters and analyzed at various stages of embryo development After eight weeks somatic embryos become suitable for germination. For germination, eight week old embryos were removed from the maturation medium and dried in empty petri dishes for 1 to 5 days. The dried embryos were then planted in SB71-1 medium were they were allowed to germinate under the same lighting and germination conditions described above. Germinated embryos were transferred to sterile soil and grown to maturity for seed collection.

TABLE 10

| Media: SB55 and SBP6 Stock Solutions (g/L): | |
|---|---|
| MS Sulfate 100X Stock | |
| MgSO$_4$ 7H2O | 37.0 |
| MnSO$_4$ H2O | 1.69 |
| ZnSO$_4$ 7H2O | 0.86 |
| CuSO$_4$ 5H2O | 0.0025 |
| MS Halides 100X Stock | |
| CaCl$_2$ 2H$_2$O | 44.0 |
| KI | 0.083 |
| CoCl$_2$ 6H$_2$O | 0.00125 |
| KH$_2$PO$_4$ | 17.0 |
| H$_3$BO$_3$ | 0.62 |
| Na$_2$MoO$_4$ 2H$_2$O | 0.025 |
| MS FeEDTA 100X Stock | |
| Na$_2$EDTA | 3.724 |
| FeSO$_4$ 7H$_2$O | 2.784 |
| B5 Vitamin Stock | |
| 10 g m-inositol 100 mg nicotinic acid 100 mg pyridoxine HCl 1 g thiamine | |
| SB55 (per Liter) | |
| 10 mL each MS stocks 1 mL B5 Vitamin stock 0.8 g NH$_4$NO$_3$ 3.033 g KNO$_3$ 1 mL 2,4-D (10 mg/mL stock) 60 g sucrose 0.667 g asparagine pH 5.7 For SBP6- substitute 0.5 mL 2,4-D | |
| SB103 (per Liter) | |
| MS Salts 6% maltose 750 mg MgCl$_2$ 0.2% Gelrite pH 5.7 | |
| SB71-1 (per liter) | |
| B5 salts 1 ml B5 vitamin stock 3% sucrose 750 mg MgCl2 0.2% gelrite pH 5.7 | |

Analysis Of Transgenic *Glycine Max* Embryos and Seeds Containing An Antisense Delta-15 Desaturase: Demonstration That The Phenotype Of Transgenic Soybean Somatic Embryos Is Predictive Of The Phenotype Of Seeds Derived From Plants Regenerated From Those Embryos While in the globular embryo state in liquid culture as described above, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins (alpha' subunit of beta-conglycinin, Kunitz Trypsin Inhibitor 3 and Soybean Seed Lectin) are essentially absent. Upon transfer to hormone free media to allow differentiation to the maturing somatic embryo state as described above, triacylglycerol becomes the most abundant lipid class. As well, mRNAs for alpha'-subunit of beta-conglycinin, Kunitz Trypsin Inhibitor 3 and Soybean Seed Lectin become very abundant messages in the total mRNA population. In these respects the somatic soybean embryo system behaves very similarly to maturing zygotic soybean embryos in vivo, and is therefore a good and rapid model system for analyzing the phenotypic effects of modifying the expression of genes in the fatty acid biosynthesis pathway. Furthermore, the model system is predictive of the fatty acid composition of seeds from plants derived from transgenic embryos. Liquid culture globular embryos transformed with a vector containing a soybean microsomal delta-15 desaturase, in a reverse orientation and under the control of soybean conglycinin promoter (pCS3FdST1R), gave rise to mature embryos with a reduced 18:3 content (WO 9311245). A number of embryos from line A2872 (control tissue transformed with pCST) and from lines 299/1/3, 299/15/1, 303/7/1, 306/3/1, 306/4/3, 306/4/5 (line 2872 transformed with plasmid pCS3FdST1R) were analyzed for fatty acid content. Fatty acid analysis was performed as described in WO 9311245 using single embryos as the tissue source. Mature, somatic embryos from each of these lines were also regenerated into soybean plants by transfer to regeneration medium as described above. A number of seeds taken from plants regenerated from these embryo lines were analyzed for fatty acid content. The relative fatty-acid composition of embryos taken from tissue transformed with pCS3FdST1R was compared with relative fatty-acid composition of seeds taken from plants derived from embryos transformed with pCS3FdST1R. Also, relative fatty acid compositions of embryos and seeds transformed with pCS3FdST1R were compared with control tissue, transformed with pCST. In all cases where a reduced 18:3 content was seen in a transgenic embryo line, compared with the control, a reduced 18:3 content was also observed in segregating seeds of plants derived from that line, when compared with the control seed (Table 11).

TABLE 11

Antisense Delta-15 Desaturase:
Relative 18:3 Content Of Embryos And Seeds Of Control
(A2172) And Transgenic (299-, 303-, 306-) Soybean Lines

| Soybean Line | Embryo av. % 18:3 | Embryo lowest % 18:3 | Seed av. % 18:3* | Seed lowest % 18:3 |
|---|---|---|---|---|
| A2872 (control) | 12.1 (2.6) | 8.5 | 8.9 (0.8) | 8.0 |
| 299/1/3 | 5.6 (1.2) | 4.5 | 4.3 (1.6) | 2.5 |
| 299/15/1 | 8.9 (2.2) | 5.2 | 2.5 (1.8) | 1.4 |
| 303/7/1 | 7.3 (1.1) | 5.9 | 4.9 (1.9) | 2.8 |
| 306/3/1 | 7.0 (1.9) | 5.3 | 2.4 (1.7) | 1.3 |
| 306/4/3 | 8.5 (1.9) | 6.4 | 4.5 (2.2) | 2.7 |
| 306/4/5 | 7.6 (1.6) | 5.6 | 4.6 (1.6) | 2.7 |

*Seeds which were segregating with wild-type phenotype and without a copy of the transgene are not included in these averages. The number in brackets is S.D., n = 10.

Thus the Applicants conclude that an altered polyunsaturated fatty acid phenotype observed in a transgenic, mature somatic embryo line is predictive of an altered fatty acid composition of seeds of plants derived from that line.

Analysis Of Transgenic *Glycine Max* Embryos Containing An Antisense Microsomal Delta-12 Desaturase Construct The vectors pBS13, pBS14 and pST11 contain the soybean microsomal delta-12 desaturase cDNA, in the antisense orientation, under the control of the soybean Kunitz Trypsin Inhibitor 3 (KTi3), Phaseolus phaseolin, and soybean beta-conglycinin promoters as described above. Liquid culture globular embryos transformed with vectors pBS13, pBS14 and pST11, gave rise to mature embryo lines as described above. Fatty acid analysis was performed as described in WO 9311245 using single, mature embryos as the tissue source. A number of embryos from line A2872 (control tissue transformed with pCST) and from line A2872 transformed with vectors pBS13, pBS14 and pST11 were analyzed for fatty acid content. About 30% of the transformed lines showed an increased 18:1 content when compared with control lines transformed with pCST described above, demonstrating that the delta-12 desaturase had been inhibited in these lines. The remaining transformed lines showed relative fatty acid compositions similar to those of the control line. The relative 18:1 content of the lines showing an increased 18:1 content was as high as 50% compared with a maximum of 12.5% in the control embryo lines. The average 18:1 content of embryo lines which showed an increased 18:1 content was about 35% (Table 12). In all the lines showing an increased 18:1 content there was a proportional decrease in the relative 18:2 content (Table 13).

TABLE 12

Summary Of Experiment In Which Soybean Embryos Were Transformed With Plasmids Containing A Soybean Antisense Microsomal Delta-12 Desaturase cDNA

|  | # of Vector Lines | # of lines with high 18:1 | highest 18:1 | av. (%) 18:1 |
|---|---|---|---|---|
| pCST (control) | — | — | 12.5 | 10.5 |
| pBS13 | 11 | 4 | 53.5 | 35.9 |
| pBS14 | 11 | 2 | 48.7 | 32.6 |
| pST11 | 11 | 3 | 50.1 | 35.9 |

In Table 12 the average 18:1 of transgenics is the average of all embryos transformed with a particular vector whose relative 18:1 content is greater than two standard deviations from the highest control value (12.5). The control average is the average of ten A2872 embryos (standard deviation=1.2). The data in Table 12 are derived from Table 13 below.

TABLE 13

Relative Fatty Acid Contents Of Embryo Lines Transformed With Plasmids Containing A Soybean Antisense Delta-12 Desaturase cDNA

| Embryo Line | Relative % Fatty-Acid Content | | | | |
|---|---|---|---|---|---|
| A2872 (control) | | | | | |
| # | 16:0 | 18:0 | 18:1 | 18:2 | 18:3 |
| 1 | 11.7 | 3.2 | 11.7 | 52.7 | 16.1 |
| 2 | 16.4 | 4.0 | 10.8 | 47.1 | 19.3 |
| 3 | 17.1 | 3.4 | 8.3 | 48.3 | 20.6 |
| 4 | 15.3 | 2.7 | 9.4 | 51.1 | 19.0 |
| 5 | 15.2 | 3.6 | 10.8 | 51.0 | 17.5 |
| 6 | 18.6 | 3.9 | 10.9 | 45.8 | 18.1 |
| 7 | 14.6 | 3.4 | 12.5 | 52.3 | 16.4 |
| 8 | 14.2 | 3.5 | 11.2 | 53.9 | 16.7 |
| 9 | 15.2 | 3.2 | 9.8 | 49.5 | 16.1 |
| 10 | 19.0 | 3.8 | 9.6 | 47.4 | 19.0 |
| G335/4/197 (pBS13) | | | | | |
| # | 16:0 | 18:0 | 18:1 | 18:2 | 18:3 |
| 1 | 12.2 | 3.3 | 42.0 | 23.0 | 17.4 |
| 2 | 12.4 | 2.7 | 22.4 | 39.0 | 21.9 |
| 3 | 12.0 | 3.2 | 42.0 | 23.2 | 18.4 |
| G335/4/221 (pBS13) | | | | | |
| # | 16:0 | 18:0 | 18:1 | 18:2 | 18:3 |
| 1 | 12.2 | 2.7 | 30.4 | 36.0 | 17.9 |
| 2 | 11.5 | 2.4 | 14.3 | 53.4 | 17.6 |
| 3 | 13.0 | 2.6 | 15.2 | 47.4 | 19.9 |
| 4 | 12.0 | 2.6 | 27.4 | 37.9 | 19.1 |
| 5 | 11.7 | 2.7 | 25.1 | 42.3 | 15.6 |
| 6 | 11.7 | 3.4 | 21.6 | 44.3 | 17.8 |
| 7 | 12.0 | 2.5 | 11.3 | 53.6 | 20.0 |
| 8 | 12.0 | 2.5 | 20.8 | 44.1 | 19.5 |
| 9 | 11.7 | 2.6 | 25.3 | 39.6 | 18.3 |
| G335/8/174 (pBS13) | | | | | |
| # | 16:0 | 18:0 | 18:1 | 18:2 | 18:3 |
| 1 | 14.1 | 2.1 | 30.3 | 32.1 | 20.3 |
| 2 | 14.7 | 2.5 | 5.9 | 40.6 | 34.8 |
| 3 | 14.3 | 2.4 | 7.3 | 45.2 | 29.8 |
| G335/8/202 (pBS13) | | | | | |
| # | 16:0 | 18:0 | 18:1 | 18:2 | 18:3 |
| 1 | 11.7 | 1.5 | 30.1 | 32.4 | 23.3 |
| 2 | 11.4 | 2.3 | 48.5 | 20.6 | 16.1 |
| 3 | 12.9 | 2.3 | 46.6 | 17.1 | 19.5 |
| 4 | 12.7 | 2.6 | 32.0 | 31.1 | 20.5 |
| 5 | 12.9 | 1.9 | 41.7 | 23.5 | 18.9 |
| 6 | 12.3 | 2.6 | 40.1 | 25.6 | 17.9 |
| 7 | 11.3 | 2.4 | 53.5 | 16.6 | 14.5 |
| 8 | 11.4 | 2.5 | 15.5 | 21.7 | 17.8 |
| 9 | 10.2 | 2.0 | 45.4 | 23.2 | 18.5 |
| 10 | 12.8 | 2.2 | 43.2 | 23.5 | 16.9 |
| G335/6/42 (pBS14) | | | | | |
| # | 16:0 | 18:0 | 18:1 | 18:2 | 18:3 |
| 1 | 13.7 | 2.4 | 38.6 | 28.2 | 15.6 |
| 2 | 12.6 | 2.3 | 37.6 | 28.8 | 17.2 |
| 3 | 11.7 | 3.0 | 48.7 | 21.1 | 14.6 |
| G335/6/104 (pBS14) | | | | | |
| # | 16:0 | 18:0 | 18:1 | 18:2 | 18:3 |
| 1 | 13.8 | 2.5 | 30.5 | 35.4 | 16.0 |
| 2 | 12.3 | 2.3 | 14.6 | 53.2 | 16.4 |
| 3 | 12.7 | 2.6 | 27.1 | 36.6 | 20.0 |
| 4 | 12.6 | 2.2 | 32.1 | 34.9 | 17.4 |
| 5 | 12.7 | 2.6 | 23.2 | 41.2 | 19.3 |
| 6 | 12.6 | 2.2 | 11.7 | 52.5 | 20.1 |
| 7 | 13.3 | 2.1 | 23.3 | 41.2 | 18.4 |
| G335/1/25 (pST11) | | | | | |
| # | 16:0 | 18:0 | 18:1 | 18:2 | 18:3 |
| 1 | 13.7 | 2.8 | 50.7 | 17.5 | 12.1 |
| 2 | 14.5 | 3.0 | 41.8 | 23.5 | 15.0 |
| 3 | 13.9 | 2.9 | 49.1 | 16.8 | 13.6 |
| 4 | 12.3 | 2.8 | 47.5 | 19.3 | 14.8 |
| G335/2/7/1 (pST11) | | | | | |
| # | 16:0 | 18:0 | 18:1 | 18:2 | 18:3 |
| 1 | 15.5 | 4.3 | 21.8 | 38.0 | 17.5 |
| 2 | 17.8 | 4.1 | 22.0 | 39.5 | 14.0 |
| 3 | 15.2 | 3.0 | 20.5 | 42.2 | 16.5 |

TABLE 13-continued

Relative Fatty Acid Contents Of Embryo Lines Transformed With Plasmids Containing A Soybean Antisense Delta-12 Desaturase cDNA

| Embryo Line | Relative % Fatty-Acid Content | | | | |
|---|---|---|---|---|---|
| G335/2/118 (pST11) | | | | | |
| # | 16:0 | 18:0 | 18:1 | 18:2 | 18:3 |
| 1 | 14.1 | 2.7 | 44.7 | 22.6 | 14.0 |
| 2 | 15.8 | 2.8 | 37.7 | 26.9 | 14.8 |
| 3 | 17.3 | 3.4 | 23.3 | 37.9 | 16.0 |

N.B. All other transformed embryos (24 lines) had fatty acid profiles similar to those of the control.

One of these embryo lines, G335/1/25, had an average 18:2 content of less than 20% and an average 18:1 content greater than 45% (and as high as 53.5%). The Applicants expect, based on the data in Table 13, that seeds derived from plants regenerated from such lines will have an equivalent or greater increase in 18:1 content and an equivalent or greater increase decrease in 18:2 content.

Analysis Of Transgenic *Glycine Max* Seeds Containing An Antisense Delta-12 Desaturase Construct The vector pST11 contains the soybean microsomal delta-12 desaturase cDNA, in the antisense orientation, under the control of the soybean beta-conglycinin promoter as described above. Liquid culture globular embryos transformed with vector pST11 gave rise to mature embryo lines as described above. These embryo were germinated, as described above, without analysis. Plants regenerated from these embryos were self-fertilized and between 15 and 30 seeds were taken from each plant. These seeds were analyzed for fatty acid composition as descibed in WO 9311245. The relative fatty acid content, expressed as a percentage of the five major fatty acids are shown below in Table 13-A:

TABLE 13A

Relative Fatty Acids Contents Of Seeds Containing A Soybean Antisense Delta-12 Desaturase cDNA

| LINE # | SEED # | 16:0 | 18:0 | 18:1 | 18:2 | 18:3 |
|---|---|---|---|---|---|---|
| 336/3/4/1 | F1 | 11.4 | 2.6 | 19.7 | 55.5 | 10.3 |
| | F2 | 14.9 | 3.5 | 14.1 | 54.9 | 12.0 |
| | F3 | 10.7 | 2.6 | 22.4 | 53.0 | 10.7 |
| | F4 | 12.0 | 3.1 | 21.7 | 53.8 | 8.9 |
| | F5 | 10.7 | 2.4 | 18.8 | 55.6 | 12.2 |
| | F6 | 10.9 | 2.8 | 22.3 | 53.9 | 9.6 |
| | F7 | 11.6 | 2.6 | 19.1 | 55.9 | 10.3 |
| | F8 | 12.2 | 2.6 | 21.8 | 52.5 | 10.5 |
| | F9 | 10.6 | 2.7 | 23.8 | 51.1 | 11.5 |
| | F10 | 12.3 | 2.5 | 18.3 | 54.2 | 12.5 |
| | F11 | 12.9 | 3.6 | 12.6 | 58.4 | 12.3 |
| | F12 | 12.4 | 3.4 | 16.5 | 54.9 | 12.6 |
| | F13 | 13.4 | 3.4 | 10.5 | 55.9 | 16.8 |
| | F14 | 11.4 | 3.2 | 26.3 | 51.0 | 7.7 |
| | F15 | 11.8 | 2.9 | 20.3 | 53.7 | 11.0 |
| 336/7/1/1 | F16 | 13.2 | 2.6 | 25.8 | 43.1 | 14.8 |
| | F17 | 9.6 | 3.2 | 65.4 | 11.9 | 9.5 |
| | F18 | 10.1 | 2.6 | 41.8 | 37.0 | 8.0 |
| | F19 | 8.6 | 2.4 | 60.3 | 18.7 | 9.4 |
| | F20 | 11.4 | 3.2 | 41.5 | 30.6 | 12.9 |
| | F21 | 8.7 | 2.9 | 63.2 | 16.9 | 8.2 |
| | F22 | 10.8 | 3.0 | 39.4 | 35.2 | 11.6 |
| | F23 | 7.8 | 2.5 | 79.9 | 3.4 | 6.8 |
| | F24 | 9.0 | 2.4 | 63.0 | 17.5 | 8.1 |
| | F25 | 9.5 | 2.6 | 60.4 | 19.6 | 8.0 |
| | F26 | 8.8 | 3.5 | 67.2 | 11.5 | 8.7 |
| | F27 | 10.4 | 3.1 | 53.7 | 22.5 | 10.2 |
| | F28 | 11.1 | 3.0 | 47.0 | 27.8 | 11.1 |
| | F29 | 10.6 | 2.8 | 47.3 | 30.6 | 8.4 |
| | F30 | 9.7 | 2.7 | 59.0 | 18.2 | 10.4 |
| | F136 | 11.6 | 3.2 | 27.4 | 49.3 | 8.4 |
| | F137 | 10.7 | 2.8 | 24.2 | 53.6 | 8.3 |
| | F138 | 9.8 | 2.6 | 45.6 | 32.2 | 9.4 |
| | F139 | 12.1 | 3.2 | 47.0 | 27.2 | 10.3 |
| | F140 | 9.7 | 2.6 | 50.8 | 28.2 | 8.1 |
| | F141 | 8.4 | 3.5 | 66.3 | 12.0 | 9.4 |
| | F142 | 10.3 | 2.5 | 30.9 | 48.5 | 7.3 |
| | F143 | 9.1 | 3.6 | 72.1 | 7.0 | 7.5 |
| | F144 | 9.8 | 3.2 | 58.6 | 18.2 | 9.7 |
| | F145 | 8.3 | 2.8 | 71.8 | 9.5 | 7.0 |
| | F146 | 11.1 | 2.8 | 25.9 | 51.5 | 8.6 |
| | F147 | 9.5 | 3.0 | 43.1 | 34.5 | 9.4 |
| | F148 | 10.6 | 2.5 | 26.7 | 50.6 | 9.1 |
| | F149 | 11.7 | 3.3 | 20.2 | 55.4 | 9.0 |
| 336/7/3/3 | F31 | 11.5 | 2.7 | 20.0 | 55.0 | 10.7 |
| | F32 | 12.6 | 3.0 | 24.1 | 52.0 | 8.1 |
| | F33 | 11.6 | 2.9 | 20.5 | 56.1 | 8.5 |
| | F34 | 13.0 | 3.0 | 20.2 | 53.9 | 10.0 |
| | F35 | 11.8 | 2.8 | 20.8 | 53.2 | 11.2 |
| | F36 | 10.9 | 3.0 | 29.5 | 48.2 | 8.2 |
| | F37 | 11.2 | 3.0 | 26.4 | 49.2 | 10.0 |
| | F38 | 12.7 | 3.4 | 15.3 | 56.9 | 11.6 |
| | F39 | 11.5 | 3.2 | 19.0 | 54.6 | 11.7 |
| | F40 | 10.8 | 3.1 | 23.0 | 52.9 | 10.2 |
| | F41 | 11.0 | 3.3 | 32.1 | 45.0 | 8.4 |
| | F42 | 13.6 | 3.8 | 13.2 | 55.7 | 13.7 |
| | F43 | 10.6 | 2.7 | 25.7 | 50.9 | 10.1 |
| | F44 | 9.8 | 2.5 | 25.8 | 49.8 | 12.1 |
| | F45 | 12.4 | 3.0 | 19.7 | 53.8 | 11.1 |
| 336/7/4/11 | F46 | 11.4 | 2.9 | 36.4 | 39.4 | 9.8 |
| | F47 | 12.8 | 3.2 | 23.4 | 50.6 | 10.1 |
| | F48 | 11.0 | 2.8 | 26.0 | 49.6 | 10.4 |
| | F49 | 11.7 | 2.9 | 22.9 | 52.9 | 9.2 |
| | F50 | 10.8 | 2.9 | 32.2 | 46.6 | 7.2 |
| | F51 | 11.4 | 3.4 | 20.0 | 54.0 | 11.1 |
| | F52 | 11.6 | 3.0 | 26.6 | 49.6 | 9.0 |
| | F53 | 12.6 | 2.7 | 31.3 | 43.4 | 9.6 |
| | F54 | 10.8 | 3.4 | 23.0 | 51.3 | 11.0 |
| | F55 | 11.5 | 2.8 | 22.4 | 54.1 | 8.8 |
| | F56 | 11.1 | 2.7 | 25.8 | 50.6 | 9.5 |
| | F57 | 11.8 | 3.4 | 20.1 | 54.3 | 10.3 |
| | F58 | 13.0 | 3.3 | 21.1 | 51.2 | 11.4 |
| | F59 | 12.4 | 3.2 | 19.5 | 53.7 | 10.8 |
| | F60 | 9.7 | 2.9 | 41.7 | 37.4 | 8.1 |
| 336/7/5/7 | F61 | 11.0 | 3.5 | 43.8 | 31.2 | 10.1 |
| | F62 | 12.1 | 3.2 | 18.4 | 56.8 | 9.5 |
| | F63 | 10.9 | 3.9 | 48.6 | 26.0 | 10.4 |
| | F64 | 12.6 | 3.7 | 14.3 | 58.8 | 10.4 |
| | F65 | 9.1 | 2.9 | 61.7 | 16.6 | 9.1 |
| | F66 | 9.9 | 3.3 | 59.4 | 17.6 | 9.5 |
| | F67 | 9.5 | 2.9 | 59.3 | 16.5 | 11.2 |
| | F68 | 10.3 | 4.0 | 46.0 | 28.2 | 11.2 |
| | F69 | 11.6 | 2.5 | 30.6 | 46.4 | 8.6 |
| | F70 | 10.7 | 3.6 | 54.6 | 22.1 | 8.6 |
| | F71 | 12.5 | 4.0 | 16.0 | 56.4 | 10.9 |
| | F72 | 11.1 | 2.8 | 42.2 | 34.9 | 8.6 |
| | F73 | 11.6 | 3.4 | 23.0 | 53.4 | 8.2 |
| | F74 | 12.1 | 3.5 | 15.8 | 58.0 | 10.4 |
| | F75 | 10.8 | 3.4 | 51.4 | 24.2 | 9.7 |
| 336/7/7/19 | F76 | 11.4 | 2.7 | 41.7 | 32.8 | 11.5 |
| | F77 | 8.6 | 2.5 | 76.6 | 5.1 | 6.8 |
| | F78 | 9.5 | 3.2 | 63.2 | 14.6 | 9.1 |
| | F79 | 8.2 | 2.8 | 77.7 | 3.8 | 6.8 |
| | F80 | 9.6 | 3.4 | 69.8 | 7.9 | 9.2 |
| | F81 | 8.3 | 2.8 | 72.5 | 8.6 | 7.0 |
| | F82 | 11.1 | 2.8 | 41.5 | 31.9 | 12.3 |

TABLE 13A-continued

Relative Fatty Acids Contents Of Seeds Containing A Soybean Antisense Delta-12 Desaturase cDNA

| LINE # | SEED # | 16 0 | 18 0 | 18 1 | 18 2 | 18 3 |
|---|---|---|---|---|---|---|
|  | F83 | 10.2 | 3.0 | 65.7 | 11.2 | 9.4 |
|  | F84 | 8.8 | 2.7 | 69.7 | 10.5 | 7.6 |
|  | F85 | 8.5 | 2.9 | 75.2 | 5.5 | 7.2 |
|  | F86 | 9.5 | 2.6 | 71.3 | 7.8 | 8.3 |
|  | F87 | 10.1 | 2.9 | 60.5 | 17.1 | 9.0 |
|  | F88 | 8.5 | 2.5 | 76.6 | 4.9 | 6.8 |
|  | F89 | 9.6 | 2.4 | 68.7 | 10.5 | 8.1 |
|  | F90 | 10.7 | 3.5 | 55.1 | 20.2 | 10.4 |
|  | F150 | 9.1 | 2.9 | 66.9 | 12.5 | 8.0 |
|  | F151 | 7.8 | 2.6 | 77.1 | 6.1 | 6.1 |
|  | F152 | 9.5 | 2.9 | 29.7 | 48.8 | 8.6 |
|  | F153 | 7.6 | 2.8 | 74.9 | 6.5 | 7.6 |
|  | F154 | 12.4 | 3.1 | 18.6 | 54.7 | 10.7 |
|  | F155 | 8.4 | 2.9 | 79.0 | 3.0 | 5.8 |
|  | F156 | 10.2 | 3.3 | 51.7 | 25.4 | 9.1 |
|  | F157 | 10.5 | 2.5 | 62.5 | 15.8 | 6.3 |
|  | F158 | 9.6 | 3.3 | 71.1 | 8.5 | 6.9 |
|  | F159 | 7.3 | 2.9 | 77.4 | 4.5 | 7.4 |
|  | F160 | 12.4 | 3.3 | 20.4 | 54.4 | 9.2 |
|  | F161 | 8.9 | 2.9 | 75.4 | 5.8 | 6.4 |
|  | F162 | 12.0 | 3.7 | 38.4 | 35.2 | 10.4 |
|  | F163 | 11.1 | 3.6 | 37.9 | 36.6 | 10.7 |
|  | F164 | 8.3 | 3.7 | 77.5 | 3.5 | 6.7 |
|  | F165 | 11.0 | 2.8 | 53.6 | 20.8 | 11.1 |
| 336/7/5/5 | F91 | 12.8 | 3.7 | 17.3 | 55.3 | 10.6 |
|  | F92 | 9.1 | 2.8 | 66.3 | 12.8 | 8.5 |
|  | F93 | 8.9 | 2.2 | 70.5 | 10.4 | 7.4 |
|  | F94 | 10.5 | 2.5 | 28.1 | 50.9 | 7.6 |
|  | F95 | 10.9 | 3.2 | 42.8 | 31.9 | 10.8 |
|  | F96 | 11.4 | 3.4 | 44.9 | 30.5 | 9.5 |
|  | F97 | 11.7 | 2.7 | 35.8 | 39.5 | 9.8 |
|  | F98 | 9.7 | 2.5 | 49.0 | 27.7 | 10.9 |
|  | F99 | 12.3 | 3.5 | 15.9 | 57.1 | 10.8 |
|  | F100 | 9.4 | 3.0 | 56.7 | 21.2 | 9.3 |
|  | F101 | 9.8 | 2.6 | 64.4 | 13.4 | 9.6 |
|  | F102 | 12.3 | 2.8 | 19.6 | 54.4 | 10.7 |
|  | F103 | 10.0 | 2.9 | 57.3 | 19.0 | 10.8 |
|  | F104 | 8.9 | 2.6 | 68.7 | 12.2 | 7.3 |
|  | F105 | 10.2 | 2.1 | 56.3 | 23.3 | 7.7 |
| 336/7/7/1 | F106 | 12.3 | 3.2 | 15.7 | 57.9 | 10.6 |
|  | F107 | 11.2 | 2.7 | 18.8 | 57.4 | 9.7 |
|  | F108 | 10.9 | 3.3 | 24.3 | 50.1 | 11.2 |
|  | F109 | 12.2 | 2.5 | 21.0 | 52.5 | 11.5 |
|  | F110 | 10.8 | 2.6 | 44.5 | 30.4 | 11.5 |
|  | F111 | 9.8 | 2.9 | 33.4 | 43.9 | 9.8 |
|  | F112 | 12.5 | 2.7 | 18.0 | 55.7 | 10.7 |
|  | F113 | 12.4 | 2.8 | 18.4 | 55.2 | 11.2 |
|  | F114 | 11.0 | 2.4 | 29.3 | 49.4 | 7.5 |
|  | F115 | 13.0 | 2.9 | 15.2 | 54.8 | 13.9 |
|  | F116 | 10.6 | 2.6 | 41.1 | 35.4 | 9.8 |
|  | F117 | 11.4 | 3.1 | 21.4 | 52.7 | 11.1 |
|  | F118 | 11.2 | 3.2 | 24.7 | 51.3 | 9.4 |
|  | F119 | 12.0 | 2.5 | 24.3 | 51.4 | 9.3 |
|  | F120 | 12.2 | 2.8 | 20.5 | 51.8 | 12.3 |
| 336/7/7/3 | F121 | 11.3 | 3.0 | 23.9 | 53.0 | 8.4 |
|  | F122 | 6.7 | 2.5 | 77.7 | 4.4 | 8.0 |
|  | F123 | 7.8 | 3.2 | 70.1 | 10.2 | 8.4 |
|  | F124 | 8.4 | 3.4 | 65.1 | 12.9 | 9.7 |
|  | F125 | 11.5 | 3.2 | 16.3 | 57.6 | 11.0 |
|  | F126 | 11.5 | 2.7 | 20.1 | 51.5 | 14.2 |
|  | F127 | 11.6 | 2.6 | 24.8 | 50.8 | 9.7 |
|  | F128 | 9.2 | 2.6 | 41.5 | 38.1 | 8.7 |
|  | F129 | 7.7 | 2.6 | 78.4 | 3.6 | 7.0 |
|  | F130 | 10.4 | 2.6 | 52.6 | 24.9 | 9.4 |
|  | F131 | 12.2 | 2.9 | 20.0 | 54.8 | 9.8 |
|  | F132 | 8.0 | 3.0 | 77.0 | 4.6 | 7.0 |
|  | F133 | 10.2 | 3.3 | 22.0 | 52.9 | 11.6 |
|  | F134 | 11.8 | 3.0 | 16.3 | 56.0 | 12.9 |
|  | F135 | 8.7 | 2.6 | 53.3 | 25.2 | 9.7 |
| 336/3/3/1 | F166 | 11.8 | 3.3 | 25.9 | 49.4 | 9.6 |
|  | F167 | 13.1 | 3.5 | 15.5 | 54.8 | 13.0 |
|  | F168 | 12.9 | 2.7 | 22.8 | 51.6 | 9.9 |
|  | F169 | 12.8 | 3.0 | 17.7 | 55.6 | 10.8 |
|  | F170 | 13.7 | 3.2 | 15.4 | 55.9 | 11.8 |
|  | F171 | 12.6 | 3.1 | 17.6 | 54.2 | 12.4 |
|  | F172 | 12.7 | 3.3 | 17.6 | 54.2 | 12.2 |
|  | F173 | 11.7 | 3.2 | 15.6 | 56.8 | 12.5 |
|  | F174 | 12.5 | 3.5 | 17.2 | 56.7 | 9.9 |
|  | F175 | 12.6 | 3.1 | 22.2 | 51.2 | 10.8 |
|  | F176 | 12.7 | 3.2 | 17.6 | 54.9 | 11.5 |
|  | F177 | 12.5 | 3.0 | 22.0 | 52.1 | 10.3 |
|  | F178 | 12.3 | 2.6 | 32.2 | 43.9 | 9.0 |
|  | F179 | 12.0 | 3.0 | 17.8 | 56.0 | 11.2 |
|  | F180 | 12.6 | 3.4 | 18.8 | 55.0 | 10.1 |
|  | F181 | 11.5 | 2.5 | 27.6 | 48.1 | 10.3 |
|  | F182 | 14.9 | 3.4 | 14.7 | 49.8 | 17.1 |
|  | F183 | 10.7 | 2.5 | 24.7 | 53.9 | 8.2 |
|  | F184 | 14.1 | 3.2 | 13.2 | 54.6 | 14.8 |
|  | F185 | 13.3 | 3.6 | 16.3 | 54.8 | 11.9 |
| 336/3/4/7 | F186 | 11.9 | 4.0 | 12.7 | 58.7 | 12.8 |
|  | F187 | 11.2 | 2.8 | 21.2 | 56.1 | 8.6 |
|  | F188 | 12.3 | 3.5 | 12.3 | 58.6 | 13.2 |
|  | F189 | 12.5 | 3.8 | 12.7 | 58.2 | 12.7 |
|  | F190 | 12.4 | 3.1 | 13.5 | 55.2 | 15.8 |
|  | F191 | 13.5 | 3.7 | 12.2 | 55.9 | 14.6 |
|  | F192 | 12.1 | 2.9 | 16.4 | 56.7 | 11.8 |
|  | F193 | 11.8 | 3.5 | 14.9 | 56.8 | 13.0 |
|  | F194 | 13.0 | 3.9 | 12.5 | 56.5 | 14.0 |
|  | F195 | 11.8 | 2.8 | 19.4 | 53.9 | 12.0 |
|  | F196 | 12.7 | 3.8 | 11.1 | 58.1 | 14.2 |
|  | F197 | 12.4 | 3.5 | 15.1 | 56.1 | 12.8 |
|  | F198 | 12.2 | 3.6 | 16.2 | 57.2 | 10.8 |
|  | F199 | 13.1 | 3.1 | 13.3 | 57.4 | 13.0 |
|  | F200 | 11.8 | 4.0 | 13.5 | 58.8 | 11.9 |
|  | F201 | 11.9 | 4.1 | 12.4 | 59.6 | 11.9 |
|  | F202 | 13.0 | 4.0 | 12.1 | 56.8 | 14.1 |
|  | F203 | 13.0 | 3.6 | 15.0 | 55.6 | 12.8 |
|  | F204 | 11.8 | 4.0 | 17.9 | 55.3 | 11.0 |
|  | F205 | 13.5 | 3.9 | 10.8 | 57.0 | 14.7 |
| 336/5/7/3 | F206 | 10.2 | 2.5 | 21.3 | 54.3 | 11.6 |
|  | F207 | 11.6 | 3.5 | 14.4 | 56.6 | 14.0 |
|  | F208 | 12.4 | 3.4 | 16.6 | 55.1 | 12.4 |
|  | F209 | 12.0 | 3.3 | 23.9 | 51.4 | 9.6 |
|  | F210 | 12.8 | 3.0 | 18.0 | 55.3 | 10.8 |
|  | F211 | 11.2 | 2.7 | 25.6 | 50.3 | 10.0 |
|  | F212 | 12.8 | 3.2 | 12.1 | 57.6 | 14.3 |
|  | F213 | 11.2 | 2.8 | 18.2 | 55.4 | 12.3 |
|  | F214 | 13.8 | 2.9 | 18.6 | 51.2 | 13.5 |
|  | F215 | 11.8 | 2.2 | 21.0 | 46.4 | 18.6 |
|  | F216 | 10.9 | 2.5 | 34.2 | 43.7 | 8.6 |
|  | F217 | 10.0 | 2.6 | 36.9 | 42.8 | 7.7 |
|  | F218 | 12.0 | 2.9 | 18.1 | 54.5 | 12.4 |
|  | F219 | 11.8 | 3.2 | 19.8 | 54.2 | 11.0 |
|  | F220 | 10.3 | 2.5 | 26.7 | 49.9 | 10.6 |
|  | F221 | 12.8 | 3.3 | 17.7 | 53.2 | 13.0 |
|  | F222 | 11.7 | 2.7 | 25.6 | 49.6 | 10.4 |
|  | F223 | 12.2 | 3.2 | 15.1 | 55.6 | 13.8 |
|  | F224 | 12.2 | 3.3 | 18.8 | 55.5 | 10.2 |
|  | F225 | 11.4 | 2.4 | 27.4 | 49.0 | 9.7 |
| 336/7/3/9 | F226 | 11.7 | 3.2 | 21.1 | 52.0 | 11.9 |
|  | F227 | 12.0 | 3.2 | 14.3 | 55.6 | 14.8 |
|  | F228 | 12.0 | 3.0 | 21.9 | 52.9 | 10.2 |
|  | F229 | 11.6 | 2.9 | 18.0 | 54.8 | 12.6 |
|  | F230 | 14.0 | 3.1 | 15.6 | 55.6 | 11.6 |
|  | F231 | 11.1 | 2.5 | 23.9 | 51.8 | 10.7 |
|  | F232 | 13.0 | 2.8 | 14.0 | 57.6 | 12.6 |
|  | F233 | 12.6 | 3.1 | 17.5 | 54.8 | 12.0 |
|  | F234 | 13.6 | 3.6 | 17.8 | 51.5 | 13.4 |
|  | F235 | 13.0 | 3.7 | 16.7 | 54.2 | 12.4 |
|  | F236 | 12.8 | 3.4 | 19.0 | 53.2 | 11.6 |
|  | F237 | 10.5 | 2.5 | 30.5 | 46.6 | 9.9 |
|  | F238 | 11.5 | 2.8 | 21.5 | 54.5 | 9.5 |
|  | F239 | 13.8 | 3.0 | 17.1 | 54.6 | 11.6 |
|  | F240 | 14.3 | 3.9 | 15.3 | 53.8 | 12.7 |
|  | F241 | 14.2 | 3.4 | 9.9 | 57.9 | 14.5 |
|  | F242 | 12.5 | 2.9 | 22.8 | 52.1 | 9.7 |
|  | F243 | 11.9 | 3.3 | 22.4 | 52.4 | 10.0 |
|  | F244 | 14.5 | 2.5 | 18.4 | 45.0 | 19.6 |

TABLE 13A-continued

Relative Fatty Acids Contents Of Seeds Containing A Soybean Antisense Delta-12 Desaturase cDNA

| LINE # | SEED # | 16 0 | 18 0 | 18 1 | 18 2 | 18 3 |
|---|---|---|---|---|---|---|
|  | F245 | 11.3 | 3.2 | 26.5 | 48.4 | 10.6 |
| 336/7/3/13 | F246 | 13.0 | 2.8 | 25.8 | 46.3 | 12.1 |
|  | F247 | 12.5 | 3.3 | 16.7 | 56.5 | 10.9 |
|  | F248 | 11.6 | 2.7 | 31.0 | 44.1 | 10.5 |
|  | F249 | 13.6 | 4.0 | 14.2 | 53.4 | 14.8 |
|  | F250 | 10.8 | 3.0 | 36.8 | 41.2 | 8.2 |
|  | F251 | 13.5 | 2.6 | 16.4 | 50.1 | 17.4 |
|  | F252 | 14.2 | 2.9 | 18.1 | 53.4 | 11.3 |
|  | F253 | 13.7 | 3.7 | 18.9 | 49.2 | 14.5 |
|  | F254 | 11.4 | 2.7 | 28.8 | 47.8 | 9.2 |
|  | F255 | 12.9 | 3.6 | 18.4 | 52.9 | 12.2 |
|  | F256 | 11.2 | 3.0 | 23.9 | 50.2 | 11.6 |
|  | F257 | 13.2 | 3.2 | 18.7 | 53.2 | 11.8 |
|  | F258 | 10.8 | 2.9 | 31.0 | 45.9 | 9.3 |
|  | F259 | 13.0 | 3.8 | 17.5 | 53.7 | 12.0 |
|  | F260 | 13.2 | 3.6 | 18.5 | 50.7 | 14.0 |
|  | F261 | 12.6 | 3.8 | 24.2 | 49.7 | 9.6 |
|  | F262 | 14.7 | 3.2 | 14.1 | 54.0 | 14.0 |
|  | F263 | 14.7 | 4.5 | 11.3 | 55.3 | 14.1 |
|  | F264 | 12.8 | 3.2 | 19.4 | 54.4 | 10.1 |
|  | F265 | 12.2 | 3.7 | 14.6 | 56.2 | 13.3 |
| 336/7/4/2 | F266 | 12.5 | 3.9 | 46.6 | 28.2 | 8.8 |
|  | F267 | 9.6 | 2.5 | 61.8 | 18.5 | 7.1 |
|  | F268 | 10.1 | 2.9 | 62.6 | 13.8 | 9.8 |
|  | F269 | 12.4 | 3.2 | 25.5 | 49.5 | 9.1 |
|  | F270 | 8.2 | 3.0 | 72.1 | 9.2 | 6.8 |
|  | F271 | 14.3 | 3.8 | 14.8 | 57.2 | 9.8 |
|  | F272 | 12.2 | 3.3 | 17.6 | 49.0 | 17.9 |
|  | F273 | 11.7 | 3.2 | 41.7 | 34.3 | 8.8 |
|  | F274 | 11.6 | 3.5 | 44.1 | 30.1 | 10.5 |
|  | F275 | 13.5 | 3.5 | 22.4 | 48.7 | 11.8 |
|  | F276 | 12.5 | 3.4 | 23.1 | 48.6 | 12.4 |
|  | F277 | 13.0 | 3.8 | 22.6 | 49.0 | 11.6 |
|  | F278 | 12.3 | 3.7 | 27.1 | 46.5 | 10.4 |
|  | F279 | 10.6 | 3.0 | 58.2 | 19.5 | 8.6 |
|  | F280 | 12.8 | 4.0 | 13.0 | 59.7 | 10.4 |
|  | F281 | 12.8 | 3.4 | 17.4 | 56.6 | 9.8 |
|  | F282 | 10.6 | 4.4 | 46.3 | 29.5 | 9.1 |
|  | F283 | 13.4 | 4.4 | 23.7 | 47.2 | 11.3 |
|  | F284 | 11.2 | 3.0 | 29.2 | 46.7 | 9.4 |
|  | F285 | 11.9 | 3.5 | 36.8 | 38.5 | 8.8 |
| 336/7/4/9 | F286 | 9.9 | 2.6 | 39.6 | 37.8 | 10.1 |
|  | F287 | 8.9 | 2.7 | 57.3 | 23.6 | 7.5 |
|  | F288 | 10.4 | 2.6 | 45.2 | 33.2 | 8.0 |
|  | F289 | 10.0 | 2.9 | 30.3 | 46.3 | 10.5 |
|  | F290 | 10.7 | 2.5 | 34.9 | 42.4 | 9.3 |
|  | F291 | 9.9 | 2.9 | 52.8 | 25.2 | 8.7 |
|  | F292 | 10.5 | 2.4 | 39.0 | 38.1 | 9.6 |
|  | F293 | 9.2 | 2.7 | 33.8 | 43.9 | 10.2 |
|  | F294 | 11.6 | 2.7 | 29.0 | 46.6 | 9.9 |
|  | F295 | 12.2 | 2.8 | 18.0 | 56.6 | 10.2 |
|  | F296 | 10.7 | 2.7 | 17.4 | 56.6 | 12.5 |
|  | F297 | 10.4 | 2.4 | 27.1 | 41.9 | 7.7 |
|  | F298 | 10.4 | 2.8 | 19.8 | 58.1 | 8.7 |
|  | F299 | 10.9 | 2.6 | 18.0 | 57.9 | 10.3 |
|  | F300 | 9.4 | 2.4 | 40.4 | 39.4 | 7.8 |
|  | F301 | 9.5 | 2.7 | 45.8 | 33.5 | 8.0 |
|  | F302 | 10.0 | 2.5 | 40.1 | 38.0 | 9.4 |
|  | F303 | 9.4 | 2.6 | 45.1 | 33.2 | 9.1 |
|  | F304 | 10.6 | 2.8 | 22.9 | 51.9 | 11.8 |
|  | F305 | 10.1 | 2.3 | 34.5 | 45.1 | 7.8 |
| 336/7/6/10 | F306 | 8.8 | 3.4 | 71.4 | 9.1 | 7.3 |
|  | F307 | 13.0 | 3.0 | 20.5 | 56.0 | 7.4 |
|  | F308 | 7.8 | 3.0 | 76.3 | 5.6 | 6.8 |
|  | F309 | 11.1 | 3.1 | 24.4 | 54.2 | 7.1 |
|  | F310 | 9.3 | 2.5 | 63.5 | 11.2 | 13.5 |
|  | F311 | 9.3 | 3.4 | 70.0 | 9.1 | 8.1 |
|  | F312 | 8.0 | 3.8 | 61.1 | 16.4 | 10.5 |
|  | F313 | 8.6 | 3.3 | 64.1 | 14.5 | 9.5 |
|  | F314 | 8.7 | 3.1 | 72.5 | 9.7 | 5.7 |
|  | F315 | 9.0 | 3.6 | 58.0 | 20.8 | 8.5 |
|  | F316 | 12.3 | 3.8 | 14.5 | 59.8 | 9.4 |
|  | F317 | 10.1 | 3.9 | 13.6 | 63.6 | 8.8 |
|  | F318 | 10.9 | 3.1 | 16.6 | 57.3 | 12.1 |
|  | F319 | 8.7 | 2.7 | 74.1 | 7.5 | 6.8 |
|  | F320 | 10.4 | 3.1 | 63.2 | 13.2 | 9.8 |
|  | F321 | 9.6 | 3.2 | 50.4 | 28.2 | 8.6 |
|  | F322 | 7.6 | 3.4 | 57.4 | 23.4 | 8.0 |
|  | F323 | 9.1 | 2.8 | 66.0 | 14.6 | 7.4 |
|  | F324 | 10.3 | 3.3 | 60.0 | 15.6 | 10.7 |
|  | F325 | 10.1 | 3.5 | 53.7 | 21.8 | 10.7 |
| 336/7/7/9 | F326 | 12.3 | 3.9 | 16.5 | 57.8 | 9.4 |
|  | F327 | 8.4 | 3.1 | 72.8 | 7.6 | 7.4 |
|  | F328 | 11.2 | 2.9 | 34.6 | 43.4 | 7.8 |
|  | F329 | 9.5 | 3.3 | 60.8 | 16.6 | 9.8 |
|  | F330 | 11.7 | 3.2 | 31.5 | 44.7 | 8.7 |
|  | F331 | 12.2 | 2.9 | 22.8 | 53.3 | 8.8 |
|  | F332 | 9.7 | 2.6 | 52.9 | 26.6 | 8.2 |
|  | F333 | 12.2 | 3.3 | 28.7 | 47.6 | 8.2 |
|  | F334 | 10.4 | 3.6 | 54.3 | 21.8 | 9.8 |
|  | F335 | 10.0 | 3.3 | 64.9 | 11.8 | 10.0 |
|  | F336 | 9.0 | 3.0 | 73.2 | 6.0 | 8.7 |
|  | F337 | 9.2 | 2.7 | 68.8 | 10.1 | 9.2 |
|  | F338 | 9.9 | 3.0 | 62.7 | 14.7 | 9.6 |
|  | F339 | 8.5 | 3.2 | 72.2 | 6.6 | 9.4 |
|  | F340 | 12.8 | 3.7 | 15.2 | 55.2 | 13.0 |
|  | F341 | 13.2 | 2.8 | 22.5 | 49.8 | 11.7 |
|  | F342 | 11.2 | 4.2 | 42.1 | 30.8 | 11.6 |
|  | F343 | 12.6 | 3.9 | 26.8 | 44.9 | 11.7 |
|  | F344 | 9.1 | 3.3 | 66.6 | 10.8 | 9.9 |
|  | F345 | 13.8 | 4.3 | 17.9 | 43.0 | 21.0 |
| 336/7/7/17 | F346 | 9.9 | 3.2 | 58.2 | 17.5 | 11.2 |
|  | F347 | 9.1 | 2.8 | 75.0 | 4.8 | 7.8 |
|  | F348 | 8.8 | 2.8 | 64.1 | 14.0 | 10.2 |
|  | F349 | 9.7 | 2.9 | 56.4 | 20.0 | 11.0 |
|  | F350 | 13.9 | 3.9 | 12.8 | 51.1 | 18.2 |
|  | F351 | 9.2 | 3.3 | 70.0 | 7.8 | 9.6 |
|  | F352 | 11.3 | 2.5 | 44.4 | 32.9 | 8.9 |
|  | F353 | 12.2 | 3.0 | 20.6 | 53.8 | 10.4 |
|  | F354 | 12.0 | 2.8 | 22.1 | 52.8 | 10.4 |
|  | F355 | 14.1 | 3.5 | 15.2 | 54.2 | 13.1 |
|  | F356 | 12.7 | 3.0 | 19.7 | 54.2 | 10.4 |
|  | F357 | 8.0 | 2.4 | 71.4 | 11.2 | 7.0 |
|  | F358 | 13.0 | 3.4 | 14.3 | 56.1 | 13.1 |
|  | F359 | 8.3 | 3.0 | 69.4 | 10.3 | 8.8 |
|  | F360 | 8.7 | 2.6 | 75.8 | 4.7 | 7.8 |
|  | F361 | 13.1 | 3.3 | 25.4 | 44.8 | 13.3 |
|  | F362 | 10.6 | 3.6 | 56.0 | 17.2 | 12.6 |
|  | F363 | 13.9 | 4.0 | 12.6 | 55.5 | 14.0 |
|  | F364 | 12.9 | 3.8 | 20.7 | 51.0 | 11.4 |
|  | F365 | 12.7 | 2.6 | 29.0 | 42.7 | 12.8 |

The 18:1 content of 95 seeds taken from non-transformed A2872 soybean seeds ranged from 9.9% to 32.2% with a mean 18:1 content of 18.4%. Segregating seeds of plants derived from embryos transformed with pST11 ranged from 12.6% to 79.9% with a mean of 44.6% (Table 13-A). Seeds which had an elevated 18:1 content relative to untransformed plants also had a reduced total saturate content. For example, the total saturate content of untransformed A2872 seeds is around 15% (11% 16:0, 4% 18:0). The total saturate content of seed F122 (line 336/7/7/3, 18:1 content 77.7%) was 9.2% (6.7% 16:0, 2.5% 18:0).

Example 7

EXPRESSION OF MICROSOMAL DELTA-12 DESATURASE IN CANOLA

Construction Of Vectors For Transformation of *Brassica Napus* For Reduced Expression of Microsomal Delta-12 Desaturases in Developing Canola Seeds An extended poly A tail was removed from the canola delta-12 desaturase sequence contained in plasmid pCF2-

165D and additional restriction sites for cloning were introduced as follows. A PCR primer was synthesized corresponding to bases 354 through 371 of SEQ ID NO:3. The second PCR primer was synthesized as the complement to bases 1253 through 1231 with 15 additional bases (GCAGATATCGCGGCC) added to the 5' end. The additonal bases encode both an EcoRV site and a NotI site. pCF2-165D was used as the template for PCR amplification using these primers. The 914 base pair product of PCR amplification was digested with EcoRV and PflMI to give an 812 base pair product corresponding to bases 450 through 1253 of pCF2-165D with the added NotI site.

pCF2-165D was digested with PstI, the PstI overhang was blunted with Klenow fragment and then digested with PflMI. The 3.5 kB fragment corresponding to pBluescript along with the 5' 450 bases of the canola Fad2 cDNA was gel purified and ligated to the above described 812 base pair fragment. The ligation product was amplified by transformation of E. coli and plasmid DNA isolation. The EcoRI site remaining at the cloning junction between pBluescript and the canola Fad2 cDNA was destroyed by digestion, blunting and religation. The recovered plasmid was called pM2CFd2.

pM2CFd2 was digested with EcoRV and SmaI to remove the Fad2 insert as a blunt ended fragment. The fragment was gel purified and cloned into the SmaI site of pBC (Stratagene, La Jolla, Calif.). A plasmid with the NotI site introduced by PCR oriented away from the existing NotI site in pBC was identified by NotI digestion and gel fractionation of the digests. The resulting construct then had NotI sites at both ends of the canola Fad2 cDNA fragment and was called pM3CFd2.

Vectors for transformation of the antisense cytoplasmic delta-12 desaturase constructions under control of the B-conglycinin, Kunitz trypsin inhibitor III, napin and phaseolin promoters into plants using *Agrobaterium tumefaciens* were produced by constructing a binary Ti plasmid vector system (Bevan, (1984) Nucl. Acids Res. 12:8711–8720). One starting vector for the system, (pZS199) is based on a vector which contains: (1) the chimeric gene nopaline synthase/neomycin phosphotransferase as a selectable marker for transformed plant cells (Brevan et al. (1984) Nature 304: 184–186), (2) the left and right borders of the T-DNA of the Ti plasmid (Brevan et al. (1984) Nucl. Acids Res. 12:8711–8720), (3) the *E. coli* lacZ a-complementing segment (Vieria and Messing (1982) Gene 19:259–267) with unique restriction endonuclease sites for Eco RI, Kpn I, Bam HI, and Sal I, (4) the bacterial replication origin from the Pseudomonas plasmid pVS1 (Itoh et al. (1984) Plasmid 11:206–220), and (5) the bacterial neomycin phosphotransferase gene from Tn5 (Berg et al. (1975) Proc. Natnl. Acad. Sci. U.S.A. 72:3628–3632) as a selectable marker for transformed *A. tumefaciens*. The nopaline synthase promoter in the plant selectable marker was replaced by the 35S promoter (Odell et al. (1985) Nature, 313:810–813) by a standard restriction endonuclease digestion and ligation strategy. The 35S promoter is required for efficient *Brassica napus* transformation as described below. A second vector (pZS212) was constructed by reversing the order of restriction sites in the unique site cloning region of pZS199

Canola napin promoter expression cassettes were consturcted as follows: Ten oligonucleotide primers were synthesized based upon the nucleotide sequence of napin lambda clone CGN1-2 published in European Patent Application EP 255378). The oligonucleotide sequences were:

BR42 and BR43 corresponding to bases 1132 to 1156 (BR42) and the complement of bases 2248 to 2271 (BR43) of the sequence listed in FIG. 2 of EP 255378.

BR45 and BR46 corresponding to bases 1150 to 1170 (BR46) and the complement of bases 2120 to 2155 (BR45) of the sequence listed in FIG. 2 of EP 255378. In addition BR46 had bases corresponding to a Sal I site (5'-GTCGAC-3') and a few additional bases (5'-TCAGGCCT-3') at its 5' end and BR45 had bases corresponding to a Bgl II site (5'-AGATCT-3') and two (5'-CT-3') additional bases at the 5' end of the primer, BR47 and BR48 corresponding to bases 2705 to 2723 (BR47) and bases 2643 to 2666 (BR48) of the sequence listed in FIG. 2 of EP 255378. In addition BR47 had two (5'-CT-3') additional bases at the 5' end of the primer followed by bases corresponding to a Bgl II site (5'-AGATCT-3') followed by a few additional bases (5'-TCAGGCCT-3'), BR49 and BR50 corresponding to the complement of bases 3877 to 3897 (BR49) and the complement of bases 3985 to 3919 (BR50) of the sequence listed in FIG. 2 of EP 255378. In addition BR49 had bases corresponding to a Sal I site (5'-GTCGAC-3') and a few additional bases (5'-TCAGGCCT-3') at its 5' end, BR57 and BR58 corresponding to the complement of bases 3875 to 3888 (BR57) and bases 2700 to 2714 (BR58) of the sequence listed in FIG. 2 of EP 255378. In addition the 5' end of BR57 had some extra bases (5'-CCATGG-3') followed by bases corresponding to a Sac I site (5'-GAGCTC-3') followed by more additional bases (5'-GTCGACGAGG-3'). The 5' end of BR58 had additional bases (5'-GAGCTC-3') followed by bases corresponding to a Nco I site (5'-CCATGG-3') followed by additional bases (5'-AGATCTGGTACC-3').

BR61 and BR62 corresponding to bases 1846 to 1865 (BR61) and bases 2094 to 2114 (BR62) of the sequence listed in FIG. 2 of EP 255378. In addition the 5' end of BR 62 had additional bases (5'-GACA-3') followed by bases corresponding to a Bgl II site (5'-AGATCT-3') followed by a few additional bases (5'-GCGGCCGC-3').

Genomic DNA from the canola variety 'Hyola401' (Zeneca Seeds) was used as a template for PCR amplification of the napin promoter and napin terminator regions. The promoter was first amplified using primers BR42 and BR43, and reamplified using primers BR45 and BR46. Plasmid pIMC01 was derived by digestion of the 1.0 kb promoter PCR product with SalI/BglII and ligation into SalI/BamHI digested pBluescript SK+ (Stratagene). The napin terminator region was amplified using primers BR48 and BR50, and reamplified using primers BR47 and BR49. Plasmid pIMC06 was derived by digestion of the 1.2 kb terminator PCR product with SalI/BglII and ligation into SalI/BglII digested pSP72 (Promega). Using pIMC06 as a template, the terminator region was reamplified by PCR using primer BR57 and primer BR58. Plasmid pIMC101 containing both the napin promoter and terminator was generated by digestion of the PCR product with SacI/NcoI and ligation into SacI/NcoI digested pIMC01. Plasmid pIMC101 contains a 2.2 kb napin expression cassette including complete napin 5' and 3' non-translated sequences and an introduced NcoI site at the translation start ATG. Primer BR61 and primer BR62 were used to PCR amplify an ~270 bp fragment from the 3' end of the napin promoter. Plasmid pIMC401 was obtained by digestion of the resultant PCR product with EcoRI/BglII and ligation into EcoRI/BglII digested pIMC101. Plasmid pIMC401 contains a 2.2 kb napin expression cassette lacking the napin 5' non-translated sequence and includes a NotI site at the transcription start.

To construct the antisense expression vector, pM3CFd2 was digested with NotI as was pIMC401. The delta-12 desaturase containing insert from the digest of pM3CFd2 was gel isolated and ligated into the NotI digested and phosphatase treated pIMC401. An isolate in which the delta-12 desaturase was oriented antisense to the napin promoter was selected by digestion with XhoI and PflMI to give plasmid pNCFd2R. pNCFd2R was digested with SalI, phosphatase treated and ligated into pZS212 which had been opened by the same treatment. A plasmid with desired orientation of the introduced napin:delta-12 desaturase antisense transcription unit relative to the selectable marker was chosen by digestion with PvuI and the resulting binary vector was given the name pZNCFd2R.

Plasmid pML70 (described in Example 6 above) was digested with NcoI, blunted then digested with KpnI. Plasmid pM2CFd was digested with KpnI and SmaI and the isolated fragment ligated into the opened pML70 to give the antisense expression cassette pMKCFd2R. The promotor:delta-12 desaturase:terminator sequence was removed from pMKCFd2R by BamHI digestion and ligated into pZS199 which had been BamHI digested and phosphatase treated. The desired orientation relative to the selectable marker was determined by digestion with XhoI and PflMI to give the expression vector pZKCFd2R.

The expression vector containing the β-conglicinin promoter was constructed by SmaI and EcoRV digestion of pM2CFd2 and ligation into SmaI cut pML109A. An isolate with the antisense orientation was identified by digestion with XhoI and PflmI, and the transcription unit was isolated by SalI and EcoRI digestion. The isolated SalI-EcoRI fragment was ligated into EcoRI-SalI digested pZS199 to give pCCFd2R.

The expression vector containing the phaseolin promoter was obtained using the same proceedure with pCW108 as the starting, promoter containing vector and pZS212 as the binary portion of the vector to give pZPhCFd2R.

Agrobacterium-Mediated Transformation Of
Brassica Napus

The binary vectors pZNCFd2R, pZCCFd2R, pZPhCFd2R, and pZNCFd2R were transferred by a freeze/thaw method (Holsters et al. (1978) Mol Gen Genet 163:181–187) to the Agrobacterium strain LBA4404/pAL4404 (Hockema et al. (1983), Nature 303:179–180).

Brassica napus cultivar "Westar" was transformed by co-cultivation of seedling pieces with disarmed Agrobacterium tumefaciens strain LBA4404 carrying the the appropriate binary vector.

B. napus seeds were sterilized by stirring in 10% Chlorox, 0.1% SDS for thirty min, and then rinsed thoroughly with sterile distilled water. The seeds were germinated on sterile medium containing 30 mM $CaCl_2$ and 1.5% agar, and grown for six days in the dark at 24° C.

Liquid cultures of Agrobacterium for plant transformation were grown overnight at 28° C. in Minimal A medium containing 100 mg/L kanamycin. The bacterial cells were pelleted by centrifugation and resuspended at a concentration of $10^8$ cells/mL in liquid Murashige and Skoog Minimal Organic medium containing 100 μM aceto-syringone.

B. napus seedling hypocotyls were cut into 5 mm segments which were immediately placed into the bacterial suspension. After 30 min, the hypocotyl pieces were removed from the bacterial suspension and placed onto BC-35 callus medium containing 100 μM acetosyringone. The plant tissue and Agrobacteria were co-cultivated for three days at 24° C. in dim light.

The co-cultivation was terminated by transferring the hypocotyl pieces to BC-35 callus medium containing 200 mg/L carbenicillin to kill the Agrobacteria, and 25 mg/L kanamycin to select for transformed plant cell growth. The seedling pieces were incubated on this medium for three weeks at 28° C. under continuous light.

After four weeks, the segments were transferred to BS-48 regeneration medium containing 200 mg/L carbenicillin and 25 mg/L kanamycin. Plant tissue was subcultured every two weeks onto fresh selective regeneration medium, under the same culture conditions described for the callus medium. Putatively transformed calli grew rapidly on regeneration medium; as calli reached a diameter of about 2 mm, they were removed from the hypocotyl pieces and placed on the same medium lacking kanamycin.

Shoots began to appear within several weeks after transfer to BS-48 regeneration medium. As soon as the shoots formed discernable stems, they were excised from the calli, transferred to MSV-1A elongation medium, and moved to a 16:8 h photoperiod at 24° C.

Once shoots had elongated several internodes, they were cut above the agar surface and the cut ends were dipped in Rootone. Treated shoots were planted directly into wet Metro-Mix 350 soilless potting medium. The pots were covered with plastic bags which were removed when the plants were clearly growing—after about ten days.

Plants were grown under a 16:8 h photoperiod, with a daytime temperature of 23° C. and a nightime temperature of 17° C. When the primary flowering stem began to elongate, it was covered with a mesh pollen-containment bag to prevent outcrossing. Self-pollination was facilitated by shaking the plants several times each day. Fifty-one plants have thus far been obtained from transformations using both pZCCFd2R and pZPhCFd2R, 40 plants have been obtained from pZKCFd2R and 26 from pZNCFd2R.

Minimal A Bacterial Growth Medium
  Dissolve in distilled water:
  10.5 grams potassium phosphate, dibasic
  4.5 grams potassium phosphate, monobasic
  1.0 gram ammonium sulfate
  0.5 gram sodium citrate, dihydrate
  Make up to 979 mL with distilled water
  Autoclave
  Add 20 mL filter-sterilized 10% sucrose
  Add 1 mL filter-sterilized 1 M $MgSO_4$
Brassica Callus Medium BC-35
  Per liter:
  Murashige and Skoog Minimal Organic Medium (MS salts, 100 mg/L i-inositol, 0.4 mg/L thiamine;
  GIBCO #510-3118)
  30 grams sucrose
  18 grams mannitol
  0.5 mg/L 2,4-D
  0.3 mg/L kinetin
  0.6% agarose
  pH 5.8
Brassica Regeneration Medium BS-48
  Murashige and Skoog Minimal Organic Medium
  Gamborg B5 Vitamins (SIGMA #1019)
  10 grams glucose
  250 mg xylose
  600 mg MES
  0.4% agarose
  pH 5.7

Filter-sterilize and add after autoclaving:
2.0 mg/L zeatin
0.1 mg/L IAA
Brassica Shoot Elongation Medium MSV-1A
  Murashige and Skoog Minimal Organic Medium
  Gamborg B5 Vitamins
  10 grams sucrose
  0.6% agarose
  pH 5.8

Analysis Of Transgenic *Brassica Napus* Seeds
Containing An Antisense Microsomal Delta-12
Desaturase Construct Fifty-one plants were obtained from transformation with both pZPhCFd2R and pZCCFd2R, 40 were obtained from pZKCFd2R, and 26 from pZNCFd2R. The relative levels of oleate (18:1), linoleate (18:2) and linolinate (18:3) change during development so that reliable determination of seed fatty acid phenotype is best obtained from seed which has undergone nomal maturation and drydown. Relatively few transformed plants have gone through to maturity, however seeds were sampled from plants which had been transferred to pots for at least 80 days and which had pods that had yellowed and contained seeds with seed coats which had black pigmentation. Plants were chosen for early anlaysis based on promotor type, presence and copy number of the inserted delta-12 desaturase antisense gene and fertility of the plant.

Fatty acid analysis was done on either individual seeds from transformed and control plants, or on 40 mg of bulk seed from individual plants as described in Example 6. Southern analysis for detection of the presence of canola delta-12 desaturase antisense genes was done on DNA obtained from leaves of transformed plants. DNA was digested either to release the promotor:delta-12 desaturase fragment from the transformation vector or to cut outside the coding region of the delta-12 desaturase antisense gene, but within the left and right T-DNA borders of the vector.

Since the fatty acid analysis was done on seeds from the primary transformant, individual seed should be segregating for the presense of the transgene copy or copies. The segregating phenotypes serve as an internal control for the effect of the delta-12 desaturase antisense gene. The relative fatty acid phenotypes for 10 individual westar seeds, 10 individual 151-22 seeds and 12 individual 158-8 seeds are given in Table 15 below.

TABLE 15

Relative Fatty Acid Profiles for Individual Seeds of Control and Genetically Segregating Delta-12 Desaturase Transformed Brassica Napus Seeds

| 16:0 | 18:0 | 18:1 | 18:2 | 18:3 |
|---|---|---|---|---|
| \multicolumn{5}{c}{westar control} ||||| 
| 4.65 | 1.05 | 63.45 | 21.31 | 7.29 |
| 4.65 | 1.37 | 65.41 | 20.72 | 6.18 |
| 3.86 | 1.31 | 62.19 | 22.50 | 8.18 |
| 4.46 | 1.41 | 66.81 | 19.40 | 5.63 |
| 4.76 | 1.30 | 61.90 | 22.39 | 7.65 |
| 4.59 | 1.10 | 64.77 | 20.62 | 6.56 |
| 4.61 | 1.16 | 68.66 | 18.20 | 5.07 |
| 4.71 | 1.26 | 67.28 | 19.32 | 5.18 |
| 4.67 | 0.98 | 61.96 | 22.93 | 7.61 |
| 4.73 | 1.33 | 63.85 | 21.65 | 6.23 |
| \multicolumn{5}{c}{151–22} ||||| 
| 4.56 | 1.08 | 73.40 | 12.40 | 7.60 |
| 4.25 | 1.20 | 77.90 | 10.00 | 5.40 |
| 4.40 | 1.00 | 76.90 | 10.10 | 5.90 |
| 4.40 | 0.94 | 77.40 | 9.40 | 6.10 |
| 4.50 | 1.00 | 73.60 | 11.30 | 7.90 |
| 4.60 | 0.98 | 75.40 | 10.50 | 6.50 |
| 4.49 | 0.96 | 76.70 | 9.90 | 6.00 |
| 4.20 | 1.10 | 77.20 | 9.70 | 5.50 |
| 4.20 | 1.00 | 80.00 | 7.90 | 4.90 |
| 4.50 | 1.00 | 78.00 | 8.80 | 5.80 |
| \multicolumn{5}{c}{158–8} ||||| 
| 3.62 | 1.67 | 84.45 | 3.60 | 3.73 |
| 3.46 | 1.64 | 85.56 | 3.02 | 3.36 |
| 3.48 | 1.61 | 83.64 | 4.43 | 4.21 |

TABLE 14

Relative Fatty Acid Profiles of Microsomal Delta-12 Desaturase Antisense Transformed and Control Brasstcia Napus Seeds

| | | | | \multicolumn{5}{c}{% of TOTAL FATTY ACIDS} |||||
| PLANT # | PROMOTER | COPY # | AGE* | 16:0 | 18:0 | 18:1 | 18:2 | 18:3 |
|---|---|---|---|---|---|---|---|---|
| Westar | control | none | 82 | 4.6 | 1.2 | 64.6 | 20.9 | 6.6 |
| 151-22 | phaseolin | >8 | 82 | 4.4 | 1.0 | 76.6 | 10.0 | 6.2 |
| 158-8 | napin | 1 | 83 | 3.5 | 1.5 | 81.3 | 6.3 | 4.6 |
| westar | control | none | 106 | 4.1 | 1.7 | 64.4 | 19.9 | 7.1 |
| 151-22 | phaseolin | >8 | 106 | 4.2 | 1.9 | 74.4 | 9.9 | 6.3 |
| 151-127 | phaseolin | 0 | 106 | 4.1 | 2.3 | 68.4 | 16.9 | 5.2 |
| 151-268 | phaseolin | 1 | 106 | 4.2 | 2.7 | 73.3 | 12.0 | 4.2 |
| 153-83 | conglycinin | 2 | 106 | 4.1 | 1.6 | 68.5 | 16.7 | 6.3 |

*Seed sampeling date in days after the plant was tranferred to soil

The expected fatty acid phenotype for antisense suppression of the delta-12 desaturase is decreased relative content of 18:2 with a corresponding increase in 18:1. Plant numbers 151-22 and 158-8 both show a substantial decrease in 18:2 content of bulk seed when compared to the westar control at 83 days after planting. Plant 151-22 also shows this difference at maturity in comparison to either the westar control or plant 151-127, which was transformed with the selectable marker gene but not the delta-12 desaturase antisense gene.

TABLE 15-continued

Relative Fatty Acid Profiles for Individual Seeds
of Control and Genetically Segregating Delta-12
Desaturase Transformed Brassica Napus Seeds

| 16:0 | 18:0 | 18:1 | 18:2 | 18:3 |
|------|------|-------|-------|------|
| 3.53 | 1.40 | 83.80 | 4.41  | 4.36 |
| 3.48 | 1.39 | 83.66 | 4.35  | 4.44 |
| 3.80 | 1.50 | 68.17 | 16.57 | 7.56 |
| 3.41 | 1.40 | 83.76 | 4.38  | 4.40 |
| 3.49 | 1.29 | 82.77 | 5.16  | 4.60 |
| 3.77 | 1.39 | 69.47 | 16.40 | 6.54 |
| 3.44 | 1.36 | 83.86 | 4.49  | 4.27 |
| 3.48 | 1.38 | 83.15 | 4.91  | 4.53 |
| 3.55 | 1.92 | 83.69 | 4.20  | 3.70 |

The westar control shows comparatively little seed to seed variation in content of 18:1 or 18:2. Further the ratio of 18:3/18:2 remains very constant between seeds at about 0.35. Plant #158-8 should show a segregation ratio of either 1:2:1 or 1:3 since by Southern analysis it contains a single transgene. The 1:2:1 ratio would indicate a semi-dominant, copy number effect while the 1:3 ratio would indicate complete dominance. Two wild type 158-8 segregants are clear in Table 15, while the remaing seeds may either be the same, or the two seeds at greater than 84% 18:1 may represent the homozygous transgeneic. In either case the fatty acid phenotypes of the seeds are as expected for effective delta-12 desaturase suppression in this generation. The fatty acid phenotypes of the seeds of plant 151-22 show variation in their 18:1 and 18:2 content, with 18:1 higher than the control average and 18:2 lower. The segregation is apparently quite complex as would be expected of a multi-copy transgenic plant.

Example 8

COMBINATION OF HIGH OLEIC TRAITS IN TRANSFORMANT 158-8-1 AND RAPESEED MUTANT IMC 129

*Brassica napus* primary transformant 158-8 that was transformed with a chimeric napin:antisense rapeseed delta-12 desaturase gene (see Example 7 herein) was selfed to give rise to seeds, designated T2 generation, that were segregating for high oleic acid phenotypes. Several high oleic T2 seeds were germinated and leaf DNA of the T2 plants was used in quantitative Southern analysis to identify individuals homozygous for the transormed chimeric gene. One homozygous T2 plant, designated 158-8-1, was selfed and the fatty acid composition of the T3 progeny determined by single seed analysis (Table 16). The data confirmed that 158-8-1 was homozygous for the high oleate trait.

TABLE 16

Fatty Acid Composition of Single Seeds of a
Selfed T2 Transgenic Rapeseed Line 158-8-1

| | Relative Fatty Acid Content (%) | | | | |
|---------|------|------|-------|------|------|
| Progeny | 16:0 | 18:0 | 18:1  | 18:2 | 18:3 |
| 1       | 3.91 | 1.59 | 82.36 | 5.75 | 5.78 |
| 2       | 3.81 | 1.53 | 83.34 | 5.55 | 5.16 |
| 3       | 3.82 | 1.55 | 85.29 | 4.47 | 4.27 |
| 4       | 3.67 | 1.75 | 83.21 | 5.05 | 5.72 |
| 5       | 3.74 | 1.79 | 82.64 | 5.29 | 5.86 |
| 6       | 3.92 | 1.63 | 83.43 | 5.51 | 4.91 |
| 7       | 3.82 | 1.47 | 84.10 | 5.10 | 4.89 |
| 8       | 3.83 | 1.67 | 82.63 | 5.97 | 5.34 |
| Average | 3.82 | 1.62 | 83.38 | 5.34 | 5.24 |

T2 plant 158-8-1 was also used as the male parent in a cross with either rapeseed cultivar Westar (control) or IMC 129. Three plants were grown from the F1 hybrid seed from each cross and selfed. Single, segregating F2 seeds from each cross were analyzed for fatty acid composition by imbibing the seeds in water overnight, removing the seed coat and cutting off approximately one-half of the outer cotyledon. Fatty acids in the partial cotyledon were analyzed by direct transesterfication in methanol and gas chromatography as described in Example 7.

The combined analysis from 272 F2 seeds from the three 158-8-1 X IMC 129 crosses and of 60 F2 seeds from two 158-8-1 X Westar crosses are shown in Table 17 as % individuals in each class of 18:1 content.

TABLE 17

Frequency Distribution of F2 seeds of 158-8-1 × IMC 129
Cross on the Basis of Oleic Acid Content

| % 18:1 class | % seeds from 158-8-1 × Westar cross | % of seeds from 158-8-1 × IMC129 cross |
|--------------|-------------------------------------|----------------------------------------|
| 61–63 | 0    | 0.4  |
| 64–66 | 16.7 | 1.1  |
| 67–69 | 5    | 1.1  |
| 70–72 | 3.3  | 5.1  |
| 73–75 | 0    | 8.8  |
| 76–78 | 13.3 | 7.0  |
| 79–81 | 45   | 7.7  |
| 82–84 | 15   | 22.1 |
| 85–87 | 1.7  | 36.8 |
| 88–90 | 0    | 9.9  |

The data shows that the average 18:1 content in F2 progeny of the cross involving IMC 129 was significantly higher than that involving Westar.

Thirty F2 half-seeds selected for their very high oleic acid content were germinated and their leaf DNA subjected to molecular analysis (Southern analysis and polymerase chain reaction) with gene specific probes to indentify 6 F2 plants that were homozygous for both the mutant delta-12 desaturase gene from IMC 129 and the transgene from 158-8-1. The fatty acid composition of the F2 seeds from which these 6 F2 plants were derived is shown in Table 18 and their average fatty acid compositions is compared to those of 158-8-1 T3 seeds Table 16) and to those of Westar control seeds Table 19).

TABLE 18

Fatty Acid Composition of Six F2 Seeds Homozygous for the Transgene and High Oleic Acid Mutation in IMC 129

| | Relative Fatty Acid Content (%) | | | | |
|---|---|---|---|---|---|
| Progeny | 16:0 | 18:0 | 18:1 | 18:2 | 18:3 |
| 1 | 2.7 | 1.9 | 89.0 | 2.1 | 3.5 |
| 2 | 3.0 | 1.4 | 89.2 | 2.4 | 3.6 |
| 3 | 3.0 | 1.3 | 88.2 | 3.0 | 3.4 |
| 4 | 2.6 | 1.3 | 90.9 | 2.4 | 2.9 |
| 5 | 3.3 | 1.1 | 84.4 | 4.6 | 6.3 |
| 6 | 3.2 | 1.3 | 88.4 | 2.65 | 4.4 |
| Average | 2.97 | 1.38 | 88.4 | 2.86 | 4.0 |

TABLE 19

Seed Fatty Acid Composition of Westar, 158-8-1 and Six Seeds Homozygous for the Transgene from 158-8-1 and High Oleic Acid Mutation from IMC 129.

| | Relative Fatty Acid Content (%) | | | | |
|---|---|---|---|---|---|
| Progeny | 16:0 | 18.0 | 18:1 | 18:2 | 18:3 |
| Westar | 4.20 | 2.20 | 63.00 | 19.90 | 10.60 |
| 158-8-1 | 3.33 | 1.63 | 83.38 | 5.34 | 5.24 |
| 158-8-1 × IMC129 | 2.97 | 1.38 | 88.40 | 2.86 | 4.02 |

The data in Table 19 shows that the the seed oleic acid content in the double homozygotes resulting from the 158-8-1 X IMC 129 cross are higher than either parent and that this increase is associated with reduced saturates (16:0+ 18:0). Furthermore, the double homozygote plants appear normal in their growth and development.

What is claimed is:

1. An isolated nucleic acid fragment comprising a nucleic acid sequence encoding a plant enzyme selected from the group consisting of a delta-12 desaturase and a delta-12 hydroxylase wherein said isolated nucleic acid fragment hybridizes to one of the nucleotide sequences set forth in SEQ ID NOS:1, 3, 5, 7, 9, 11, and 15 under one of the following sets of conditions:

(a) hybridization in 50 mM Tris, pH 7.6, 6×SSC, 5×Denhardt's, 0.5% sodium dodecyl sulfate (SDS), 100 μg denatured calf thymus DNA at 50° C. and wash twice with 2×SSC, 0.5% SDS at room temperature for 15 min each, then wash twice with 0.2×SSC, 0.5% SDS at room temperature for 15 min each and then wash twice with 0.2×SSC, 0.5% SDS at 50° C. for 15 min each;

(b) hybridization in 6×SSPE, 5×Denhardt's solution, 0.5% sodium dodecyl sulfate (SDS), 5% dextran sulfate, 100 μg denatured calf thymus DNA at 50° C. and wash twice with 2×SSC, 0.5% SDS at room temperature for 15 min each, then wash twice with 0.2×SSC, 0.5% SDS at room temperature for 15 min each and then wash twice with 0.2×SSC, 0.5% SDS at 50° C. for 15 min each; or (c) hybridization in 50% formamide, 5×SSPE, 1% sodium dodecyl sulfate (SDS), 1% Denhardt's Reagent, 100 μg denatured salmon sperm DNA at 42° C. and wash twice with 2×SSPE, 0.2% SDS at 42° C. for 15 min each, then wash twice with 0.2×SSPE, 0.2% SDS at 55° C. for 30 min each.

2. The isolated nucleic acid fragment of claim 1 wherein said fragment is isolated from an oil-producing plant species.

3. An isolated nucleic acid fragment comprising a nucleic acid sequence encoding a delta-12 fatty acid hydroxylase.

4. A chimeric gene comprising the nucleic acid fragment of claim 3 operably linked to suitable regulatory sequences.

5. A chimeric gene comprising the nucleic acid fragment of claim 1 operably linked to suitable regulatory sequences.

6. Plants comprising in their genome the chimeric gene of claim 4 or claim 5.

7. An isolated nucleic acid fragment comprising a nucleic acid sequence encoding an enzyme selected from the group consisting of a delta-12 desaturase and a delta-12 hydroxylase wherein the amino acid sequence comprising said enzyme contains at least one of the following amino acid sequences selected from the group consisting of:

AIPPHCF, AWXXYW, HECGH, LLVPY, WKYSHR, and SHRRHH.

8. An isolated nucleic acid fragment encoding an enzyme selected from the group consisting of a delta-12 desaturase and a delta-12 hydroxylase wherein said isolated nucleic acid fragment encodes a protein comprising any one of the amino acid sequences set forth in SEQ ID NOS:2, 4, 6, 8, 10 or 12.

9. An isolated nucleic acid fragment encoding an enzyme selected from the group consisting of a delta-12 desaturase and a delta-12 hydroxylase wherein said isolated nucleic acid fragment hybridizes to the isolated nucleic acid fragment of claim 8 under one of the following sets of conditions:

(a) hybridization in 50 mM Tris, pH 7.6, 6×SSC, 5×Denhardt's, 0.5% sodium dodecyl sulfate (SDS), 100 μg denatured calf thymus DNA at 50° C. and wash twice with 2×SSC, 0.5% SDS at room temperature for 15 min each, then wash twice with 0.2×SSC, 0.5% SDS at room temperature for 15 min each and then wash twice with 0.2×SSC, 0.5% SDS at 50° C. for 15 min each;

(b) hybridization in 6×SSPE, 5×Denhardt's solution, 0.5% sodium dodecyl sulfate (SDS), 5% dextran sulfate, 100 μg denatured calf thymus DNA at 50° C. and wash twice with 2×SSC, 0.5% SDS at room temperature for 15 min each, then wash twice with 0.2×SSC, 0.5% SDS at room temperature for 15 min each and then wash twice with 0.2×SSC, 0.5% SDS at 50° C. for 15 min each; or (c) hybridization in 50% formamide, 5×SSPE, 1% sodium dodecyl sulfate (SDS), 1% Denhardt's Reagent, 100 μg denatured salmon sperm DNA at 42° C. and wash twice with 2×SSPE, 0.2% SDS at 42° C. for 15 min each, then wash twice with 0.2×SSPE, 0.2% SDS at 55° C. for 30 min each.

10. Seeds of the plant of claim 6.

11. The isolated nucleic acid fragment of claim 7, 8 or 9 wherein said fragment is isolated from an oil-producing plant species.

12. The chimeric gene comprising the nucleic acid fragment of claim 7, 8 or 9 operably linked to suitable regulatory sequences.

13. The isolated nucleic acid fragment of claim 7, 8 or 9 comprising a nucleic acid sequence encoding a plant microsomal delta-12 fatty acid desaturase.

* * * * *